US012637434B2

(12) United States Patent
Zhou et al.

(10) Patent No.: US 12,637,434 B2
(45) Date of Patent: May 26, 2026

(54) SALT OF ARYLAMINOQUINAZOLINE-CONTAINING COMPOUND, AND PREPARATION METHOD THEREFOR AND USE THEREOF

(71) Applicant: CSPC ZHONGQI PHARMACEUTICAL TECHNOLOGY (SHIJIAZHUANG) CO., LTD, Shijiazhuang (CN)

(72) Inventors: Fugang Zhou, Shijiazhuang (CN); Yuxia He, Shijiazhuang (CN); Yan Zhang, Shijiazhuang (CN); Jian Lyu, Shijiazhuang (CN); Kai Shi, Shijiazhuang (CN); Huifeng Di, Shijiazhuang (CN); Xinxin Yang, Shijiazhuang (CN); Jing Sun, Shijiazhuang (CN)

(73) Assignee: CSPC ZHONGQI PHARMACEUTICAL TECHNOLOGY (SHIJIAZHUANG) CO., LTD, Zhijiazhuang (CN)

(*) Notice: Subject to any disclaimer, the term of this patent is extended or adjusted under 35 U.S.C. 154(b) by 523 days.

(21) Appl. No.: 18/028,120

(22) PCT Filed: Sep. 24, 2021

(86) PCT No.: PCT/CN2021/120328

§ 371 (c)(1),
(2) Date: Mar. 23, 2023

(87) PCT Pub. No.: WO2022/063229

PCT Pub. Date: Mar. 31, 2022

(65) Prior Publication Data

US 2023/0322687 A1 Oct. 12, 2023

(30) Foreign Application Priority Data

Sep. 25, 2020 (CN) ........................ 202011022290.1

(51) Int. Cl.
*C07D 239/94* (2006.01)
*A61P 35/00* (2006.01)

(52) U.S. Cl.
CPC ............ *C07D 239/94* (2013.01); *A61P 35/00* (2018.01); *C07B 2200/13* (2013.01)

(58) Field of Classification Search
CPC .......................... C07D 239/94; C07B 2200/13
(Continued)

(56) References Cited

U.S. PATENT DOCUMENTS

| | | | | |
|---|---|---|---|---|
| 10,421,754 | B2 * | 9/2019 | Shi et al. | C07D 417/12 |
| 2004/0034022 | A1 * | 2/2004 | Barth et al. | A61K 31/5377 514/234.2 |

(Continued)

FOREIGN PATENT DOCUMENTS

| | | | |
|---|---|---|---|
| CN | 1212684 | A | 3/1999 |
| CN | 1231662 | A | 10/1999 |

(Continued)

OTHER PUBLICATIONS

Rodríguez-Spong et al., "General principles of a pharmaceutical solid polymorphism: a supramolecular perspective", *Advanced Drug Delivery Reviews*, 56: 241-274 (2004).

(Continued)

*Primary Examiner* — Jeffrey S Lundgren
*Assistant Examiner* — Heather Dahlin
(74) *Attorney, Agent, or Firm* — Leydig, Voit & Mayer, Ltd.

(57) ABSTRACT

Provided are a salt of an arylaminoquinazoline-containing compound as shown in formula 2, a solvate or hydrate thereof, a preparation method therefor and the use thereof. The prepared salt has good crystallinity, and compared to a compound in a free form, the water solubility is significantly
(Continued)

improved, and preferably, the salt form and crystal form can stably exist. Therefore, compared to a compound in a free form or other salts, the salt has better druggability.

(2)

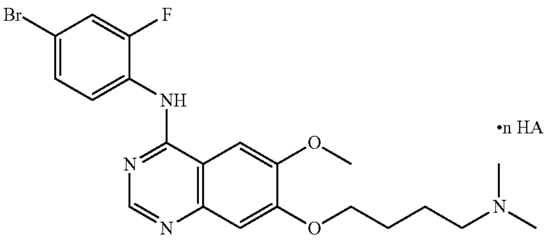

12 Claims, 19 Drawing Sheets

(58) Field of Classification Search
USPC .................................................... 514/266.4
See application file for complete search history.

(56) References Cited

U.S. PATENT DOCUMENTS

| | | | | |
|---|---|---|---|---|
| 2017/0226099 | A1 | 8/2017 | Shi et al. | |
| 2024/0025874 | A1 * | 1/2024 | Zhong et al. | C07D 401/12 |

FOREIGN PATENT DOCUMENTS

| | | | | |
|---|---|---|---|---|
| CN | 105330653 | A | 2/2016 | |
| RU | 2 704 125 | C2 | 10/2019 | |
| WO | WO 97/32856 | A1 | 9/1997 | |
| WO | WO 98/13354 | A1 | 4/1998 | |
| WO | WO 99/06378 | A1 | 2/1999 | |
| WO | WO 2009/094210 | A1 | 7/2009 | |
| WO | WO 2010/028254 | A2 | 3/2010 | |
| WO | WO2019196619 | A1 * | 10/2019 | C07D 401/12 |

OTHER PUBLICATIONS

Sarma et al., "Solid forms of pharmaceuticals: Polymorphs, salts and cocrystals", *Korean Journal of Chemical Engineering*, 28(2): 315-322 (2011).

Variankaval et al., "From Form to Function: Crystallization of Active Pharmaceutical Ingredients", *American Institute of Chemical Engineers*, 54(7): 1682-1688 (2008).

China National Intellectual Property Administration, International Search Report issued in International Patent Application No. PCT/CN2021/120328, mailed on Dec. 29, 2021.

Bastin et al., "Salt Selection and Optimisation Procedures for Pharmaceutical New Chemical Entities", *Organic Process Research & Development*, 4: 427-435 (2000).

Cairo et al., "Crystalline Polymorphism of Organic Compounds", *Topics in Current Chemistry*, 198: 163-208 (1998).

Morissette et al., "High-throughput crystallization: polymorphs, salts, co-crystals, and solvates of pharmaceutical solids", *Advanced Drug Delivery Reviews*, 56: 275-300 (2004).

Tian et al., "Factors affecting crystallization of hydrates", *Journal of Pharmacy and Pharmacology*, 62: 1534-1546 (2010).

* cited by examiner

SALT OF ARYLAMINOQUINAZOLINE-CONTAINING COMPOUND, AND PREPARATION METHOD THEREFOR AND USE THEREOF

CROSS-REFERENCE TO RELATED APPLICATIONS

The present application is the U.S. National Stage of International Patent Application No. PCT/CN2021/120328, filed Sep. 24, 2021, which claims priority to and benefit of Chinese Patent Application No. 202011022290.1 filed before the State Intellectual Property Office of China on Sep. 25, 2020, the disclosures of each of which are incorporated herein by reference in their entireties.

TECHNICAL FIELD

The present application belongs to the field of pharmaceutical chemistry, and particularly relates to salts of arylaminoquinazoline-containing compounds and preparation methods and applications thereof.

BACKGROUND OF THE INVENTION

Protein tyrosine kinases (PTKs) are a very important member of the protein kinase family. PTKs transfer the γ-phosphate group on adenosine triphosphate to the protein tyrosine residue of the substrate, and complete the information transmission between cells by phosphorylating phenolic hydroxyl groups, which plays a crucial role in cell development and regulation, and tumor cell differentiation, migration, and apoptosis and other processes. If PTKs are out of control during the regulation process, it will affect the correct activation of its downstream signaling pathway, which will in turn lead to the disorder of cell proliferation regulation function and cause many diseases. For example, the excessive activity of tyrosine kinase makes the receptor phosphorylate, and accordingly activates the downstream signaling, resulting in excessive transformation, proliferation, and anti-apoptosis of cells, promotion of cell survival, and the formation of malignancies. Therefore, using tyrosine kinases as new targets to develop this kind of kinase inhibitors to inhibit the overexpression of tyrosine kinases and restore their physiological balance has become a research hotspot in the field of molecular-targeting anti-tumor with great development prospects.

Epidermal Growth Factor Receptor (EGFR), Fibroblast Growth Factor Receptors (FGFRs), Platelet-derived Growth Factor Receptor (PDGFR), Rearranged during Transfection (RET) proto-oncogene encoded PET proteins and so on are important members of PTKs and important targets for tumor therapy.

EGFR is a cell growth factor capable of binding to receptor tyrosine kinases, including EGFR (ErbB-1), human epidermal growth factor receptor type 2 HER2 (ErbB-2), human epidermal growth factor receptor type 3 HER3 (ErbB-3), and human epidermal growth factor receptor type 4 HER4 (ErbB-4), among which EGFR and HER2 are the targets most closely related to tumor among the EGFR family members. Studies have shown that EGFR exhibits overexpression, gene mutation or gene fusion in various tumors, such as lung cancer, gastric cancer, epidermoid cancer, renal cancer, ovarian cancer, and so on.

FGFR mainly includes four subtypes, i.e., FGFR1/2/3/4, which are overexpressed or overactivated by gene amplification, mutation, fusion, or ligand induction, and play an important role in tumor cell proliferation, invasion and migration, and tumor angiogenesis. Studies have found that FGFRs exhibit overexpression or overactivation in various tumors, such as non-small cell lung cancer, gastric cancer, colorectal cancer, esophageal cancer, liver cancer, biliary tract cancer, and so on.

Normal physiological functions of RET include kidney development, nervous system development, maintenance and renewal of sperm stem cells, myelomonocyte differentiation, lymphoid tissue formation, and so on, which is expressed in cells, such as human intestinal ganglion cells, neuroblastoma, pheochromocytoma, medullary thyroid carcinoma, thyroid C cells, and melanoma. In recent years, through in-depth research on RET, it has been found that overactivation of RET in tumors can significantly promote proliferation, survival, invasion, metastasis, tumor inflammation, and the like of various tumors, and RET shows over-expression in thyroid cancer (e.g., medullary thyroid cancer, papillary thyroid cancer), colorectal cancer, pancreatic cancer, melanoma, and so on.

Compound 1, of which chemical name is 4-(4-bromo-2-fluoroanilino)-6-methoxy-7-[(4-N,N-dimethylamino)butoxy]quinazoline, is a multi-target inhibitor having inhibitory activities against RET, VEGFR (Vascular endothelial growth factor receptor), FGFR, EGFR, FLT (Fms-like tyrosine kinase or Fms Related Receptor Tyrosine Kinase)), and so on.

(1)

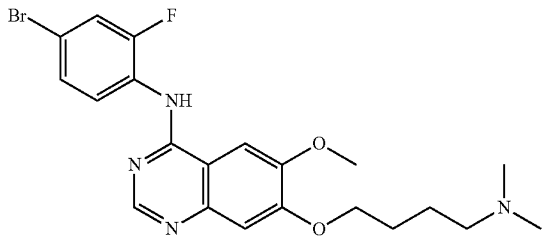

WO2016023330A1 relates to arylaminoquinazoline-containing compounds as tyrosine kinase inhibitors, and describes Compound 1 and an analog, a preparation method, and a medical use thereof.

BRIEF SUMMARY OF THE INVENTION

The inventors of the present application found that Compound 1 has a very poor water-solubility and cannot meet the general requirements for drug solubility of solid oral dosage forms (it should be greater than 0.1 g/L), let alone the development of other pharmaceutical dosage forms (for examples, injections, and solutions). Furthermore, the water-solubility of a drug is also a major factor affecting the dissolution, absorption, and pharmacokinetic properties of the drug. Therefore, it is necessary to modify Compound 1 to optimize its physicochemical properties and improve its druggability.

In one aspect, the present application provides a salt of an arylaminoquinazoline-containing compound represented hv Formula?. a solvate or hydrate thereof.

(2)

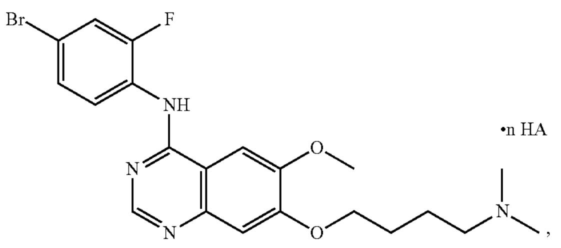

wherein,

HA is hydrochloric acid, sulfuric acid, oxalic acid or maleic acid;

n is an integer or half-integer ranging from ½ to 2; and when HA is hydrochloric acid, n is 0.5, 1.5 or 2.

In another aspect, the present application provides a crystalline form of a salt of an arylaminoquinazoline-containing compound represented by Formula 2, a solvate or hydrate thereof:

(2)

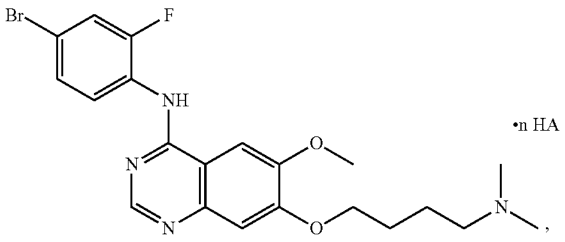

wherein,

HA is hydrochloric acid, sulfuric acid, oxalic acid or maleic acid;

n is an integer or half-integer ranging from ½ to 2; and when HA is hydrochloric acid, n is 0.5, 1.5 or 2.

In another aspect, the present application provides a pharmaceutical composition comprising the aforementioned salt of the arylaminoquinazoline-containing compound represented by Formula 2, the solvate or hydrate thereof, or the crystalline form of the salt of the arylaminoquinazoline-containing compound represented by Formula 2, the solvate or hydrate thereof, and one or more pharmaceutically acceptable carriers.

In yet another aspect, the present application provides a use of the aforementioned salt of the arylaminoquinazoline-containing compound represented by Formula 2, the solvate or hydrate thereof, or the crystalline form of the salt of the arylaminoquinazoline-containing compound represented by Formula 2, the solvate or hydrate thereof, or the aforementioned pharmaceutical composition, in the preparation of a medicament as a receptor tyrosine kinase inhibitor.

The present application also provides a use of the aforementioned salt of the arylaminoquinazoline-containing compound represented by Formula 2, the solvate or hydrate thereof, or the crystalline form of the salt of the arylaminoquinazoline-containing compound represented by Formula 2, the solvate or hydrate thereof, or the aforementioned pharmaceutical composition, in the preparation of an antitumor drug.

In yet another aspect, the present application also provides a use of the aforementioned salt of the arylaminoquinazoline-containing compound represented by Formula 2, the solvate or hydrate thereof, or the crystalline form of the salt of the arylaminoquinazoline-containing compound represented by Formula 2, the solvate or hydrate thereof, or the aforementioned pharmaceutical composition, in the treatment of a receptor tyrosine kinase-related disease.

The present application also provides a use of the aforementioned salt of the arylaminoquinazoline-containing compound represented by Formula 2, the solvate or hydrate thereof, or the crystalline form of the salt of the arylaminoquinazoline-containing compound represented by Formula 2, the solvate or hydrate thereof, or the aforementioned pharmaceutical composition, in the treatment of a tumor.

In yet another aspect, the present application also provides a method for treating a receptor tyrosine kinase-related disease in a patient, comprising administering to the patient a therapeutically effective amount of the aforementioned salt of the arylaminoquinazoline-containing compound represented by Formula 2, the solvate or hydrate thereof, or the crystalline form of the salt of the arylaminoquinazoline-containing compound represented by Formula 2, the solvate or hydrate thereof, or the aforementioned pharmaceutical composition.

The present application also provides a method for treating a tumor in a patient, comprising administering to the patient a therapeutically effective amount of the aforementioned salt of the arylaminoquinazoline-containing compound represented by Formula 2, the solvate or hydrate thereof, or the crystalline form of the salt of the arylaminoquinazoline-containing compound represented by Formula 2, the solvate or hydrate thereof, or the aforementioned pharmaceutical composition.

In yet another aspect, the present application also provides the aforementioned salt of the arylaminoquinazoline-containing compound represented by Formula 2, the solvate or hydrate thereof, or the crystalline form of the salt of the arylaminoquinazoline-containing compound represented by Formula 2, the solvate or hydrate thereof, or the aforementioned pharmaceutical composition, for use in the treatment of a receptor tyrosine kinase-related disease.

In yet another aspect, the present application also provides the aforementioned salt of the arylaminoquinazoline-containing compound represented by Formula 2, the solvate or hydrate thereof, or the crystalline form of the salt of the arylaminoquinazoline-containing compound represented by Formula 2, the solvate or hydrate thereof, or the aforementioned pharmaceutical composition, for use in the treatment of a tumor.

In yet another aspect, the present application provides a method for the preparation of a salt of an arylaminoquinazoline-containing compound represented by Formula 2, a solvate or hydrate thereof, comprising reacting an arylaminoquinazoline-containing compound represented by Formula 1 with an acid (HA) in a suitable solvent, and then isolating to obtain the salt of the arylaminoquinazoline-containing compound represented by Formula 2, the solvate or hydrate thereof:

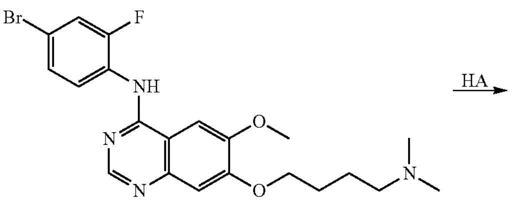

(1)

-continued

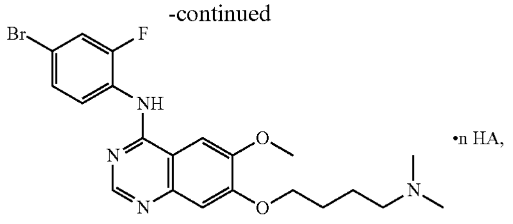

(2)

wherein,

HA is hydrochloric acid, sulfuric acid, oxalic acid or maleic acid;

n is an integer or half-integer ranging from ½ to 2; and when HA is hydrochloric acid, n is 0.5, 1.5 or 2.

BRIEF DESCRIPTION OF THE SEVERAL VIEWS OF THE DRAWING(S)

DETAILED DESCRIPTION OF THE INVENTION

Figure 1:
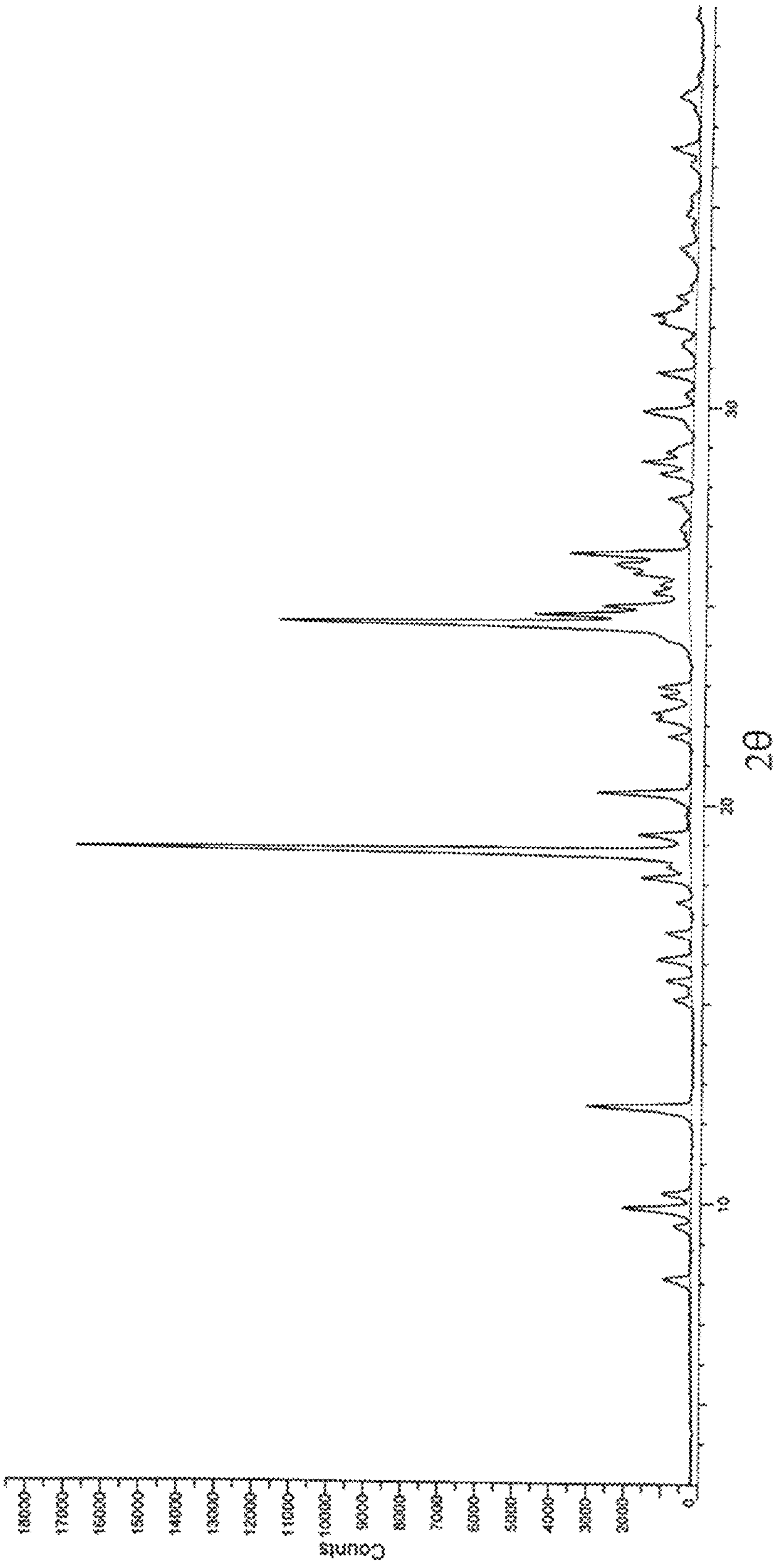
FIG. 1 is an XRPD spectrum of crystalline form I of a dihydrochloride salt of Compound 1, a solvate or hydrate thereof obtained in Example 1.

In one aspect, the present application provides a salt of an arylaminoquinazoline-containing compound represented by Formula 2, a solvate or hydrate thereof:

(2)

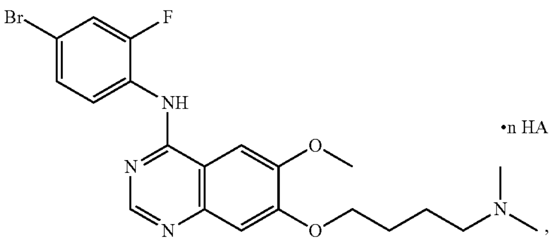

wherein HA is an acid;

n is an integer or half-integer ranging from ½ to 2 (that is, n is 0.5, 1, 1.5, or 2).

In some embodiments of the present application, HA is hydrochloric acid, sulfuric acid, oxalic acid, maleic acid, or malic acid. In some embodiments of the present application, HA is hydrochloric acid, sulfuric acid, or maleic acid. In some embodiments of the present application, HA is hydrochloric acid.

In some embodiments of the present application, HA is hydrochloric acid, sulfuric acid, oxalic acid, or maleic acid, and n is an integer or half-integer ranging from ½ to 2 (that is, n is 0.5, 1, 1.5, or 2); and when HA is hydrochloric acid, n is 0.5, 1.5, or 2. In some embodiments of the present application, n is 1 or 2.

In some embodiments of the present application, the salt of the arylaminoquinazoline-containing compound, the solvate or hydrate thereof is a hydrochloride salt of an arylaminoquinazoline-containing compound represented by Formula 3, a solvate or hydrate thereof:

(3)

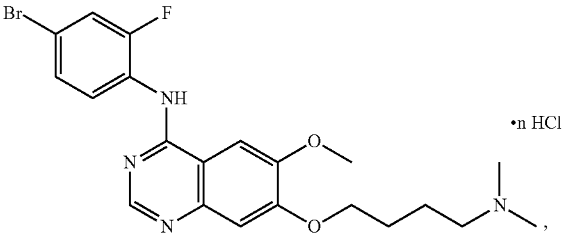

wherein n is 0.5, 1.5 or 2.

In some embodiments of the present application, the solvate is selected from the group consisting of an acetonitrile/water solvate and an ethanol solvate.

In some embodiments of the present application, the hydrate is selected from the group consisting of a hemihydrate, a monohydrate, and a tetrahydrate.

In some embodiments of the present application, the salt of the arylaminoquinazoline-containing compound, the solvate or hydrate thereof is a hydrochloride salt represented by Formula 3' or a hydrate thereof:

(3')

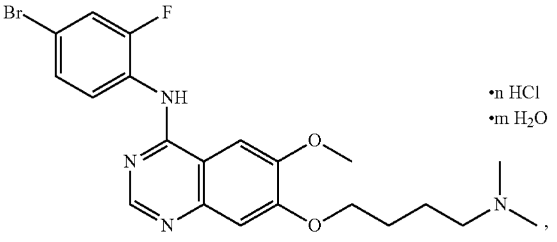

wherein n is an integer from 1 to 2; m is an integer or half-integer ranging from 0 to 4 (that is, m is 0, 0.5, 1, 1.5, 2, 2.5, 3, 3.5 or 4); and when n is 1, m is an integer or half-integer ranging from 1 to 4 (that is, m is 0.5, 1, 1.5, 2, 2.5, 3, 3.5, or 4). In some embodiments of the present application, n is 2, and m is 0, 0.5, 1, or 4. In some embodiments of the present application, n is 2, and m is 0 or 4.

In some embodiments of the present application, the salt of the arylaminoquinazoline-containing compound, the solvate or hydrate thereof is a dihydrochloride salt represented by Formula 3" or a hydrate thereof:

(3")

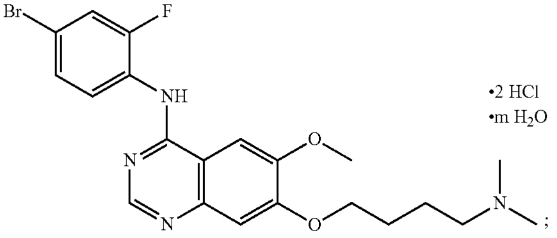

wherein m is an integer or half-integer ranging from 0 to 4 (that is, m is 0, 0.5, 1, 1.5, 2, 2.5, 3, 3.5, or 4).

In some embodiments of the present application, the salt of the arylaminoquinazoline-containing compound, the solvate or hydrate thereof is a dihydrochloride salt represented by Formula 3-1:

(3-1)

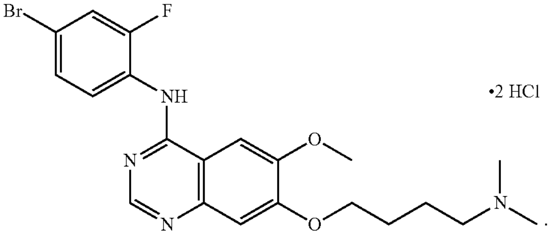

In some embodiments of the present application, the salt of the arylaminoquinazoline-containing compound, the solvate or hydrate thereof is a dihydrochloride salt tetrahydrate represented by Formula 3-2:

(3-2)

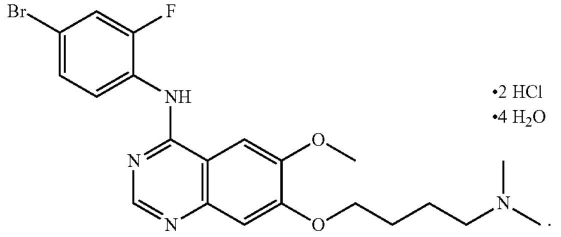

In another aspect, the present application provides a crystalline form of a salt of an arylaminoquinazoline-containing compound represented by Formula 2, a solvate or hydrate thereof:

(2)

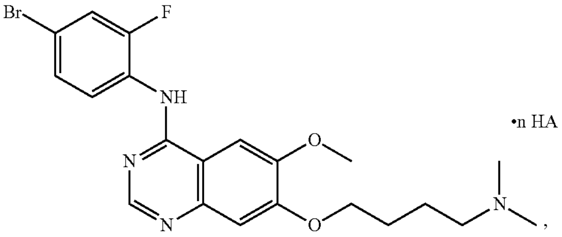

wherein HA is an acid;

n is an integer or half-integer ranging from ½ to 2 (that is, n is 0.5, 1, 1.5, or 2).

In some embodiments of the present application, HA is hydrochloric acid, sulfuric acid, oxalic acid, maleic acid, or malic acid. In some embodiments of the present application, HA is hydrochloric acid, sulfuric acid, or maleic acid. In some embodiments of the present application, HA is hydrochloric acid.

In some embodiments of the present application, HA is hydrochloric acid, sulfuric acid, oxalic acid, or maleic acid, and n is an integer or half-integer ranging from ½ to 2 (that is, n is 0.5, 1, 1.5, or 2); and when HA is hydrochloric acid, n is 0.5, 1.5, or 2. In some embodiments of the present application, n is 1 or 2.

In some embodiments of the present application, the crystalline form of the salt of the arylaminoquinazoline-containing compound, the solvate or hydrate thereof is a crystalline form of a hydrochloride salt of an arylaminoquinazoline-containing compound represented by Formula 3, a solvate or hydrate thereof:

(3)

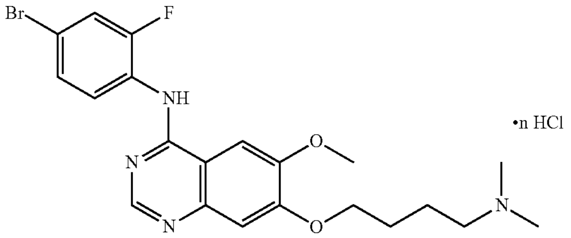

wherein n is 0.5, 1.5 or 2.

In some embodiments of the present application, the crystalline form of the salt of the arylaminoquinazoline-containing compound, the solvate or hydrate thereof is a crystalline form of a dihydrochloride salt represented by Formula 3-1, a solvate or hydrate thereof:

(3-1)

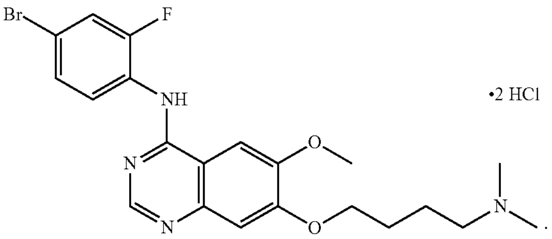

•2 HCl

In some embodiments of the present application, the crystalline form of the dihydrochloride salt represented by Formula 3-1, the solvate or hydrate thereof is selected from one or more of crystalline form I, crystalline form II, crystalline form III, crystalline form IV, crystalline Form V, and crystalline Form VII.

In some embodiments of the present application, the crystalline form I is the crystalline form of the dihydrochloride salt represented by Formula 3-1:

(3-1)

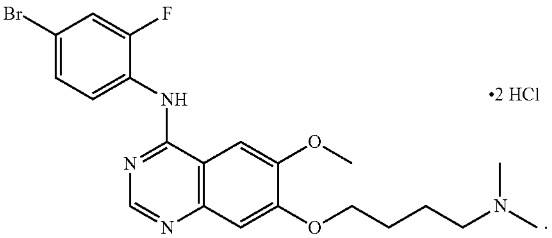

•2 HCl

In some embodiments of the present application, the crystalline form II is the crystalline form of the dihydrochloride salt tetrahydrate represented by Formula 3-2:

(3-2)

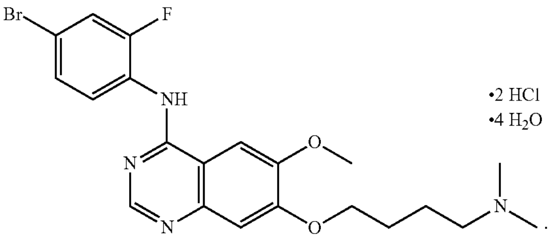

•2 HCl
•4 $H_2O$

In some embodiments of the present application, the crystalline form of the dihydrochloride salt represented by Formula 3-1, the solvate or hydrate thereof (crystalline Form I) has characteristic diffraction peaks at the following 2θ angles (°): 12.4±0.2°, 18.8±0.2°, 20.3±0.2°, and 24.6±0.2° in an X-ray powder diffraction spectrum with Cu-Kα radiation;

or, has characteristic diffraction peaks at the following 2θ angles (°): 9.8±0.2°, 12.4±0.2°, 18.8±0.2°, 20.3±0.2°, and 24.6±0.2° in an X-ray powder diffraction spectrum with Cu-Kα radiation;

or, has characteristic diffraction peaks at the following 2θ angles (°): 8.1±0.2°, 9.8±0.2°, 12.4±0.2°, 18.8±0.2°, 20.3±0.2°, 24.6±0.2°, and 29.9±0.2° in an X-ray powder diffraction spectrum with Cu-Kα radiation;

or, has characteristic diffraction peaks at the following 2θ angles (°): 8.1±0.2°, 9.8±0.2°, 12.4±0.2°, 18.8±0.2°, 19.3±0.2°, 20.3±0.2°, 24.6±0.2°, 28.6±0.2°, and 29.9±0.2° in an X-ray powder diffraction spectrum with Cu-Kα radiation;

or, has characteristic diffraction peaks at the following 2θ angles (°): 8.1±0.2°, 9.8±0.2°, 12.4±0.2°, 16.1±0.2°, 18.8±0.2°, 19.3±0.2°, 20.3±0.2°, 24.6±0.2°, 28.6±0.2°, 29.9±0.2°, and 30.9±0.2° in an X-ray powder diffraction spectrum with Cu-Kα radiation; and preferably, the relative intensities of the above characteristic peaks are as follows:

| Peak Position 2θ angle (°) | Relative Intensity (%) of Peak |
|---|---|
| 8.1 | 3-15 |
| 9.8 | 5-30 |
| 12.4 | 10-30 |
| 16.1 | 2-15 |
| 18.8 | 60-100 |
| 19.3 | 5-20 |
| 20.3 | 8-30 |
| 24.6 | 10-55 |
| 28.6 | 5-20 |
| 29.9 | 5-30 |
| 30.9 | 5-20 |

preferably, the relative intensities of the above characteristic peaks are as follows:

| Peak Position 2θ angle (°) | Relative Intensity (%) of Peak |
|---|---|
| 8.1 | 3-15 |
| 9.8 | 5-20 |
| 12.4 | 10-30 |
| 16.1 | 4-15 |
| 18.8 | 80-100 |
| 19.3 | 5-20 |
| 20.3 | 8-30 |
| 24.6 | 10-40 |
| 28.6 | 5-20 |
| 29.9 | 5-20 |
| 30.9 | 5-20 |

or, the X-ray powder diffraction spectrum with Cu-Kα radiation has diffraction peaks at the following 2θ angles (°):

| Peak Position 2θ angle (°) |
|---|
| 8.1 |
| 9.8 |
| 10.2 |
| 12.4 |
| 15.6 |
| 16.1 |
| 16.8 |
| 18.8 |

-continued

| Peak Position 2θ angle (°) |
|---|
| 19.3 |
| 20.3 |
| 21.7 |
| 22.3 |
| 23.0 |
| 24.6 |
| 25.0 |
| 26.0 |
| 26.1 |
| 27.7 |
| 28.3 |
| 28.6 |
| 29.9 |
| 30.9 |
| 32.3 |
| 34.0 |
| 36.5 |
| 37.7 |

preferably, the relative intensities of the above diffraction peaks are as follows:

| Peak Position 2θ angle (°) | Relative Intensity (%) of Peak |
|---|---|
| 8.1 | 4.2 |
| 9.8 | 10.6 |
| 10.2 | 4.3 |
| 12.4 | 16.5 |
| 15.6 | 3.8 |
| 16.1 | 5.4 |
| 16.8 | 4.3 |
| 18.8 | 100 |
| 19.3 | 8.7 |
| 20.3 | 15.4 |
| 21.7 | 3.7 |
| 22.3 | 4.7 |
| 23.0 | 5.7 |
| 24.6 | 29.7 |
| 25.0 | 14.8 |
| 26.0 | 10.7 |
| 26.1 | 5.2 |
| 27.7 | 4.2 |
| 28.3 | 5.4 |
| 28.6 | 9.0 |
| 29.9 | 8.4 |
| 30.9 | 6.3 |
| 32.3 | 7.5 |
| 34.0 | 3.1 |
| 36.5 | 4.7 |
| 37.7 | 3.9 |

or, the X-ray powder diffraction spectrum with Cu-Kα radiation is substantially as shown in FIG. 1.

In some embodiments of the present application, the crystalline form of the dihydrochloride salt represented by Formula 3-1, the solvate or hydrate thereof (crystalline Form I) has two distinct endothermic peaks in the range of 200-320° C. in a DSC thermogram, of which the onset temperatures occur at 219.1±3° C. and 235.1±3° C., respectively, and the peak values occur at 231.0±3° C. and 284.2±3° C., respectively, as determined using DSC-TGA. The TGA thermogram of the hydrochloride salt shows that decomposition occurs at 205.6±3° C. Alternatively, the crystalline form I of the dihydrochloride salt represented by Formula 3-1 has a DSC-TGA thermogram substantially as shown in FIG. 8.

In some embodiments of the present application, the crystalline form of the dihydrochloride salt represented by Formula 3-1, the solvate or hydrate thereof (crystalline Form I) has a DSC thermogram having endothermic peaks at 231.0±5° C. and 284.2±5° C., respectively.

In some embodiments of the present application, the crystalline form of the dihydrochloride salt represented by Formula 3-1, the solvate or hydrate thereof (crystalline Form I) has a TGA thermogram having decomposition occurring at 205.6±5° C.

Figure 8:
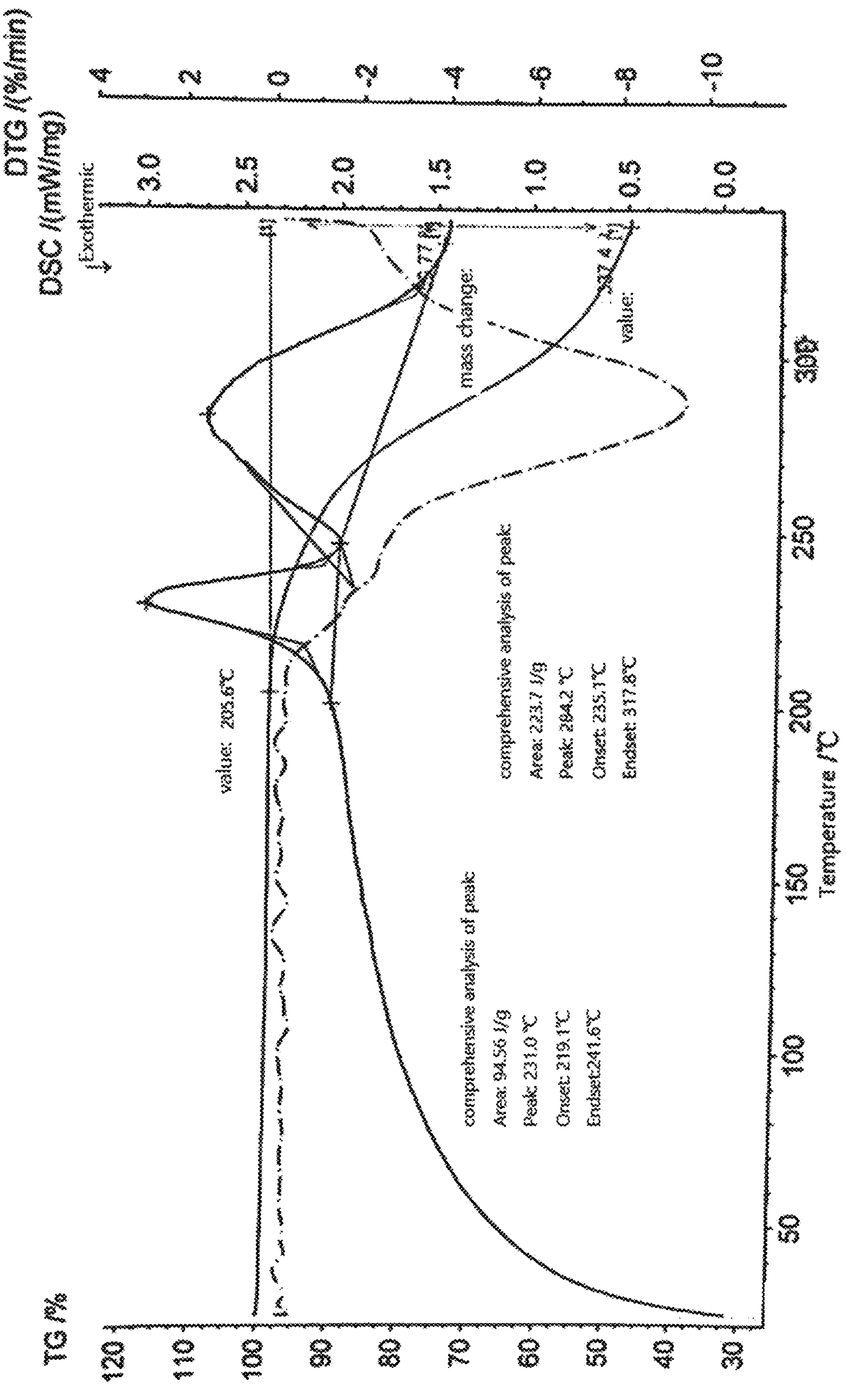
FIG. 8 is a DSC-TGA thermogram of crystalline form I of a dihydrochloride salt of Compound 1, a solvate or hydrate thereof obtained in Example 1.

In some embodiments of the present application, the crystalline form of the dihydrochloride salt represented by Formula 3-1, the solvate or hydrate thereof (crystalline Form I) has a DSC thermogram substantially as shown in FIG. 8.

In some embodiments of the present application, the crystalline form of the dihydrochloride salt represented by Formula 3-1, the solvate or hydrate thereof (crystalline Form I) has a TGA thermogram substantially as shown in FIG. 8.

In some embodiments of the present application, the crystalline form of the dihydrochloride salt represented by Formula 3-1, the solvate or hydrate thereof (crystalline Form II) has characteristic diffraction peaks at the following 2θ angles (°): 6.0±0.2°, 6.8±0.2°, 12.4±0.2°, and 26.0±0.2° in an X-ray powder diffraction spectrum with Cu-Kα radiation;

or, has characteristic diffraction peaks at the following 2θ angles (*): 6.0±0.2°, 6.8±0.2°, 12.4±0.2°, 15.5±0.2°, and 26.0±0.2° in an X-ray powder diffraction spectrum with Cu-Kα radiation;

or, has characteristic diffraction peaks at the following 2θ angles (°): 6.0±0.2°, 6.8±0.2°, 12.4±0.2°, 15.5±0.2°, 25.4±0.2°, and 26.0±0.2° in an X-ray powder diffraction spectrum with Cu-Kα radiation;

or, has characteristic diffraction peaks at the following 2θ angles (°): 6.0±0.2°, 6.8±0.2°, 12.4±0.2°, 15.5±0.2°, 18.0±0.2°, 24.4±0.2°, 25.4±0.2°, and 26.0±0.2° in an X-ray powder diffraction spectrum with Cu-Kα radiation;

or, has characteristic diffraction peaks at the following 2θ angles (°): 6.0±0.2°, 6.8±0.2°, 12.4±0.2°, 15.5±0.2°, 18.0±0.2°, 22.7±0.2°, 24.4±0.2°, 25.4±0.2°, and 26.0±0.2° in an X-ray powder diffraction spectrum with Cu-Kα radiation; and preferably, the relative intensities of the above characteristic peaks are as follows:

| Peak Position 2θ angle (°) | Relative Intensity (%) of Peak |
|---|---|
| 6.0 | 20-100 |
| 6.8 | 70-100 |
| 12.4 | 10-60 |
| 15.5 | 8-30 |
| 18.0 | 5-45 |
| 22.7 | 4-25 |
| 24.4 | 5-30 |
| 25.4 | 5-40 |
| 26.0 | 20-90 |

preferably, the relative intensities of the above characteristic peaks are as follows:

| Peak Position 2θ angle (°) | Relative Intensity (%) of Peak |
|---|---|
| 6.0 | 20-60 |
| 6.8 | 80-100 |
| 12.4 | 10-40 |

-continued

| Peak Position 2θ angle (°) | Relative Intensity (%) of Peak |
|---|---|
| 15.5 | 8-30 |
| 18.0 | 5-30 |
| 22.7 | 5-25 |
| 24.4 | 5-30 |
| 25.4 | 10-40 |
| 26.0 | 20-60 |

preferably, the relative intensities of the above characteristic peaks are as follows:

| Peak Position 2θ angle (°) | Relative Intensity (%) of Peak |
|---|---|
| 6.0 | 36.7 |
| 6.8 | 100.0 |
| 12.4 | 22.1 |
| 15.5 | 17.3 |
| 18.0 | 11.9 |
| 22.7 | 9.1 |
| 24.4 | 14.8 |
| 25.4 | 21.4 |
| 26.0 | 47.8 |

preferably, the relative intensities of the above characteristic peaks are as follows:

| Peak Position 2θ angle (°) | Relative Intensity (%) of Peak |
|---|---|
| 6.0 | 100.0 |
| 6.8 | 81.3 |
| 12.4 | 52.8 |
| 15.5 | 9.5 |
| 18.0 | 38.5 |
| 22.7 | 5.4 |
| 24.4 | 13.0 |
| 25.4 | 10.1 |
| 26.0 | 83.7 |

or, the crystalline form of the dihydrochloride salt represented by Formula 3-1, the solvate or hydrate thereof (crystalline form II) has characteristic diffraction peaks at the following 2θ angles (°): 6.0±0.2°, 6.8±0.2°, 12.4±0.2°, 15.5±0.2°, 18.0±0.2°, 20.5±0.2°, 22.7±0.2°, 24.4±0.2°, 25.4±0.2°, 26.0±0.2°, and 27.5±0.2° in an X-ray powder diffraction spectrum with Cu-Kα radiation;

or, the crystalline form of the dihydrochloride salt represented by Formula 3-1, the solvate or hydrate thereof (crystalline form II) has characteristic diffraction peaks at the following 2θ angles (° in an X-ray powder diffraction spectrum with Cu-Kα radiation:

| Peak Position 2θ angle (°) |
|---|
| 6.0 |
| 6.8 |
| 12.4 |
| 15.5 |
| 17.5 |
| 18.0 |

-continued

Figure 2:
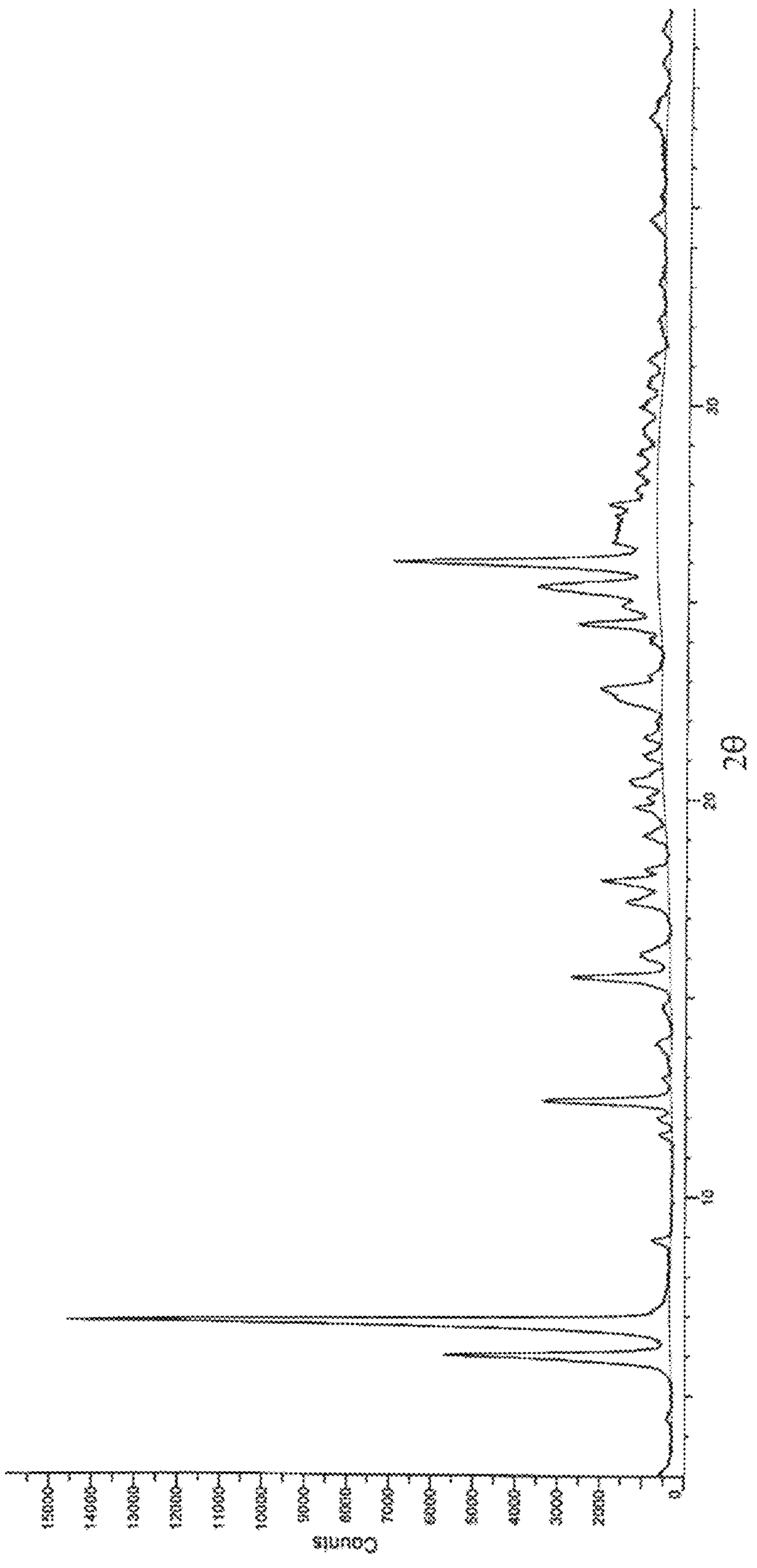
FIG. 2 is an XRPD spectrum of crystalline form II of a dihydrochloride salt of Compound 1, a solvate or hydrate thereof obtained in Example 2.
Figure 19:
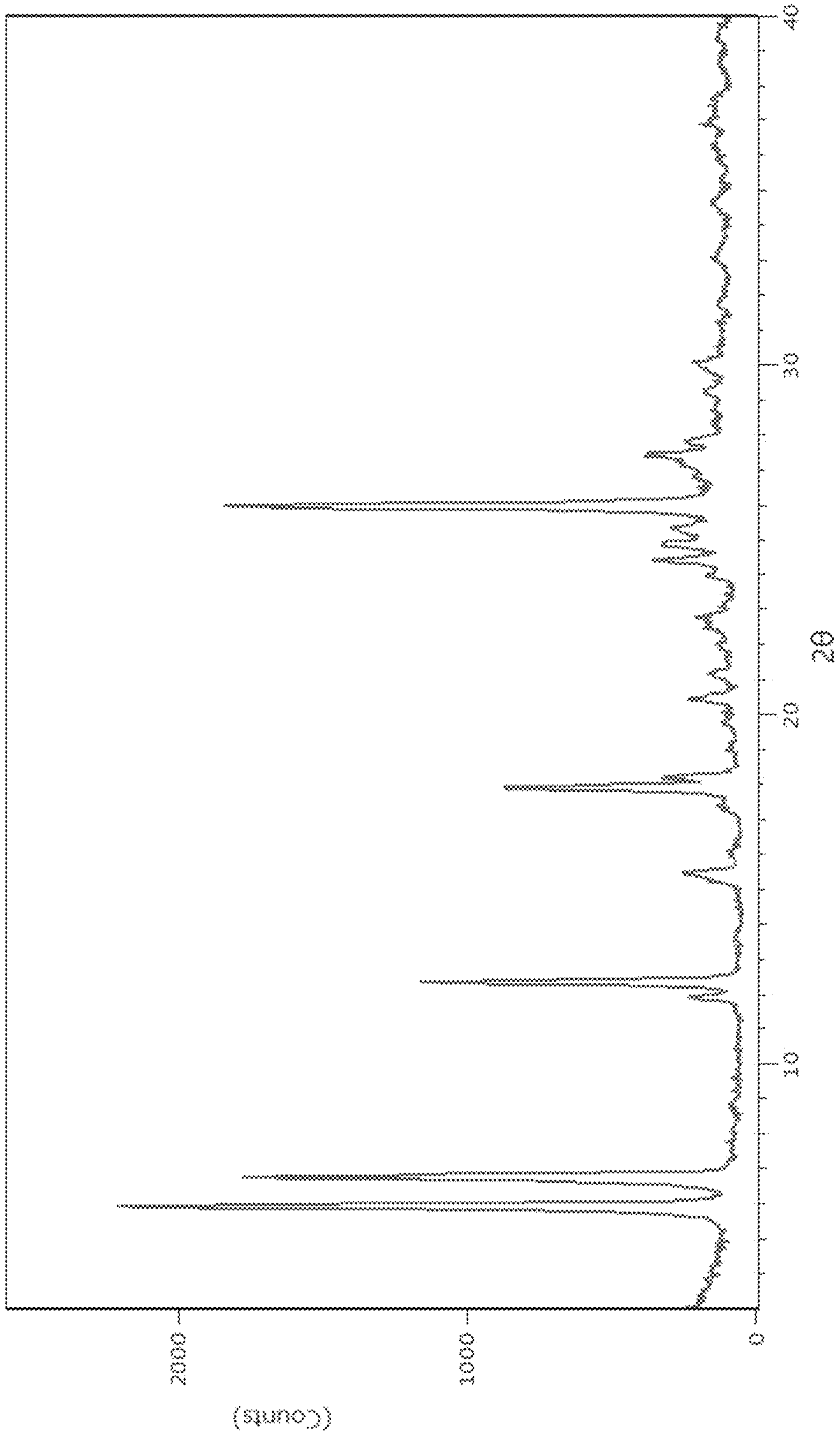
FIG. 19 is an XRPD spectrum of crystalline form II of a dihydrochloride salt of Compound 1, a solvate or hydrate thereof obtained in Example 10.

| Peak Position 2θ angle (°) |
|---|
| 20.5 |
| 22.7 |
| 24.4 |
| 25.4 |
| 26.0 |
| 27.5 |

preferably, the relative intensities of the above diffraction peaks are as follows:

| Peak Position 2θ angle (°) | Relative Intensity (%) of Peak |
|---|---|
| 6.0 | 36.7 |
| 6.8 | 100.0 |
| 12.4 | 22.1 |
| 15.5 | 17.3 |
| 17.5 | 4.2 |
| 18.0 | 11.9 |
| 20.5 | 6.2 |
| 22.7 | 9.1 |
| 24.4 | 14.8 |
| 25.4 | 21.4 |
| 26.0 | 47.8 |
| 27.5 | 8.6 |

preferably, the relative intensities of the above diffraction peaks are as follows:

| Peak Position 2θ angle (°) | Relative Intensity (%) of Peak |
|---|---|
| 6.0 | 100.0 |
| 6.8 | 81.3 |
| 12.4 | 52.8 |
| 15.5 | 9.5 |
| 17.5 | 3.6 |
| 18.0 | 38.5 |
| 20.5 | 7.9 |
| 22.7 | 5.4 |
| 24.4 | 13.0 |
| 25.4 | 10.1 |
| 26.0 | 83.7 |
| 27.5 | 12.8 |

or, the crystalline form of the dihydrochloride salt represented by Formula 3-1, the solvate or hydrate thereof (crystalline form II) has an X-ray powder diffraction spectrum with Cu-Kα radiation substantially as shown in FIG. 2 or FIG. 19.

In some embodiments of the present application, the crystalline form of the dihydrochloride salt represented by Formula 3-1, the solvate or hydrate thereof (crystalline Form II) has a TGA thermogram with a weight loss of 12.24±0.20% in the range of 50-140° C., as determined using TGA.

Figure 9:
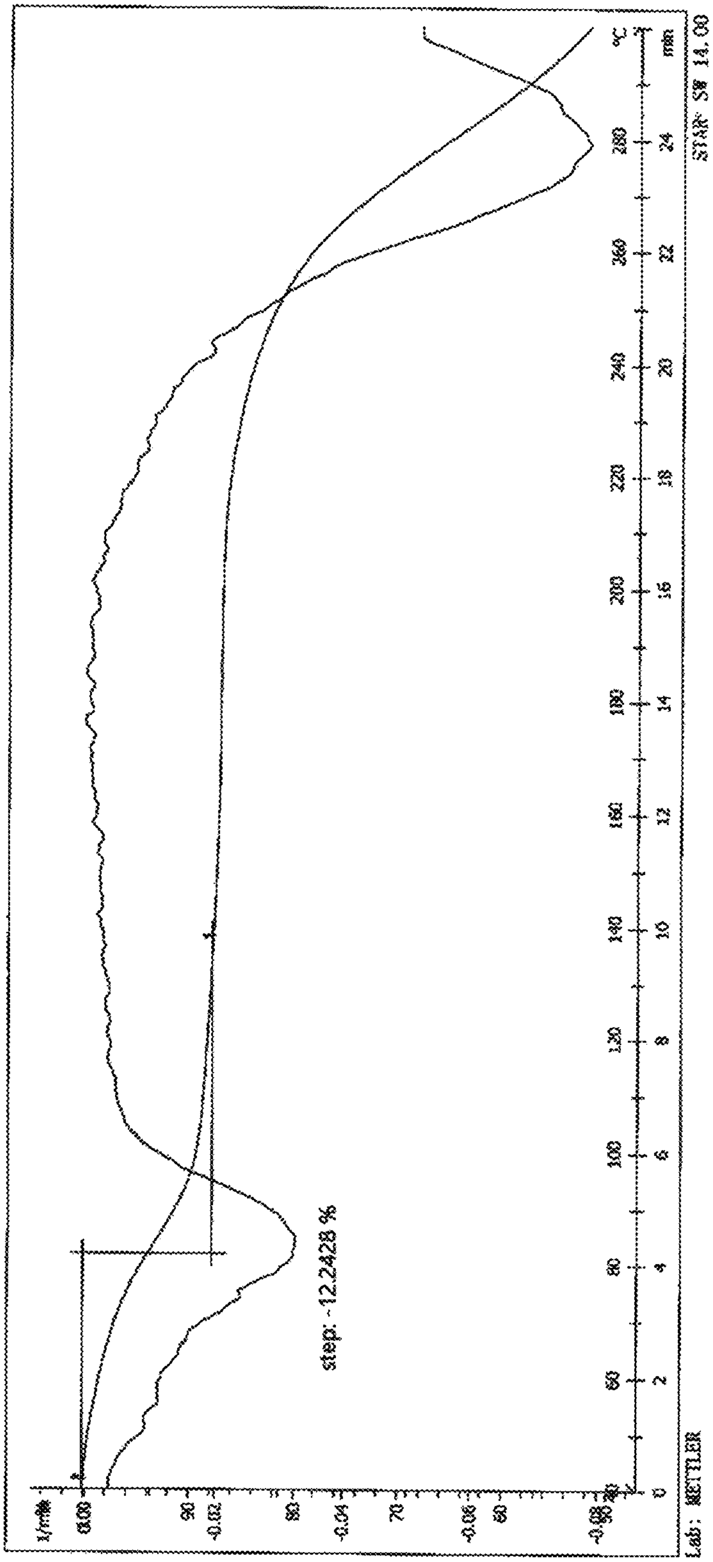
FIG. 9 is a thermogravimetric analysis (TGA) of crystalline form II of a dihydrochloride salt of Compound 1, a solvate or hydrate thereof obtained in Example 2.

Alternatively, the crystalline form of the dihydrochloride salt represented by Formula 3-1, the solvate or hydrate thereof (crystalline form II) has a TGA thermogram substantially as shown in FIG. 9.

Figure 11:
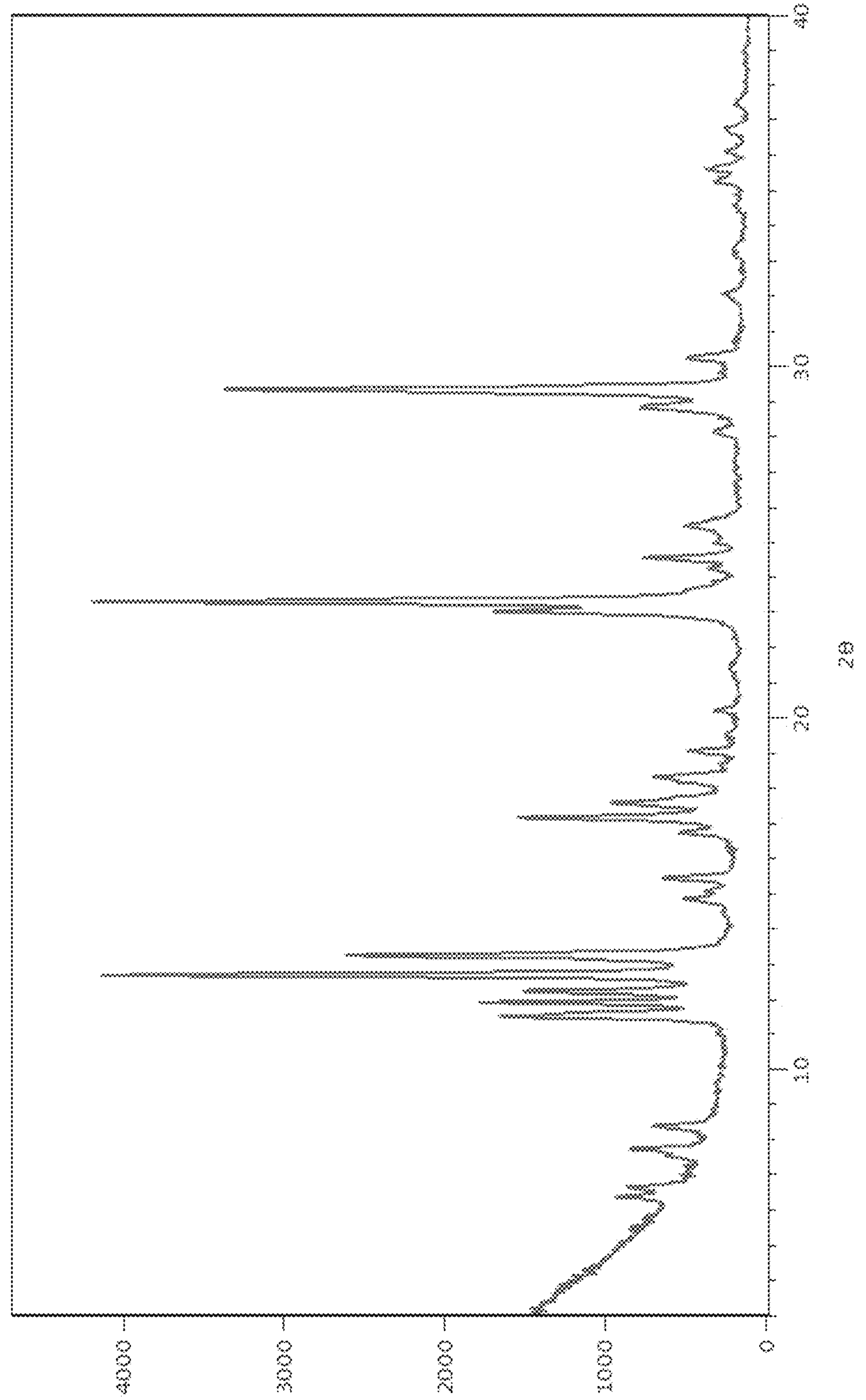
FIG. 11 is an XRPD spectrum of crystalline form III of a dihydrochloride salt of Compound 1, a solvate or hydrate thereof obtained in Example 5.

In some embodiments of the present application, the crystalline form of the dihydrochloride salt represented by Formula 3-1, the solvate or hydrate thereof (crystalline Form III) has characteristic diffraction peaks at the following 2θ angles (°): 12.7±0.2°, 13.3±0.2°, 23.3±0.2°, and 29.3±0.2° in an X-ray powder diffraction spectrum with Cu-Kα radiation;

or, has characteristic diffraction peaks at the following 2θ angles (°): 12.7±0.2°, 13.3±0.2°, 17.2±0.2°, 23.3±0.2°, and 29.3±0.2° in an X-ray powder diffraction spectrum with Cu-Kα radiation;

or, has characteristic diffraction peaks at the following 2θ angles (°): 11.5±0.2°, 11.9±0.2°, 12.7±0.2°, 13.3±0.2°, 17.2±0.2°, 23.3±0.2°, and 29.3±0.2° in an X-ray powder diffraction spectrum with Cu-Kα radiation;

or, has characteristic diffraction peaks at the following 2θ angles (°): 11.5±0.2°, 11.9±0.2°, 12.2±0.2°, 12.7±0.2°, 13.3±0.2°, 17.2±0.2°, 23.3±0.2°, and 29.3±0.2° in an X-ray powder diffraction spectrum with Cu-Kα radiation;

or, has characteristic diffraction peaks at the following 2θ angles (°): 11.5±0.2°, 11.9±0.2°, 12.2±0.2°, 12.7±0.2°, 13.3±0.2°, 17.2±0.2°, 17.6±0.2°, 23.0±0.2°, 23.3±0.2°, and 29.3±0.2° in an X-ray powder diffraction spectrum with Cu-Kα radiation;

or, has characteristic diffraction peaks at the following 2θ angles (°): 8.4±0.2°, 11.5±0.2°, 11.9±0.2°, 12.2±0.2°, 12.7±0.2°, 13.3±0.2°, 17.2±0.2°, 17.6±0.2°, 23.0±0.2°, 23.3±0.2°, 24.6±0.2°, and 29.3±0.2° in an X-ray powder diffraction spectrum with Cu-Kα radiation;

or, has characteristic diffraction peaks at the following 2θ angles (°): 8.4±0.2°, 11.5±0.2°, 11.9±0.2°, 12.2±0.2°, 12.7±0.2°, 13.3±0.2°, 17.2±0.2°, 17.6±0.2°, 23.0±0.2°, 23.3±0.2°, 24.6±0.2°, 28.8±0.2°, and 29.3±0.2° in an X-ray powder diffraction spectrum with Cu-Kα radiation;

or, has characteristic diffraction peaks at the following 2θ angles (° in an X-ray powder diffraction spectrum with Cu-Kα radiation:

| Peak Position 2θ angle (°) |
|---|
| 6.4 |
| 6.6 |
| 7.8 |
| 8.4 |
| 11.5 |
| 11.9 |
| 12.2 |
| 12.7 |
| 13.3 |
| 14.8 |
| 15.4 |
| 16.7 |
| 17.2 |
| 17.6 |
| 18.3 |
| 19.1 |
| 23.0 |
| 23.3 |
| 24.6 |
| 25.5 |
| 28.8 |
| 29.3 |
| 30.2 |
| 35.6 |

or, the X-ray powder diffraction spectrum with Cu-Kα radiation is substantially as shown in FIG. 11.

In some embodiments of the present application, the crystalline form of the dihydrochloride salt represented by Formula 3-1, the solvate or hydrate thereof (crystalline Form III) has a DSC thermogram having endothermic peaks at 101.52±5° C. and 183.70±5° C., respectively, as determined using DSC.

In some embodiments of the present application, the crystalline form of the dihydrochloride salt represented by Formula 3-1, the solvate or hydrate thereof (crystalline Form III) has a TGA thermogram with a weight loss of 6.3±0.20% in the range of room temperature to 120° C., as determined using TGA.

Figure 12:
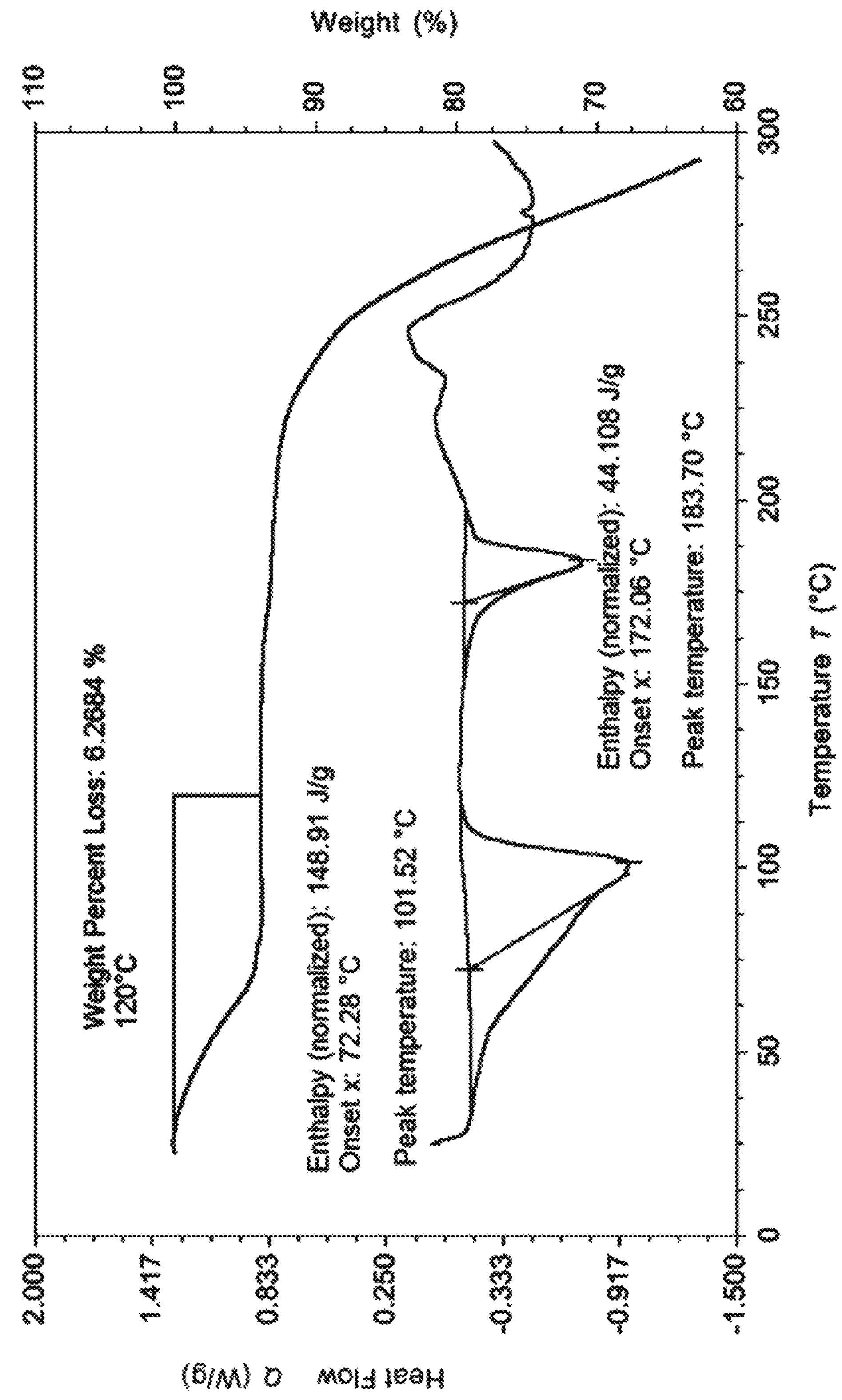
FIG. 12 is a DSC-TGA thermogram of crystalline form III of a dihydrochloride salt of Compound 1, a solvate or hydrate thereof obtained in Example 5.

Alternatively, the crystalline form of the dihydrochloride salt represented by Formula 3-1, the solvate or hydrate thereof (crystalline form III) has a DSC-TGA thermogram substantially as shown in FIG. 12.

Figure 13:
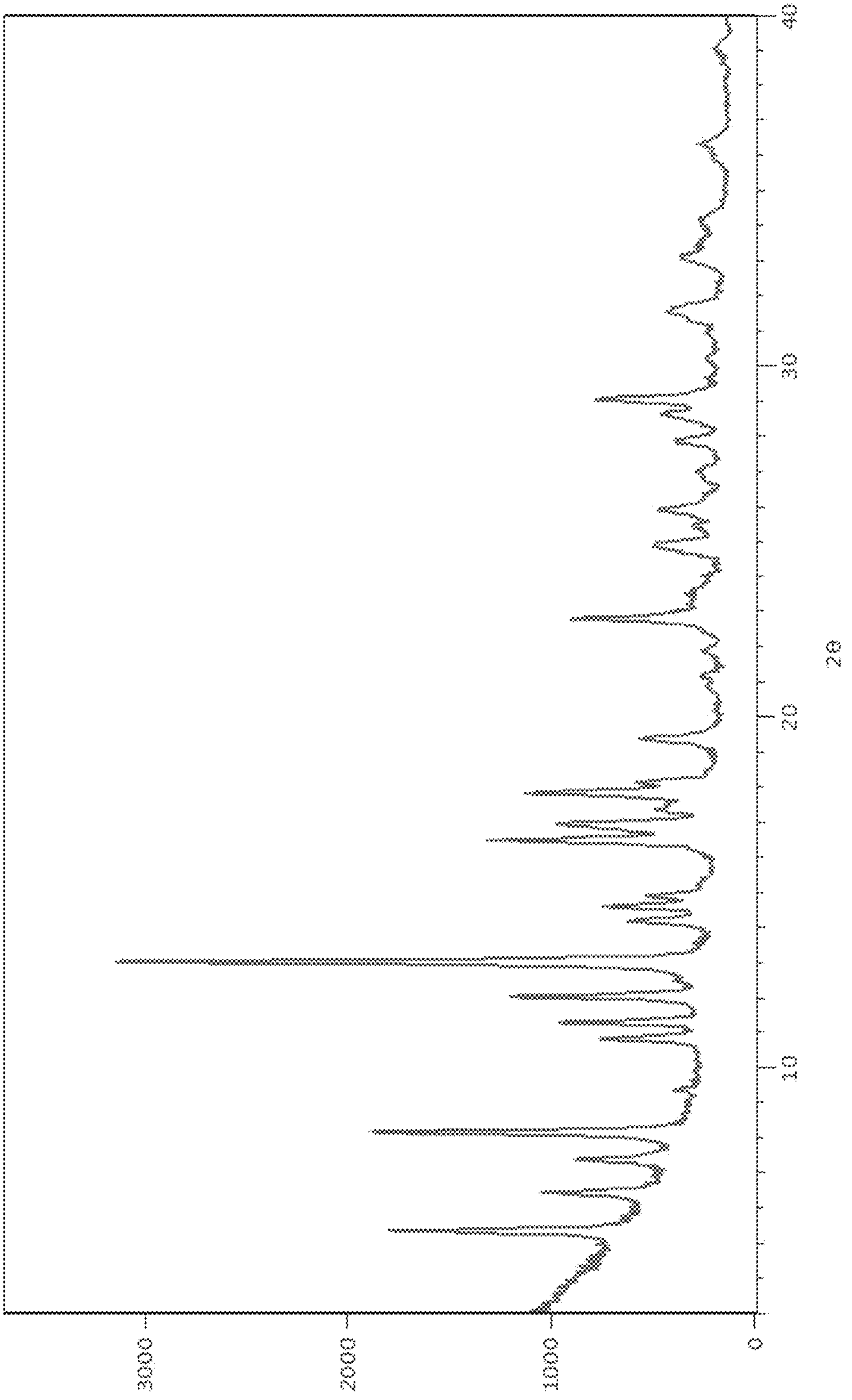
FIG. 13 is an XRPD spectrum of crystalline form IV of a dihydrochloride salt of Compound 1, a solvate or hydrate thereof obtained in Example 6.

In some embodiments of the present application, the crystalline form of the dihydrochloride salt represented by Formula 3-1, the solvate or hydrate thereof (crystalline Form IV) has characteristic diffraction peaks at the following 2θ angles (°): 5.4±0.2°, 8.2±0.2°, 13.0±0.2°, and 16.5±0.2° in an X-ray powder diffraction spectrum with Cu-Kα radiation;

or, has characteristic diffraction peaks at the following 2θ angles (°): 5.4±0.2°, 8.2±0.2°, 12.0±0.2°, 13.0±0.2°, 16.5±0.2°, and 22.8±0.2° in an X-ray powder diffraction spectrum with Cu-Kα radiation;

or, has characteristic diffraction peaks at the following 2θ angles (°): 5.4±0.2°, 8.2±0.2°, 12.0±0.2°, 13.0±0.2°, 16.5±0.2°, 17.8±0.2°, 22.8±0.2°, and 29.0±0.2° in an X-ray powder diffraction spectrum with Cu-Kα radiation;

or, has characteristic diffraction peaks at the following 2θ angles (°): 5.4±0.2°, 8.2±0.2°, 11.3±0.2°, 12.0±0.2°, 13.0±0.2°, 16.5±0.2°, 17.8±0.2°, 19.4±0.2°, 22.8±0.2°, and 29.0±0.2° in an X-ray powder diffraction spectrum with Cu-Kα radiation;

or, has characteristic diffraction peaks at the following 2θ angles (°): 5.4±0.2°, 6.4±0.2°, 7.4±0.2°, 8.2±0.2°, 11.3±0.2°, 12.0±0.2°, 13.0±0.2°, 16.5±0.2°, 17.8±0.2°, 19.4±0.2°, 22.8±0.2°, and 29.0±0.2° in an X-ray powder diffraction spectrum with Cu-Kα radiation;

or, has characteristic diffraction peaks at the following 2θ angles (°): 5.4±0.2°, 6.4±0.2°, 7.4±0.2°, 8.2±0.2°, 10.8±0.2°, 11.3±0.2°, 12.0±0.2°, 13.0±0.2°, 14.6±0.2°, 16.5±0.2°, 17.8±0.2°, 19.4±0.2°, 22.8±0.2°, and 29.0±0.2° in an X-ray powder diffraction spectrum with Cu-Kα radiation;

or, has characteristic diffraction peaks at the following 2θ angles (°): 5.4±0.2°, 6.4±0.2°, 7.4±0.2°, 8.2±0.2°, 10.8±0.2°, 11.3±0.2°, 12.0±0.2°, 13.0±0.2°, 14.2±0.2°, 14.6±0.2°, 16.5±0.2°, 16.9±0.2°, 17.8±0.2°, 19.4±0.2°, 22.8±0.2°, and 29.0±0.2° in an X-ray powder diffraction spectrum with Cu-Kα radiation;

or, has diffraction peaks at the following 2θ angles (° in an X-ray powder diffraction spectrum with Cu-Kα radiation:

| Peak Position 2θ angle (°) | Peak Position 2θ angle (°) | Peak Position 2θ angle (°) | Peak Position 2θ angle (°) | Peak Position 2θ angle (°) |
|---|---|---|---|---|
| 5.4 | 12.0 | 16.9 | 23.6 | 31.5 |
| 6.4 | 13.0 | 17.4 | 24.9 | 33.1 |
| 7.4 | 14.2 | 17.8 | 25.9 | |
| 8.2 | 14.6 | 18.1 | 27.9 | |
| 10.8 | 14.9 | 19.4 | 28.6 | |
| 11.3 | 16.5 | 22.8 | 29.0 | |

or, the X-ray powder diffraction spectrum with Cu-Kα radiation is substantially as shown in FIG. 13.

In some embodiments of the present application, the crystalline form of the dihydrochloride salt represented by Formula 3-1, the solvate or hydrate thereof (crystalline Form IV) has a DSC thermogram having endothermic peaks at 68.81±5° C. and 177.55±5° C., respectively, as determined using DSC.

In some embodiments of the present application, the crystalline form of the dihydrochloride salt represented by Formula 3-1, the solvate or hydrate thereof (crystalline Form IV) has a TGA thermogram having a weight loss of 3.9±0.20% in the range of room temperature to 150° C., as determined using TGA.

Figure 14:
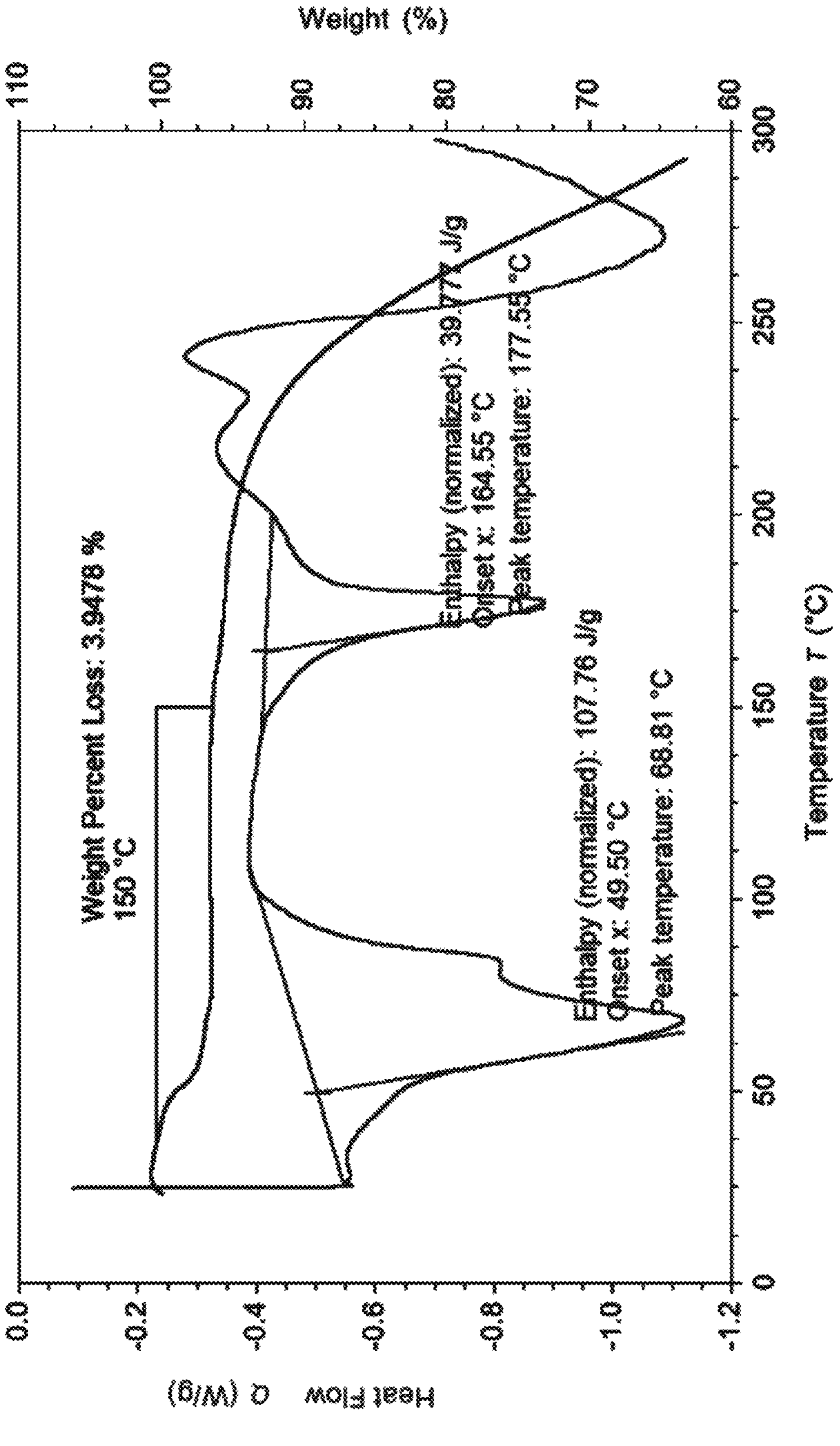
FIG. 14 is a DSC-TGA thermogram of crystalline form IV of a dihydrochloride salt of Compound 1, a solvate or hydrate thereof obtained in Example 6.

Alternatively, the crystalline form of the dihydrochloride salt represented by Formula 3-1, the solvate or hydrate thereof (crystalline form IV) has a DSC-TGA thermogram substantially as shown in FIG. 14.

Figure 15:
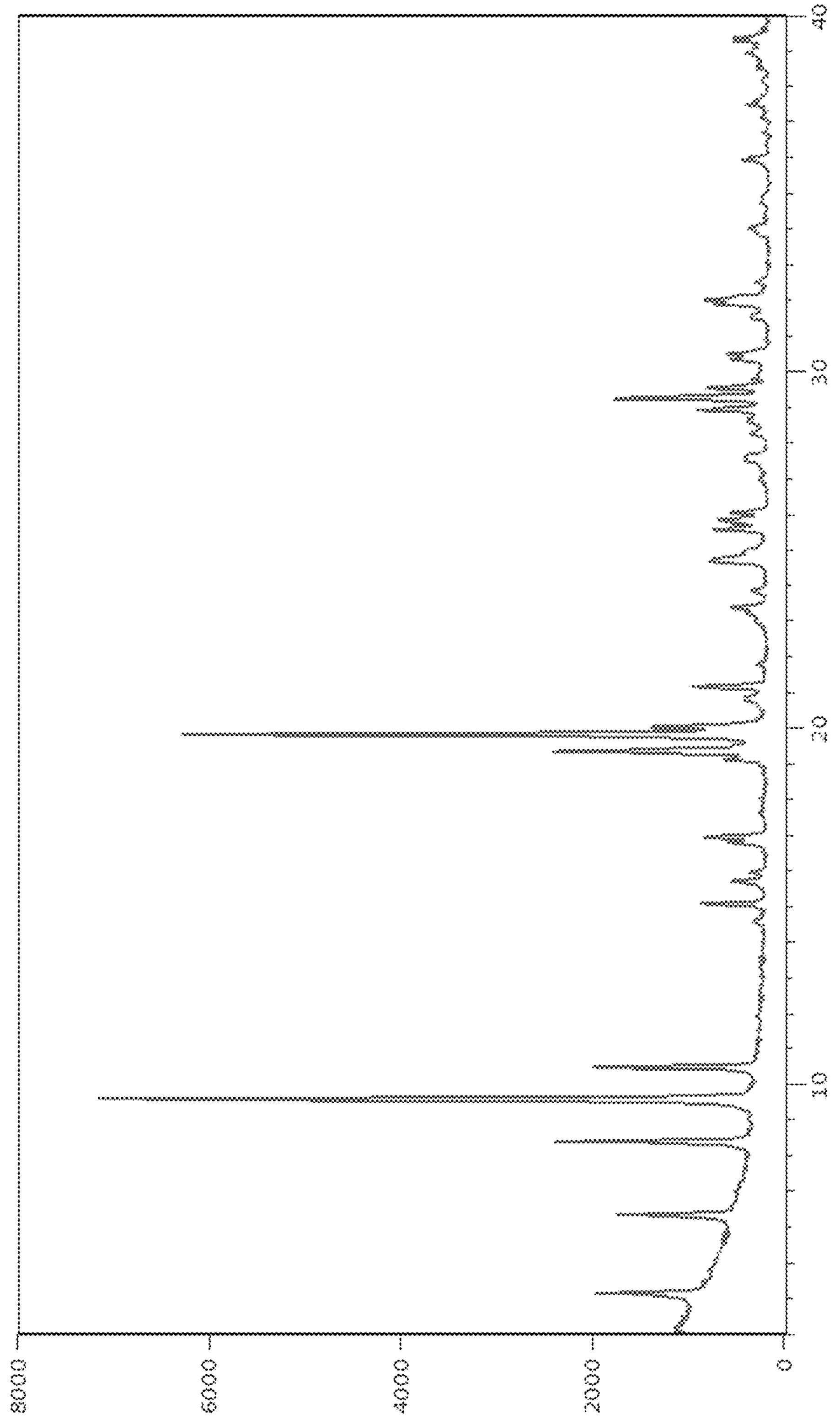
FIG. 15 is an XRPD spectrum of crystalline Form V of a dihydrochloride salt of Compound 1, a solvate or hydrate thereof obtained in Example 7.

In some embodiments of the present application, the crystalline form of the dihydrochloride salt represented by Formula 3-1, the solvate or hydrate thereof (crystalline Form V) has characteristic diffraction peaks at the following 2θ angles (°): 8.4±0.2°, 9.6±0.2°, 19.8±0.2°, and 29.2±0.2° in an X-ray powder diffraction spectrum with Cu-Kα radiation;

or, has characteristic diffraction peaks at the following 2θ angles (°): 8.4±0.2°, 9.6±0.2°, 10.5±0.2°, 19.3±0.2°, 19.8±0.2°, and 29.2±0.2° in an X-ray powder diffraction spectrum with Cu-Kα radiation;

or, has characteristic diffraction peaks at the following 2θ angles (°): 4.2±0.2°, 6.4±0.2°, 8.4±0.2°, 9.6±0.2°, 10.5±0.2°, 19.3±0.2°, 19.8±0.2°, and 29.2±0.2° in an X-ray powder diffraction spectrum with Cu-Kα radiation;

or, has characteristic diffraction peaks at the following 2θ angles (°): 4.2±0.2°, 6.4±0.2°, 8.4±0.2°, 9.6±0.2°, 10.5±0.2°, 15.1±0.2°, 19.3±0.2°, 19.8±0.2°, 21.2±0.2°, and 29.2±0.2° in an X-ray powder diffraction spectrum with Cu-Kα radiation;

or, has characteristic diffraction peaks at the following 2θ angles (°): 4.2±0.2°, 6.4±0.2°, 8.4±0.2°, 9.6±0.2°, 10.5±0.2°, 15.1±0.2°, 16.9±0.2°, 19.3±0.2°, 19.8±0.2°, 21.2±0.2°, 24.6±0.2°, and 29.2±0.2° in an X-ray powder diffraction spectrum with Cu-Kα radiation;

or, has characteristic diffraction peaks at the following 2θ angles (°): 4.2±0.2°, 6.4±0.2°, 8.4±0.2°, 9.6±0.2°, 10.5±0.2°, 15.1±0.2°, 16.9±0.2°, 19.3±0.2°, 19.8±0.2°, 21.2±0.2°, 24.6±0.2°, 28.9±0.2°, 29.2±0.2°, and 29.5±0.2° in an X-ray powder diffraction spectrum with Cu-Kα radiation;

or, has diffraction peaks at the following 2θ angles (° in an X-ray powder diffraction spectrum with Cu-Kα radiation:

| Peak Position 2θ angle (°) | Peak Position 2θ angle (°) | Peak Position 2θ angle (°) | Peak Position 2θ angle (°) | Peak Position 2θ angle (°) |
|---|---|---|---|---|
| 4.2 | 16.8 | 21.2 | 28.9 | 32.0 |
| 6.4 | 16.9 | 23.4 | 29.2 | 39.3 |
| 8.4 | 19.1 | 24.6 | 29.5 | 39.4 |
| 9.6 | 19.3 | 25.6 | 30.3 | |
| 10.5 | 19.8 | 25.8 | 30.5 | |
| 15.1 | 20.0 | 26.0 | 31.9 | |

or, the X-ray powder diffraction spectrum with Cu-Kα radiation is substantially as shown in FIG. 15.

In some embodiments of the present application, the crystalline form of the dihydrochloride salt represented by Formula 3-1, the solvate or hydrate thereof (crystalline Form V) has a DSC thermogram having endothermic peaks at 48.29±5° C., 153.99±5° C., and 190.59±5° C., respectively, as determined using DSC.

In some embodiments of the present application, the crystalline form of the dihydrochloride salt represented by Formula 3-1, the solvate or hydrate thereof (crystalline Form V) has a TGA thermogram having a weight loss of 7.3±0.20% in the range of room temperature to 200° C., as determined using TGA.

Figure 16:
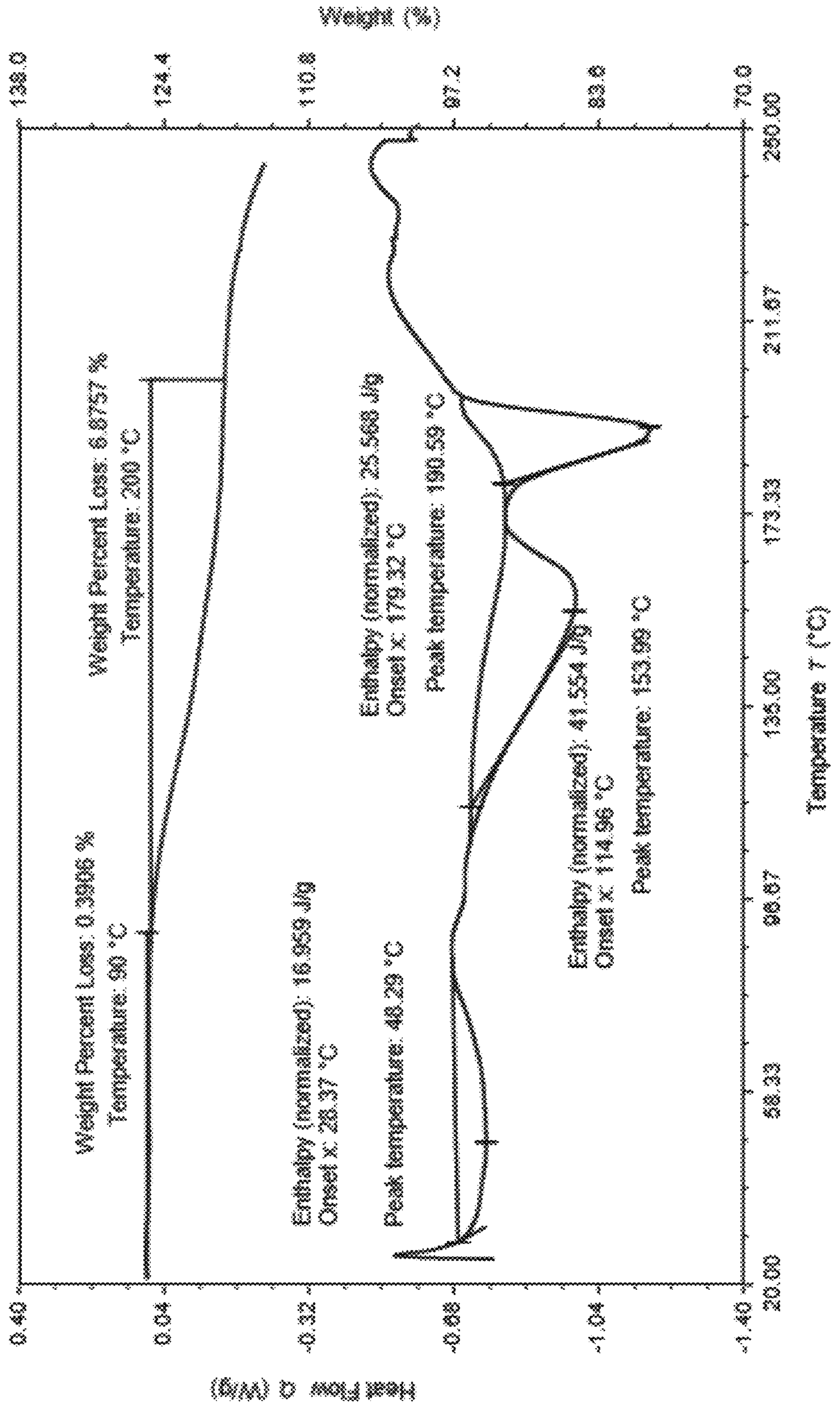
FIG. 16 is a DSC-TGA thermogram of crystalline Form V of a dihydrochloride salt of Compound 1, a solvate or hydrate thereof obtained in Example 7.

Alternatively, the crystalline form of the dihydrochloride salt represented by Formula 3-1, the solvate or hydrate thereof (crystalline Form V) has a DSC-TGA thermogram substantially as shown in FIG. 16.

Figure 17:
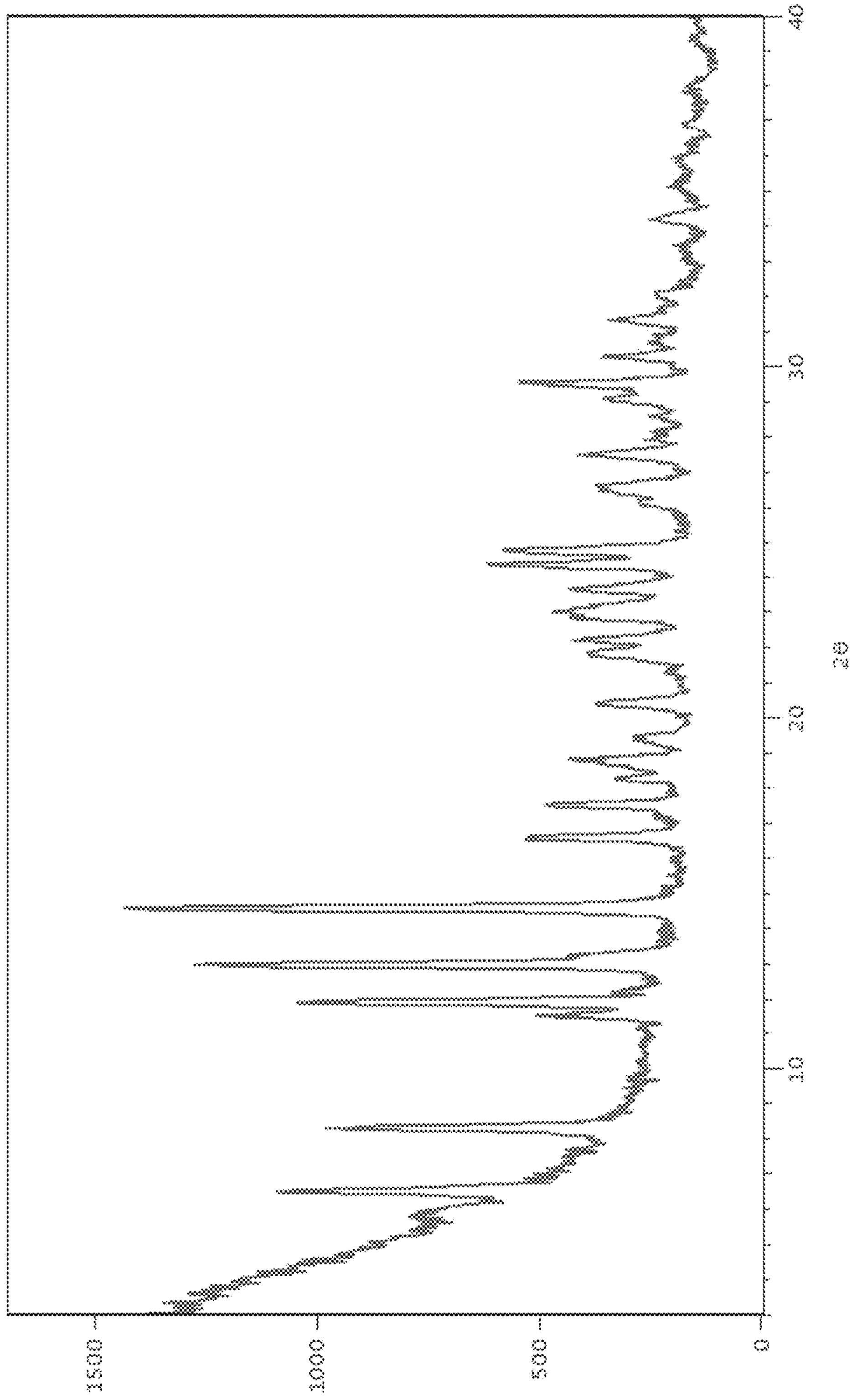
FIG. 17 is an XRPD spectrum of crystalline Form VII of a dihydrochloride salt of Compound 1, a solvate or hydrate thereof obtained in Example 8.

In some embodiments of the present application, the crystalline form of the dihydrochloride salt represented by Formula 3-1, the solvate or hydrate thereof (crystalline Form VII) has characteristic diffraction peaks at the following 2θ angles (°): 8.3±0.2°, 11.9±0.2°, 12.9±0.2°, and 14.6±0.2° in an X-ray powder diffraction spectrum with Cu-Kα radiation;

or, has characteristic diffraction peaks at the following 2θ angles (°): 6.5±0.2°, 8.3±0.2°, 11.9±0.2°, 12.9±0.2°, 14.6±0.2°, and 16.5±0.2° in an X-ray powder diffraction spectrum with Cu-Kα radiation;

or, has characteristic diffraction peaks at the following 2θ angles (°): 6.5±0.2°, 8.3±0.2°, 11.9±0.2°, 12.9±0.2°, 14.6±0.2°, 16.5±0.2°, 17.6±0.2°, and 24.4±0.2° in an X-ray powder diffraction spectrum with Cu-Kα radiation;

or, has characteristic diffraction peaks at the following 2θ angles (°): 6.5±0.2°, 8.3±0.2°, 11.9±0.2°, 12.9±0.2°, 14.6±0.2°, 16.5±0.2°, 17.6±0.2°, 24.4±0.2°, 24.8±0.2°, and 29.6±0.2° in an X-ray powder diffraction spectrum with Cu-Kα radiation;

or, has characteristic diffraction peaks at the following 2θ angles (°): 6.5±0.2°, 8.3±0.2°, 11.9±0.2°, 12.9±0.2°, 14.6±0.2°, 16.5±0.2°, 17.6±0.2°, 18.8±0.2°, 20.4±0.2°, 24.4±0.2°, 24.8±0.2°, and 29.6±0.2° in an X-ray powder diffraction spectrum with Cu-Kα radiation;

or, has characteristic diffraction peaks at the following 2θ angles (°): 6.5±0.2°, 8.3±0.2°, 11.9±0.2°, 12.9±0.2°, 14.6±0.2°, 16.5±0.2°, 17.6±0.2°, 18.8±0.2°, 20.4±0.2°, 22.2±0.2°, 23.6±0.2°, 24.4±0.2°, 24.8±0.2°, and 29.6±0.2° in an X-ray powder diffraction spectrum with Cu-Kα radiation;

or, has diffraction peaks at the following 2θ angles (° in an X-ray powder diffraction spectrum with Cu-Kα radiation:

| Peak Position 2θ angle (°) | Peak Position 2θ angle (°) | Peak Position 2θ angle (°) | Peak Position 2θ angle (°) | Peak Position 2θ angle (°) |
|---|---|---|---|---|
| 6.5 | 14.6 | 20.4 | 24.8 | 29.6 |
| 8.3 | 16.5 | 21.8 | 26.1 | 30.3 |
| 11.5 | 17.6 | 22.2 | 26.6 | 30.7 |
| 11.9 | 18.2 | 22.8 | 27.5 | 31.3 |
| 12.9 | 18.8 | 23.6 | 27.9 | 34.2 |
| 13.2 | 19.5 | 24.4 | 29.1 | |

or, the X-ray powder diffraction spectrum with Cu-Kα radiation is substantially as shown in FIG. 17.

In some embodiments of the present application, the crystalline form of the dihydrochloride salt represented by Formula 3-1, the solvate or hydrate thereof (crystalline Form VII) has a DSC thermogram with endothermic peaks at 87.64±5° C. and 182.15±5° C., respectively, as determined using DSC.

In some embodiments of the present application, the crystalline form of the dihydrochloride salt represented by Formula 3-1, the solvate or hydrate thereof (crystalline Form VII) has a TGA thermogram with a weight loss of 1.4±0.20% in the range of room temperature to 120° C., as determined using TGA.

Figure 18:
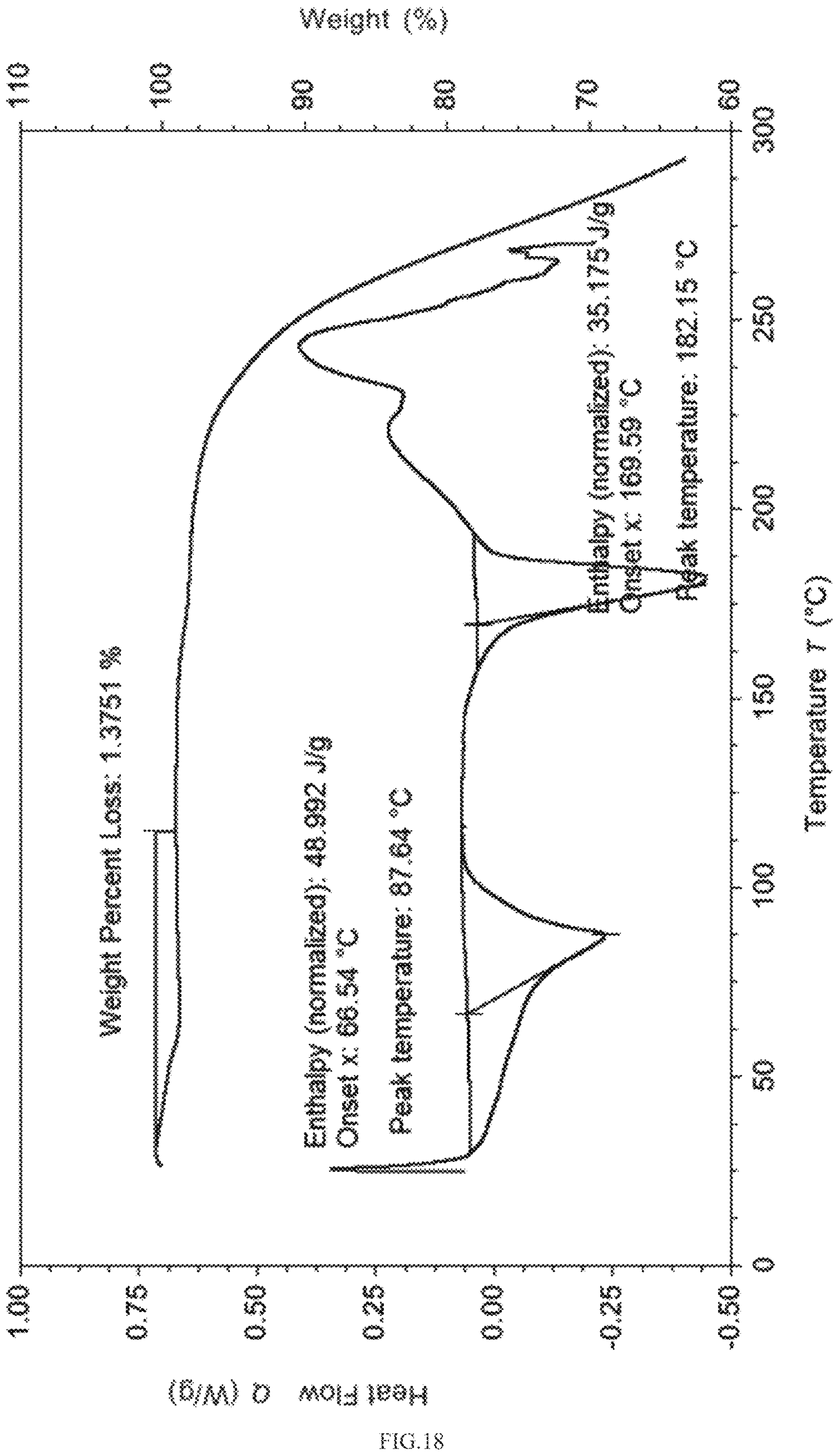
FIG. 18 is a DSC-TGA thermogram of crystalline Form VII of a dihydrochloride salt of Compound 1, a solvate or hydrate thereof obtained in Example 8.

Alternatively, the crystalline form of the dihydrochloride salt represented by Formula 3-1, the solvate or hydrate thereof (crystalline FormVII) has a DSC-TGA thermogram substantially as shown in FIG. 18.

In some embodiments of the present application, the salt of the arylaminoquinazoline-containing compound, the solvate or hydrate thereof is a sulfate salt represented by Formula 4:

(4)

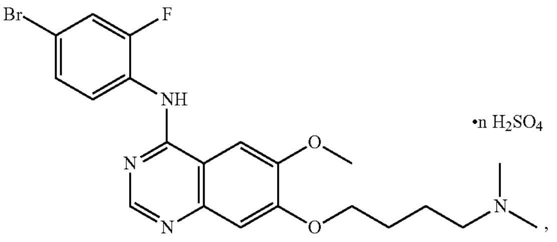

n is an integer or half-integer ranging from 1 to 2 (that is, n is 1, 1.5, or 2).

In some embodiments of the present application, the salt of the arylaminoquinazoline-containing compound is a sulfate salt represented by Formula 4-1:

(4-1)

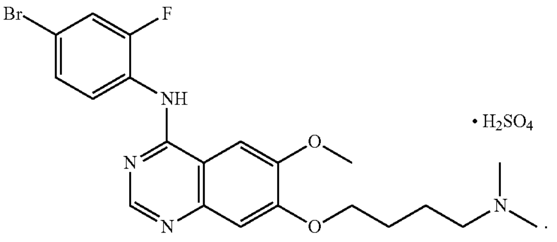

In some embodiments of the present application, the crystalline form of the salt of the arylaminoquinazoline-containing compound, the solvate or hydrate thereof is a crystalline form of the sulfate salt represented by Formula 4, the solvate or hydrate:

(4)

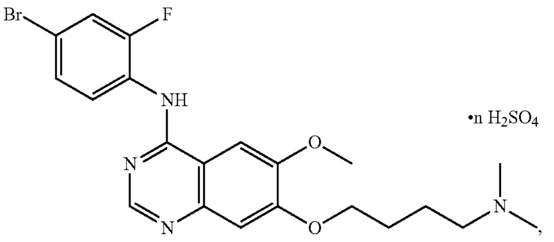

n is an integer or half-integer ranging from 1 to 2 (that is, n is 1, 1.5, or 2).

In some embodiments of the present application, the crystalline form of the salt of the arylaminoquinazoline-containing compound, the solvate or hydrate thereof is a crystalline form of the sulfate salt represented by Formula 4-1, the solvate or hydrate:

(4-1)

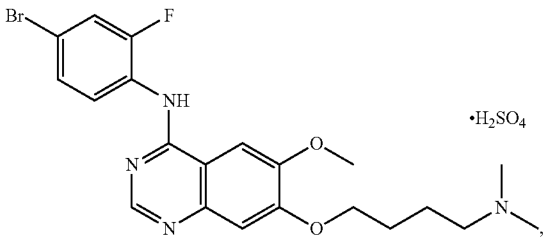

In some embodiments of the present application, the crystalline form of the sulfate salt represented by Formula 4-1, the solvate or hydrate thereof is crystalline form I thereof.

In some embodiments of the present application, the crystalline form of the sulfate salt represented by Formula 4-1, the solvate or hydrate thereof (crystalline form I) has characteristic peaks at the following 2θ angles: 12.4±0.2°, 15.5±0.2°, 24.8±0.2°, and 25.9±0.2° in an X-ray powder diffraction spectrum with Cu-Kα radiation;

or, has characteristic diffraction peaks at the following 2θ angles (°): 6.8±0.2°, 8.5±0.2°, 12.4±0.2°, 15.5±0.2°, 24.8±0.2°, and 25.9±0.2° in an X-ray powder diffraction spectrum with Cu-Kα radiation;

or, has characteristic diffraction peaks at the following 2θ angles (°): 6.8±0.2°, 8.5±0.2°, 12.4±0.2°, 13.6±0.2°, 15.5±0.2°, 24.8±0.2°, and 25.9±0.2° in an X-ray powder diffraction spectrum with Cu-Kα radiation;

or, has characteristic diffraction peaks at the following 2θ angles (*): 6.8±0.2°, 8.5±0.2°, 12.4±0.2°, 13.6±0.2°, 15.5±0.2°, 17.9±0.2°, 19.6±0.2°, 24.8±0.2°, 25.9±0.2° in an X-ray powder diffraction spectrum with Cu-Kα radiation; and preferably, the relative intensities of the above characteristic peaks are as follows:

| Peak Position 2θ angle (°) | Relative Intensity (%) of Peak | Peak Position 2θ angle (°) | Relative Intensity (%) of Peak |
|---|---|---|---|
| 6.8 | 37.8 | 17.9 | 32.1 |
| 8.5 | 19.6 | 19.6 | 21.9 |
| 12.4 | 57.3 | 24.8 | 99.3 |
| 13.6 | 19.9 | 25.9 | 100.0 |
| 15.5 | 32.4 | | |

or, X-ray powder diffraction spectrum expressed in 2θ angles (° using Cu-Kα radiation has diffraction peaks at the following positions:

| Peak Position 2θ angle (°) | Peak Position 2θ angle (°) | Peak Position 2θ angle (°) |
|---|---|---|
| 6.8 | 19.6 | 24.8 |
| 8.5 | 20.7 | 25.9 |

-continued

Figure 3:
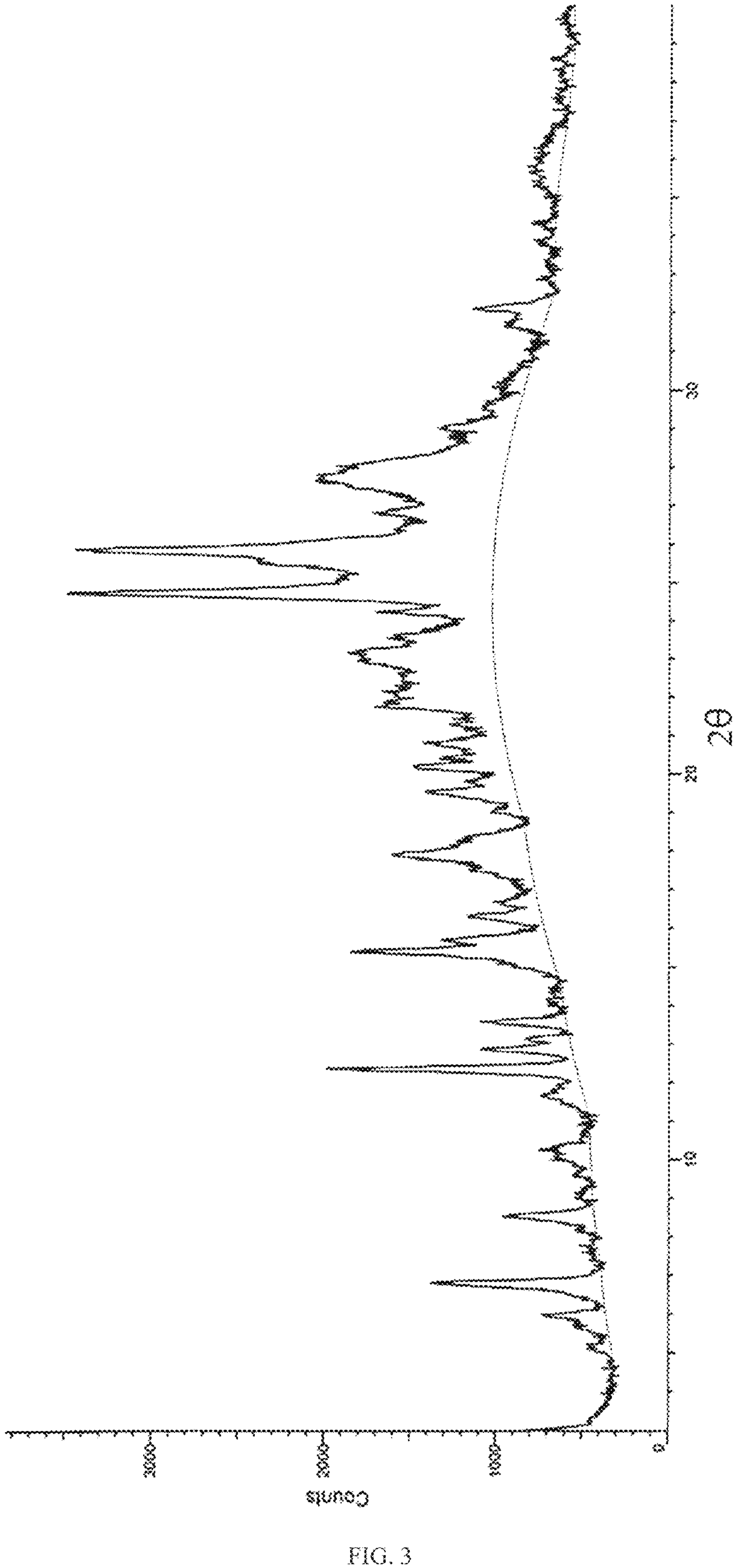
FIG. 3 is an XRPD spectrum of a sulfate salt of Compound 1 obtained in Example 3.

| Peak Position 2θ angle (°) | Peak Position 2θ angle (°) | Peak Position 2θ angle (°) |
|---|---|---|
| 12.4 | 22.1 | 27.8 |
| 13.6 | 23.1 | 28.9 |
| 15.5 | 23.6 | 32.1 |
| 17.9 | | |

preferably, the relative peak intensities of the above diffraction peaks are as follows:

| Peak Position 2θ angle (°) | Relative Intensity (%) of Peak | Peak Position 2θ angle (°) | Relative Intensity (%) of Peak | Peak Position 2θ angle (°) | Relative Intensity (%) of Peak |
|---|---|---|---|---|---|
| 6.8 | 37.8 | 19.6 | 21.9 | 24.8 | 99.3 |
| 8.5 | 19.6 | 20.7 | 13.6 | 25.9 | 100.0 |
| 12.4 | 57.3 | 22.1 | 25.9 | 27.8 | 44.0 |
| 13.6 | 19.9 | 23.1 | 33.2 | 28.9 | 13.9 |
| 15.5 | 32.4 | 23.6 | 22.8 | 32.1 | 22.1 |
| 17.9 | 32.1 | | | | |

or, the X-ray powder diffraction spectrum with Cu-Kα radiation is substantially as shown in FIG. 3.

In some embodiments of the present application, the salt of the arylaminoquinazoline-containing compound, the solvate or hydrate thereof is a maleate salt represented by Formula 5:

(5)

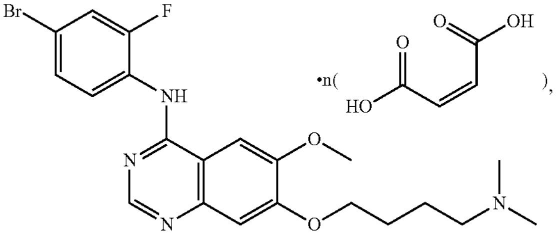

n is an integer or half-integer ranging from 1 to 2 (that is, n is 1, 1.5, or 2).

In some embodiments of the present application, the salt of the arylaminoquinazoline-containing compound is a maleate salt represented by Formula 5-1:

(5-1)

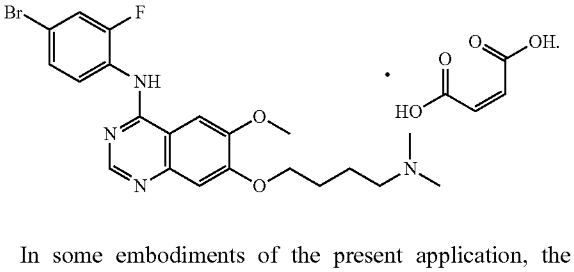

In some embodiments of the present application, the crystalline form of the salt of the arylaminoquinazoline-containing compound, the solvate or hydrate thereof is a crystalline form of the maleate salt represented by Formula 5, the solvate or hydrate thereof:

(5)

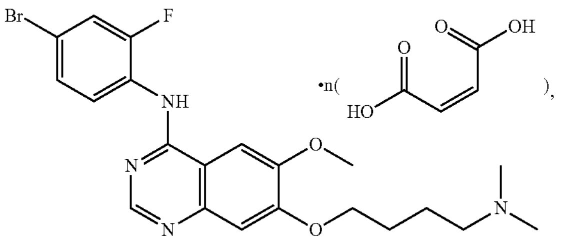

n is an integer or half-integer ranging from 1 to 2 (that is, n is 1, 1.5, or 2).

In some embodiments of the present application, the crystalline form of the salt of the arylaminoquinazoline-containing compound, the solvate or hydrate thereof is a crystalline form of the maleate salt represented by Formula 5-1, the solvate or hydrate thereof:

(5-1)

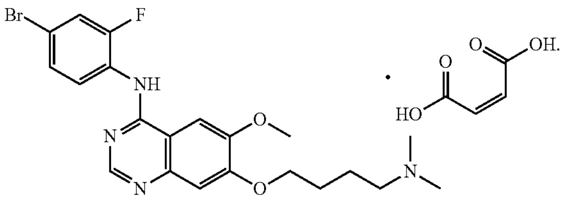

In some embodiments of the present application, the crystalline form of the maleate salt represented by Formula 5-1, the solvate or hydrate thereof is crystalline form I thereof.

Figure 4:
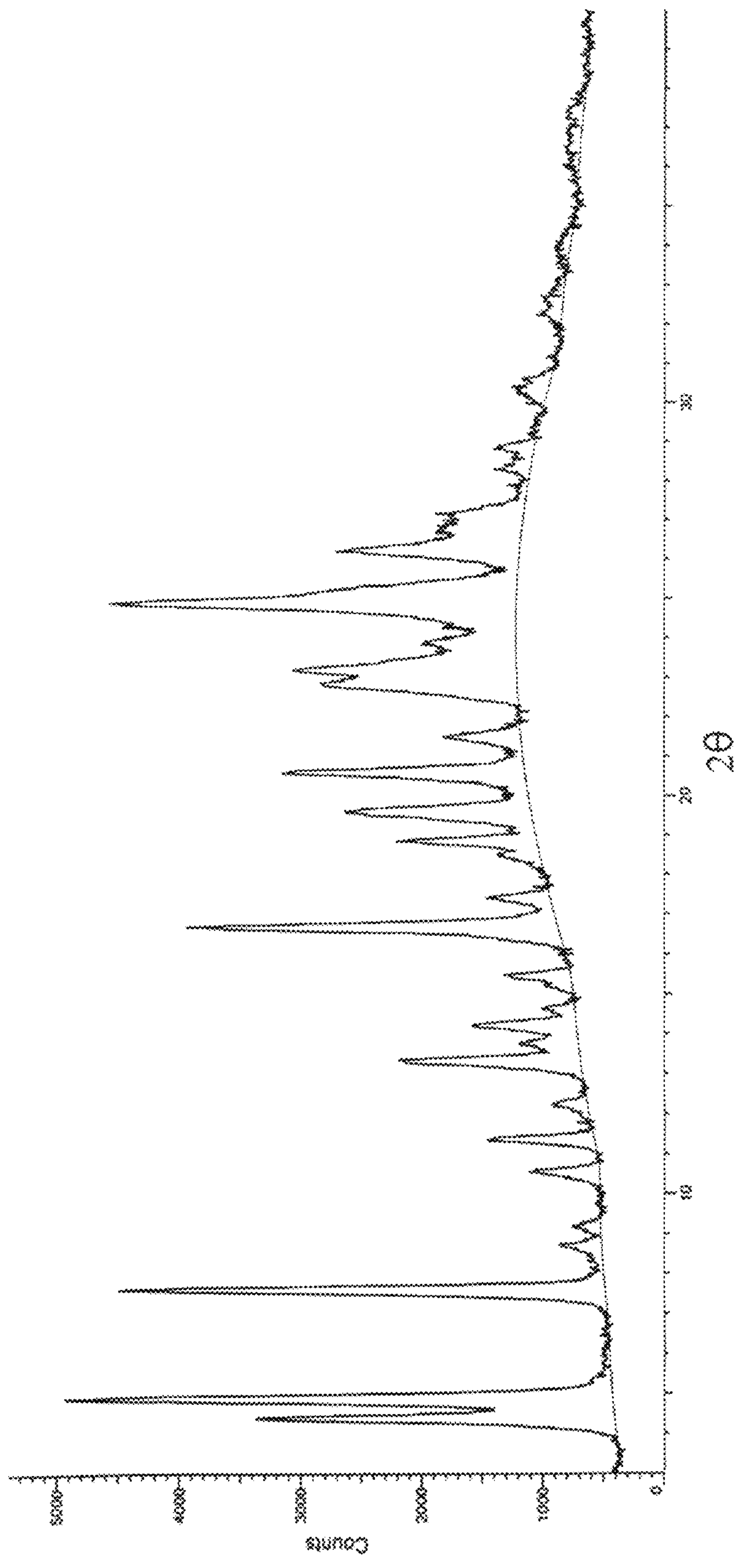
FIG. 4 is an XRPD spectrum of a maleate salt of Compound 1 obtained in Example 4.

In some embodiments of the present application, the crystalline form of the maleate salt represented by Formula 5-1, the solvate or hydrate thereof (crystalline form I) has characteristic peaks at the following 2θ angles (°): 4.9±0.2°, 7.6±0.2°, 16.7±0.2°, and 24.9±0.2° in an X-ray powder diffraction spectrum with Cu-Kα radiation;

or, has characteristic peaks at the following 2θ angles (°): 4.4±0.2°, 4.9±0.2°, 7.6±0.2°, 16.7±0.2°, 20.6±0.2°, and 24.9±0.2° in an X-ray powder diffraction spectrum with Cu-Kα radiation;

or, has characteristic diffraction peaks at the following 2θ angles (°): 4.4±0.2°, 4.9±0.2°, 7.6±0.2°, 13.3±0.2°, 16.7±0.2°, 19.6±0.2°, 20.6±0.2°, 24.9±0.2° in an X-ray powder diffraction spectrum with Cu-Kα radiation;

or, has characteristic diffraction peaks at the following 2θ angles (°): 4.4±0.2°, 4.9±0.2°, 7.6±0.2°, 13.3±0.2°, 16.7±0.2°, 18.9±0.2°, 19.6±0.2°, 20.6±0.2°, 24.9±0.2°, 26.3±0.2° in an X-ray powder diffraction spectrum with Cu-Kα radiation;

or, has characteristic diffraction peaks at the following 2θ angles (°): 4.4±0.2°, 4.9±0.2°, 7.6±0.2°, 11.4±0.2°, 13.3±0.2°, 14.2±0.2°, 16.7±0.2°, 18.9±0.2°, 19.6±0.2°, 20.6±0.2°, 24.9±0.2°, 26.3±0.2° in an X-ray powder diffraction spectrum with Cu-Kα radiation; and preferably, the relative intensities of the above characteristic peaks are as follows:

| Peak Position 2θ angle (°) | Relative Intensity (%) of Peak | Peak Position 2θ angle (°) | Relative Intensity (%) of Peak |
|---|---|---|---|
| 4.4 | 64.6 | 16.7 | 76.8 |
| 4.9 | 100.0 | 18.9 | 29.1 |
| 7.6 | 97.1 | 19.6 | 38.9 |
| 11.4 | 20.1 | 20.6 | 51.0 |
| 13.3 | 36.8 | 24.9 | 82.5 |
| 14.2 | 20.1 | 26.3 | 32.6 |

or, the X-ray powder diffraction pattern expressed in 2θ angles (*) using Cu-Kα radiation has the following diffraction peaks:

| Peak Position 2θ angle (°) | Peak Position 2θ angle (°) | Peak Position 2θ angle (°) |
|---|---|---|
| 4.4 | 14.2 | 20.6 |
| 4.9 | 15.4 | 21.5 |
| 7.6 | 16.7 | 23.2 |
| 10.6 | 17.4 | 24.9 |
| 11.4 | 18.9 | 26.3 |
| 13.3 | 19.6 | 26.9 |

preferably, the relative intensities of the above diffraction peaks are as follows:

| Peak Position 2θ angle (°) | Relative peak intensity % | Peak Position 2θ angle (°) | Relative peak intensity % | Peak Position 2θ angle (°) | Relative peak intensity % |
|---|---|---|---|---|---|
| 4.4 | 64.6 | 14.2 | 20.1 | 20.6 | 51.0 |
| 4.9 | 100.0 | 15.4 | 12.1 | 21.5 | 16.9 |
| 7.6 | 97.1 | 16.7 | 76.8 | 23.2 | 45.3 |
| 10.6 | 14.3 | 17.4 | 13.8 | 24.9 | 82.5 |
| 11.4 | 20.1 | 18.9 | 29.1 | 26.3 | 32.6 |
| 13.3 | 36.8 | 19.6 | 38.9 | 26.9 | 16.6 |

or, the X-ray powder diffraction spectrum with Cu-Kα radiation is substantially as shown in FIG. 4.

In some embodiments of the present application, the salt of the arylaminoquinazoline-containing compound, the solvate or hydrate thereof is an oxalate salt represented by Formula 6:

(6)

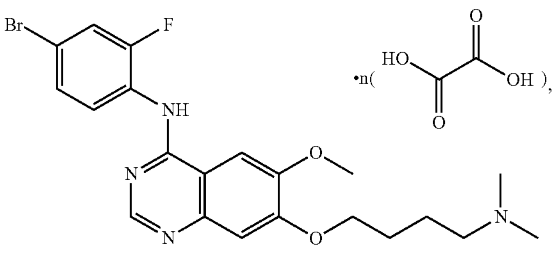

n is an integer or half-integer ranging from 0.5 to 2 (that is, n is 0.5, 1, 1.5, or 2).

In some embodiments of the present application, the salt of the arylaminoquinazoline-containing compound is an oxalate salt represented by Formula 6-1:

(6-1)

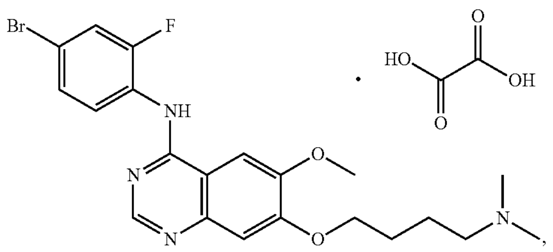

In some embodiments of the present application, the crystalline form of the salt of the arylaminoquinazoline-containing compound, the solvate or hydrate thereof is a crystalline form of the oxalate salt represented by Formula 6, the solvate or hydrate thereof:

(6)

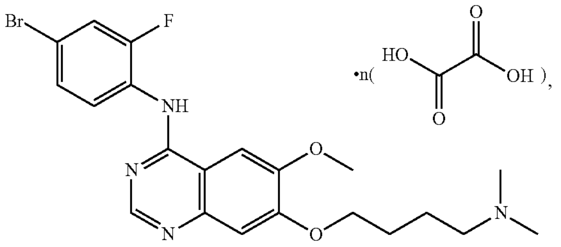

n is an integer or half-integer ranging from 0.5 to 2 (that is, n is 0.5, 1, 1.5, or 2).

In some embodiments of the present application, the crystalline form of the salt of the arylaminoquinazoline-containing compound, the solvate or hydrate thereof is a crystalline form of the oxalate salt represented by Formula 6-1, the solvate or hydrate thereof:

(6-1)

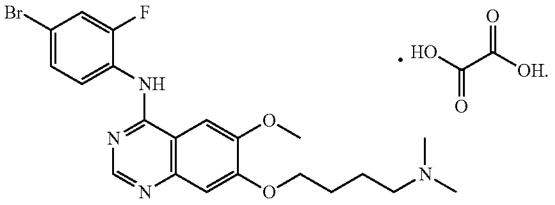

In some embodiments of the present application, the crystalline form of the oxalate salt represented by Formula 6-1, the solvate or hydrate thereof is crystalline form I thereof.

Figure 7:
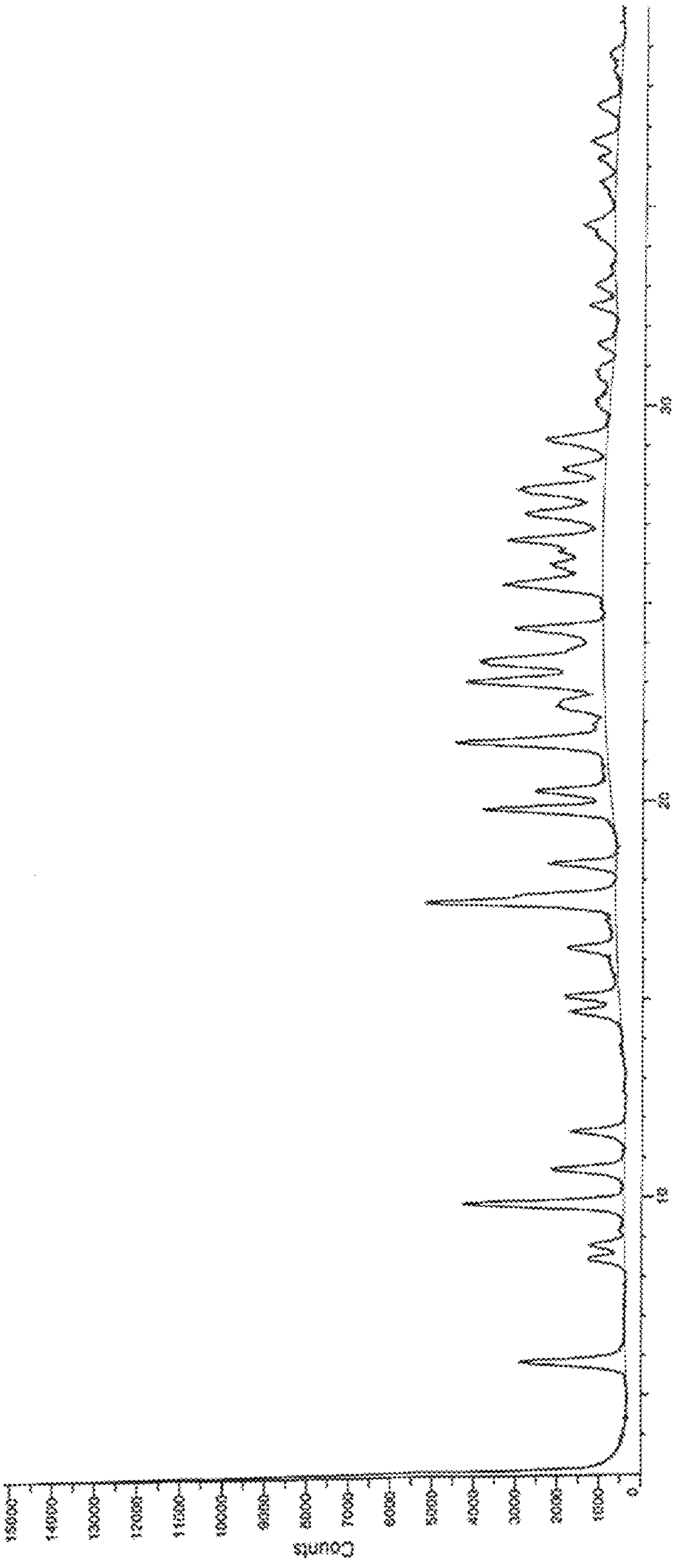
FIG. 7 is an XRPD spectrum of an oxalate salt of Compound 1 obtained in Example 9.

In some embodiments of the present application, the crystalline form of the oxalate salt represented by Formula 6-1, the solvate or hydrate thereof (crystalline form I) has characteristic peaks at the following 2θ angles (°): 5.9±0.2°, 9.9±0.2°, 17.5±0.2°, 21.5±0.2°, and 19.8±0.2° in an X-ray powder diffraction spectrum with Cu-Kα radiation;

or, has characteristic peaks at the following 2θ angles (°): 5.9±0.2°, 9.9±0.2°, 17.5±0.2°, 21.5±0.2°, 19.8±0.2°, 23.0±0.2°, and 25.5±0.2° in an X-ray powder diffraction spectrum with Cu-Kα radiation;

or, has characteristic peaks at the following 2θ angles (°): 5.9±0.2°, 9.9±0.2°, 17.5±0.2°, 18.4±0.2°, 21.5±0.2°, 19.8±0.2°, 23.0±0.2°, 24.4±0.2°, and 25.5±0.2° in an X-ray powder diffraction spectrum with Cu-Kα radiation;

or, has characteristic peaks at the following 2θ angles (°): 5.9±0.2°, 9.9±0.2°, 17.5±0.2°, 18.4±0.2°, 21.5±0.2°, 19.8±0.2°, 23.0±0.2°, 23.5±0.2°, 24.4±0.2°, 25.5±0.2°, and 26.6±0.2° in an X-ray powder diffraction spectrum with Cu-Kα radiation;

or, has characteristic peaks at the following 2θ angles (°): 5.9±0.2°, 9.9±0.2°, 10.7±0.2°, 17.5±0.2°, 18.4±0.2°, 21.5±0.2°, 19.8±0.2°, 23.0±0.2°, 23.5±0.2°, 24.4±0.2°, 25.5±0.2°, 26.6±0.2°, and 27.3±0.2° in an X-ray powder diffraction spectrum with Cu-Kα radiation;

or, has characteristic peaks at the following 2θ angles (°): 5.9±0.2°, 9.9±0.2°, 10.7±0.2°, 17.5±0.2°, 18.4±0.2°, 21.5±0.2°, 19.8±0.2°, 20.3±0.2°, 23.0±0.2°, 23.5±0.2°, 24.4±0.2°, 25.5±0.2°, 26.6±0.2°, 27.3±0.2°, and 27.9±0.2° in an X-ray powder diffraction spectrum with Cu-Kα radiation;

or, has diffraction peaks at the following 2θ angles (° in an X-ray powder diffraction spectrum with Cu-Kα radiation:

| Peak Position 2θ angle (°) | Peak Position 2θ angle (°) | Peak Position 2θ angle (°) |
|---|---|---|
| 5.9 | 18.4 | 25.5 |
| 9.9 | 19.8 | 26.6 |
| 10.7 | 20.3 | 27.3 |
| 11.7 | 21.5 | 27.9 |
| 15.1 | 23.0 | 29.2 |
| 16.3 | 23.5 | |
| 17.5 | 24.4 | |

or, the X-ray powder diffraction spectrum with Cu-Kα radiation is substantially as shown in FIG. 7.

In another aspect, the present application provides a pharmaceutical composition comprising the aforementioned salt of the arylaminoquinazoline-containing compound represented by Formula 2, the solvate or hydrate thereof.

In some embodiments of the present application, the pharmaceutical composition comprises the aforementioned crystalline form of the salt of the arylaminoquinazoline-containing compound represented by Formula 2, the solvate or hydrate thereof.

In some embodiments of the present application, the pharmaceutical composition comprises the aforementioned crystalline form of the dihydrochloride salt of the arylaminoquinazoline-containing compound represented by Formula 3-1, the solvate or hydrate therefore.

In some embodiments of the present application, the pharmaceutical composition comprises one or more of the aforementioned crystalline form I, crystalline form II, crystalline form III, crystalline form IV, crystalline Form V, or crystalline Form VII of the dihydrochloride salt of the arylaminoquinazoline-containing compound represented by Formula 3-1, the solvate or hydrate thereof.

In some embodiments of the present application, the pharmaceutical composition comprises the aforementioned salt of the arylaminoquinazoline-containing compound represented by Formula 2, the solvate or hydrate thereof, and one or more pharmaceutically acceptable carriers.

In some embodiments of the present application, the pharmaceutical composition comprises the aforementioned crystalline form of the salt of the arylaminoquinazoline-containing compound represented by Formula 2, the solvate or hydrate thereof, and one or more pharmaceutically acceptable carriers.

In some embodiments of the present application, the pharmaceutical composition comprises the aforementioned crystalline form of the dihydrochloride salt of the arylaminoquinazoline-containing compound represented by Formula 3-1, the solvate or hydrate therefore, and one or more pharmaceutically acceptable carriers.

In some embodiments of the present application, the pharmaceutical composition comprises one or more of the aforementioned crystalline form I, crystalline form II, crystalline form III, crystalline form IV, crystalline Form V, or crystalline Form VII of the dihydrochloride salt of the arylaminoquinazoline-containing compound represented by Formula 3-1, the solvate or hydrate thereof, and one or more pharmaceutically acceptable carriers.

In some embodiments of the present application, the pharmaceutical composition comprises a therapeutically effective amount of the aforementioned salt of the arylaminoquinazoline-containing compound represented by Formula 2, the solvate or hydrate thereof, and one or more pharmaceutically acceptable carriers.

The pharmaceutical composition of the present application can be prepared by conventional methods in the art, for example, by mixing the salt of the arylaminoquinazoline-containing compound represented by Formula 2, the solvate or hydrate thereof with one or more pharmaceutically acceptable carriers.

In yet another aspect, the present application provides a use of the aforementioned salt of the arylaminoquinazoline-containing compound represented by Formula 2, the solvate or hydrate thereof, or the aforementioned crystalline form of the salt of the arylaminoquinazoline-containing compound represented by Formula 2, the solvate or hydrate thereof, or the aforementioned pharmaceutical composition, in the preparation of a medicament as a receptor tyrosine kinase inhibitor.

In some embodiments of the present application, the receptor tyrosine kinase is one or more of VEGFR, FLT, FGFR, RET, EGFR, and mutants thereof.

In yet another aspect, the present application also provides a use of the aforementioned salt of the arylaminoquinazoline-containing compound represented by Formula 2, the solvate or hydrate thereof, or the aforementioned crystalline form of the salt of the arylaminoquinazoline-containing compound represented by Formula 2, the solvate or hydrate thereof, or the aforementioned pharmaceutical composition, in the treatment of a receptor tyrosine kinase-related disease.

In yet another aspect, the present application also provides a method for treating a receptor tyrosine kinase-related disease in a patient, comprising administering to the patient a therapeutically effective amount of the aforementioned salt of the arylaminoquinazoline-containing compound represented by Formula 2, the solvate or hydrate thereof, or the aforementioned crystalline form of the salt of the arylaminoquinazoline-containing compound represented by Formula 2, the solvate or hydrate thereof, or the aforementioned pharmaceutical composition.

In yet another aspect, the present application also provides the aforementioned salt of the arylaminoquinazoline-containing compound represented by Formula 2, the solvate or hydrate thereof, or the aforementioned crystalline form of the salt of the arylaminoquinazoline-containing compound represented by Formula 2, the solvate or hydrate thereof, or the aforementioned pharmaceutical composition, for use in the treatment of a receptor tyrosine kinase-related disease.

In some embodiments of the present application, the receptor tyrosine kinase-related disease described in the above aspects is a disease caused by one or more of VEGFR, FLT, FGFR, RET, EGFR, and mutants thereof. In some embodiments of the present application, the disease is a cell proliferative disease. In some embodiments of the present application, the disease involves dysregulation of the expression, level, or activity of one or more proteins of VEGFR, FLT, FGFR, RET, and EGFR. In some embodiments of the present application, the cell proliferative disease is a tumor or cancer. In some embodiments of the present application, the tumor includes thyroid cancer, biliary tract cancer, epidermoid cancer, melanoma, colorectal cancer, gastric cancer, esophageal cancer, pancreatic cancer, kidney cancer, liver cancer, lung cancer, or ovarian cancer. In some embodiments of the present application, the thyroid cancer is medullary thyroid cancer and the lung cancer is non-small cell lung cancer. In some embodiments of the present application, the non-small cell lung cancer is RET-fused non-small cell lung cancer.

In yet another aspect, the present application also provides a use of the aforementioned salt of the arylaminoquinazoline-containing compound represented by Formula 2, the solvate or hydrate thereof, or the aforementioned crystalline form of the salt of the arylaminoquinazoline-containing compound represented by Formula 2, the solvate or hydrate thereof, or the aforementioned pharmaceutical composition, in the preparation of an anti-tumor drug.

In yet another aspect, the present application also provides a use of the aforementioned salt of the arylaminoquinazoline-containing compound represented by Formula 2, the solvate or hydrate thereof, or the aforementioned crystalline form of the salt of the arylaminoquinazoline-containing compound represented by Formula 2, the solvate or hydrate thereof, or the aforementioned pharmaceutical composition, in the treatment of a tumor.

In yet another aspect, the present application also provides a method for treating a tumor in a patient, comprising administering to the patient a therapeutically effective amount of the aforementioned salt of the arylaminoquinazoline-containing compound represented by Formula 2, the solvate or hydrate thereof, or the aforementioned crystalline form of the salt of the arylaminoquinazoline-containing compound represented by Formula 2, the solvate or hydrate thereof, or the aforementioned pharmaceutical composition.

In yet another aspect, the present application also provides the aforementioned salt of the arylaminoquinazoline-containing compound represented by Formula 2, the solvate or hydrate thereof, or the aforementioned crystalline form of the salt of the arylaminoquinazoline-containing compound represented by Formula 2, the solvate or hydrate thereof, or the aforementioned pharmaceutical composition, for use in the treatment of a tumor.

In some embodiments of the present application, the tumor or tumor disease described in the above aspects includes thyroid cancer, biliary tract cancer, epidermoid cancer, melanoma, colorectal cancer, gastric cancer, esophageal cancer, pancreatic cancer, kidney cancer, liver cancer, lung cancer, or ovarian cancer. In some embodiments of the present application, the thyroid cancer is medullary thyroid cancer, and the lung cancer is non-small cell lung cancer. In some embodiments of the present application, the non-small cell lung cancer is RET-fused non-small cell lung cancer. In some embodiments of the present application, the tumor or tumor disease is a tumor or tumor disease caused by one or more of VEGFR, FLT, FGFR, RET, EGFR, and mutants thereof. In some embodiments of the present application, the tumor or tumor disease involves dysregulation of the expression, level, or activity of one or more proteins of VEGFR, FLT, FGFR, RET, and EGFR.

The above-mentioned "patient" includes all members of the animalia, including, but not limited to, mammals (e.g., mice, rats, cats, monkeys, dogs, pigs, etc.) and humans.

In yet another aspect, the present application provides a process for the preparation of a salt of an arylaminoquinazoline-containing compound represented by Formula 2, a solvate or hydrate thereof, comprising reacting the arylaminoquinazoline-containing compound represented by Formula 1 with an acid (HA) in a suitable solvent, isolating the salt of the arylaminoquinazoline-containing compound represented by Formula 2, the solvate or hydrate thereof:

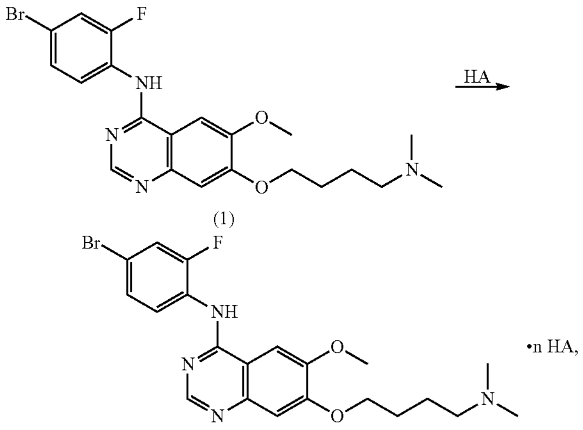

(1)

(2)

wherein,

HA is an acid; and n is an integer or half-integer ranging from ½ to 2.

In some embodiments of the present application, HA is hydrochloric acid, sulfuric acid, oxalic acid, maleic acid, or malic acid.

In some embodiments of the present application, a molar ratio of the arylaminoquinazoline-containing compound represented by Formula 1 to the acid is 1:1~2.5, preferably 1:1~2.

In some embodiments of the present application, the reaction temperature is 10-90° C., preferably 40-70° C.

In some embodiments of the present application, the reaction solvent is selected from one or a combination of two of alcohols, ketones, nitriles, water, or heterocycloalkanes; preferably one or a combination of two of ethyl acetate, methanol, ethanol, water, acetonitrile, acetone, tetrahydrofuran, DMF, NMP, isopropanol, n-propanol, DMA, dioxane; more preferably, ethyl acetate, methanol or water.

In some embodiments of the present application, the reaction solvent is a combination of methanol and ethyl acetate. In some embodiments of the present application, the reaction solvent is water. In some embodiments of the present application, the reaction solvent is a combination of methanol and acetonitrile. In some embodiments of the present application, the reaction solvent is a combination of water and acetonitrile. In some embodiments of the present application, the reaction solvent is ethanol.

In some embodiments of the present application, when the above-mentioned reaction solvent is a combination of two kinds of solvents, they may be added separately. That is, a good solvent is added before a poor solvent is added.

In some embodiments of the present application, the isolation affords the crystalline form of the salt of the arylaminoquinazoline-containing compound represented by Formula 2, the solvate or hydrate.

In some embodiments of the present application, after the reaction is completed, the cooling and crystallization temperatures are −5 to 35° C., preferably 0 to 25° C., and stirring for crystallization is maintained for 0.5 to 24 h, and the solid is isolated and dried to obtain the salt of the arylaminoquinazoline-containing compound represented by Formula 2. Preferably, the temperature for collecting the salt is 10° C., and the crystallization time is 0.5 to 12 h.

In some embodiments of the present application, the isolation step comprises isolating the resulting salt of the arylaminoquinazoline-containing compound represented by Formula 2 from the crystallization solution by using a suitable method, such as filtration, centrifugation, and the like.

In some embodiments of the present application, the drying method can adopt any suitable known method, preferably baking. Specific drying conditions are, for example, the use of a vacuum drying oven, preferably at a temperature of 30 to 65° C., more preferably at a temperature of 40 to 55° C.; and the drying time is preferably 1 to 50 h, more preferably 1 to 16 h, and further preferably 3 to 6 h. No matter what drying method is used, it is preferable that the residual amount of solvent in the obtained product meets the quality standard.

The arylaminoquinazoline-containing compound represented by Formula 1 can be prepared by referring to a method disclosed in the prior art, such as the method described in WO2016023330A1, the content of which is incorporated herein by reference.

DEFINITION AND DESCRIPTION

Unless otherwise specified, the following terms and phrases as used herein are intended to have the following meanings. A particular phrase or term should not be considered indefinite or unclear without a specific definition, but should be understood in the ordinary meaning. When a trade name appears herein, it is intended to refer to the corresponding comerical product or an active ingredient thereof.

The term "solvate" refers to an aggregate or a complex that comprises one or more solvent molecules and the compound represented by Formula 2 of the present application, including an aggregate containing both water molecules and one or more other solvent molecules.

The term "hydrate" refers to an aggregate or a complex that comprises one or more water molecules and the compound represented by Formula 2 of the present application. The hydrate in the present application includes the dihydrochloride salt tetrahydrate of the compound represented by Formula 3-2.

Unless otherwise specified, the "2θ", "2θ angle" or "2θ angles" described in the present application refers to a diffraction angle, of which the unit is "° " or "degree", and the error range of 2θ can be ±0.5, ±0.4, ±0.3, ±0.2 or ±0.1°.

Unless otherwise specified, the unit of the "heating temperature", "cooling temperature" or "crystallization temperature" described in the present application is "° C." or "degree centigrade", and the error range can be ±10, ±5, ±4, ±3, ±2 or ±1° C.

The term "substantially as shown" means that at least 50%, or at least 60%, or at least 70%, or at least 80%, or at least 90%, or at least 95%, or at least 96%, or at least 97%, or at least 98%, or at least 99% of peaks in the X-ray powder diffraction specturm or DSC thermogram or TGA thermogram are shown in the drawings thereof. Further, when the content of a certain crystalline form in a product is gradually reduced, some of diffraction peaks attributed to the crystalline form in the powder X-ray diffraction specturm thereof may be reduced due to the detection sensitivity of an instrument.

The term "characteristic diffraction peak" refers to a diffraction peak that can be used to represent the crystalline form in an X-ray powder diffraction specturm, which is related to the peak position, the peak shape, and the relative peak intensity of the diffraction peak, for example, small angle peaks, sharp peak shape, and diffraction peaks whose the relative peak intensity is at least 3% or more, or at least 5% or more, or at least 10% or more, or at least 20% or more, or at least 30% or more, or at least 40% or more, or at least 50% or more, or at least 60% or more, or at least 70% or more, or at least 75% or more.

The term "cell proliferative disease" refers to a disorder in which the growth rate of a cell population is lower or higher than the expected rate under a given physiological state and condition.

The term "tumor" includes benign tumors, malignant tumors, and borderline tumors, wherein malignant tumors are also collectively referred to as cancers.

The term "treatment" generally refers to obtaining a desired pharmacological and/or physiological effect, including partial or complete stabilization or cure of a disease and/or effects resulting from the disease. "Treatment" as used herein encompasses any treatment of a disease in a patient, including: (a) inhibiting the symptoms of the disease, i.e., arresting its development; or (b) alleviating the symptoms of the disease, i.e., causing regression of the disease or symptoms.

The term "effective amount" or "therapeutically effective amount" means an amount of a compound of the present application that (i) treats a particular disease, or (ii) alleviates, ameliorates or eliminates one or more symptoms of a particular disease. The term "therapeutically effective amount" means an amount of a compound that is sufficient to achieve the treatment of a disease when administered to a patient for the treatment of the disease. The amount of a compound of the present application that constitutes a "therapeutically effective amount" varies depending on the compound, the disease state and its severity, the mode of administration, and the age of a mammal to be treated, but can be routinely determined by those skilled in the art based on their own knowledge and the present application.

The term "pharmaceutically acceptable carrier" or "pharmaceutically acceptable excipient" refers to those carriers that neither significantly irritate to an organism, nor impair the biological activity and performances of an active compound.

The compounds in the present application can be prepared by a variety of synthetic methods well known to those skilled in the art, including specific embodiments as listed below, embodiments formed by their combination with other chemical synthesis methods, and equivalent alternatives well known to those skilled in the art. Preferred embodiments include, but are not limited to, the examples of the present application.

The chemical reactions of the specific embodiments of the present application are carried out in suitable solvents which are adapted to the chemical changes of the present application and the required reagents or materials thereof. In order to obtain the compounds of the present application, it is sometimes necessary for those skilled in the art to modify or select synthesis steps or reaction schemes on the basis of the existing embodiments.

The present application will be described in detail by way of examples, which are not intended to be any limitation to the present application.

All solvents used in the present application are commercially available, and can be used without further purification.

The following abbreviations are used in the present application: DMF: N,N-dimethylformamide; NMP: N-methylpyrrolidone; DMA: N,N-dimethylaniline.

BENEFICIAL EFFECT

The present application provides salts of the arylaminoquinazoline-containing compound represented by Formula 2, the solvate or hydrate thereof, and crystalline forms of salts of the arylaminoquinazoline-containing compound represented by Formula 2, the solvate or hydrate thereof, which have one or more of the following beneficial effects:

The salts of the arylaminoquinazoline-containing compound represented by Formula 2, the solvate or hydrate thereof have good solid properties, and further good crystalline properties. Especially, the dihydrochloride salt, sulfate salt, maleate salt, monohydrochloride salt, oxalate salt, malate salt, and a solvate or hydrate thereof have good crystalline properties.

The solubility of the dihydrochloride salt, sulfate salt, maleate salt, oxalate salt, and a solvate or hydrate thereof in water or an aqueous solution is significantly improved, in particular the dihydrochloride salt, sulfate salt, maleate salt, and a solvate or hydrate thereof.

Furthermore, the preferred salts and crystalline forms thereof (e.g., the dihydrochloride salt, dihydrochloride salt tetrahydrate, sulfate salt, maleate salt, and crystalline forms thereof) have excellent storage stability, chemical stability, thermal stability, and/or mechanical stability.

The salts of the arylaminoquinazoline-containing compound represented by Formula 2, the solvate or hydrate thereof in the present application, particularly the dihydrochloride salt, sulfate salt, maleate salt, oxalate salt, and a solvate or hydrate thereof, and more particularly the dihydrochloride salt and a solvate or hydrate thereof, have better druggability, are suitable for storage as APIs, and can be developed into different pharmaceutical dosage forms according to clinical needs.

EXAMPLES

The technical solutions of the present application will be described in further detail below with reference to specific examples. The following examples merely illustrate and interpret the present application, and should not be construed as limiting the protection scope of the present application. All technologies implemented based on the above contents of the present application are intended to be covered within the protection scope of the present application.

Unless otherwise stated, the starting materials and reagents used in the following examples are commercially available or can be prepared by known methods.

In the following examples, the analysis and detection conditions were as follows:

1. Content

Detection Instrument: Agilent 1260 (LC1260-3-DAD) High Performance Liquid Chromatograph Column: C18 4.6*250 mm, 5 μm Test conditions: Wavelength 252 nm; Column temperature 45° C.;

2. Solubility (Water and pH 2.0 Buffer)

Detection Instrument: Agilent 1260 High Performance Liquid Chromatograph

Detection medium: purified water, pH 2.0 phosphoric acid-disodium hydrogen phosphate buffer Preparation of control solution: it was taken that an appropriate amount of the referen ce substance of the compound of Formula 1, accurately weighed, dissolved completely by solven t and diluted to 100 μg/mL. 10 μL of the prepared solution was accurately measured and the conte nts of Compound 1 were determined by HPLC.

3. X-Ray Powder Diffraction (XRPD)

(1) Detection Instrument: Bruker D2 PHASER powder X-ray diffractometer

Test conditions:

Light tube type: Cu target, ceramic X-ray tube;

X-ray wavelength: CuKα, K (Å): 1.5406;

Voltage and current: 30 kV, 10 mA;

Scanning range: 3~40° 2θ;

Total scanning time: 40 min;

Scanning speed: 0.5 sec/step;

Sample amount: 3 mg (Examples 1-4)

Acquisition software: Diffrac Plus XRD Commander

Analysis software: MDI Jade 6.0

(2) Detection Instrument: Bruker D8 Advance powder X-ray diffractometer

Test conditions:

Light tube type: Cu target, ceramic X-ray tube;

X-ray wavelength: CuKα, K (Å): 1.5418;

Voltage and current: 40 kV, 40 mA;

Scanning range: 3~40° 2θ;

Scanning speed: 0.2 sec/step;

Sample amount: 5-10 mg (Examples 5-8).

4. Thermogravimetric Analysis (TGA)

(1) Detection Instruments: METTLER and SDT Q600 thermogravimetric analyzer

Test Method: 5 mg of a sample (Examples 1 to 4) was weighed and placed in a TGA platinum pot for testing, and the sample was heated from 40° C. to 300° C. at a heating rate of 5K/min under the condition of 40 mL/min of dry nitrogen.

Instrument control software: NETZSCH-*proteus*-6

Analysis software: *Proteus* Analysis (2) Detection instrument: Discovery TGA 55 thermogravimetric analyzer (TA Instruments, US)

Test Method: about 2~5 mg of a sample (Examples 5-8) was placed in a tared open aluminum pan, and the instrument automatically weighed and recorded the weight. The sample was then heated from room temperature to a final temperature in a heating furnace at a heating rate of 10°

C./min. The gas flow was $N_2$ and the flow rates were 40 mL/min (sample chamber) and 25 mL/min (equilibration chamber), respectively.

5. Differential Scanning calorimetry-Thermogravimetric Analysis, (DSC-TGA)

Detection Instrument: NETZSCH STA449F3 Synchronous Thermal Analyzer

Test method: a sample (about 3 mg) was weighed and placed in an aluminum oxide crucible for testing, and the sample was heated from 20° C. to 340° C. at a heating rate of 10K/min under the condition of 20 mL/min of dry nitrogen (protective gas).

Instrument control software: NETZSCH-*proteus*

Analysis software: *Proteus* Analysis

6. Differential Scanning Calorimetry (DSC)

Detection Instrument: Discovery DSC 250 Differential Scanning calorimeter (TA Instruments, US)

Test method: 2~5 mg of a sample (Examples 5-8) was weighed and placed in an airtight aluminum pan with a hole, and the amount of the sample was accurately recorded. The sample was then heated from 25° C. to a final temperature at a rate of 10° C./min. The gas flow was $N_2$ and the flow rate was 50 mL/min.

7. Chloride

Detection Instrument: Dionex ICS-900 ion chromatograph

Column: Dionex Ion Pac AS11-HC anion chromatography column (size: 4×250 mm)

Experimental procedure:

Preparation of a test solution: it was taken that an appropriated amount of a test sampl e, accurately weighed, dissolved by an eluent (12.5 mmol/L sodium hydroxide solution) and then quantitatively diluted to a solution of 0.5 mg per 1 mL. The solution was shaken well and served a s the test solution.

Preparation of a control solution: it was taken that an appropriated amount of sodium chloride (equivalent to 18 mg of chloride ions), accurately weighed, placed in a 250 mL volumetr ic flask, dissolved and diluted to the constant volume by eluents. The solution was shaken well a nd served as the control solution.

Determination method: 10 μL of both of the control solution and the test solution was accurately measured, and injected into an ion chromatograph, and chromatograms were recorded. The chloride ion contents were calculated from the peak areas according to the external standard method.

8. Nuclear Magnetic Hydrogen Spectrum

Instrument Model: Bruker Advance 600 Nuclear Magnetic Resonance Spectrometer

Determination conditions: testing at room temperature (~25° C.) with DMSO-d6 as a solvent 9. Determination of Solubility in Biological Vehicles The preparation procedures of the biological vehicles (SGF, FeSSIF and FaSSIF) used for solubility determination were shown in the following table:

| Vehicle | Preparation procedure |
|---|---|
| SGF | 200 mg of sodium chloride and 0.7 mL of concentrated hydrochloric acid were weighted into a 100 mL volumetric flask, dissolved in water, diluted and made up to volume. The pH of the resulting solution was about 1.20. |
| FaSSIF | 46.8 mg of sodium hydroxide, 450 mg of sodium dihydrogen phosphate dihydrate and 609 mg of sodium chloride were weighed into a 100 mL volumetric flask, dissolved in water and made up to volume. The pH of the resulting solution was about 6.50.<br>44.8 mg of SIF of powder was weighed into a vial, and 20 mL of the above-formulated FaSSIF buffer was added to dissolve. The resulting solution was stirred for 2 hours at room temperature in the dark before use. |
| FeSSIF | 405 mg of sodium hydroxide, 865.4 mg of glacial acetic acid and 1183 mg of sodium chloride were weighed into a 100 mL volumetric flask, dissolved in water and made up to volume. The pH of the resulting solution was about 5.00.<br>224 mg SIF of powder was weighed into a vial, and 20 mL of the above-formulated FeSSIF buffer was added to dissolve. The resulting solution was stirred for 2 hours at room temperature in the dark before use. |

Test method: a sample to be tested was added to a biological vehicles and prepared into a solution or suspension having a target concentration of 10 mg/mL. The resulting solution or suspension was shaken continuously at 200 rpm at 37° C. The suspension was filtered at 0.5 hour and the concentration of the compound in the filtrate was determined by using HPLC.

Example 1

Preparation Example 1: Preparation of Compound 1

(1)

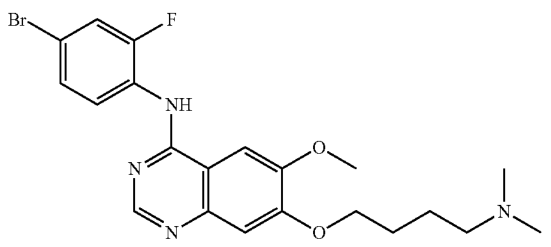

The compound represented by Formula 1 was prepared as a light brown solid with reference to the method described in Example 22 in patent reference WO2016023330A1.

$^1$H-NMR (600 MHz, DMSO-$d_6$δ:9.53 (s, 1H), 8.36 (s, 1H), 7.80 (s, 1H), 7.66 (dd, J=10.2 Hz, J=2.4 Hz, 1H), 7.54 (t, J=8.4 Hz, 1H), 7.47 (dd, J=8.4 Hz, J=2.4 Hz, 1H), 7.19 (s, 1H), 4.15 (t, J=6.6 Hz, 2H), 3.95 (s, 3H), 2.29-2.26 (m, 2H), 2.14 (s, 6H), 1.82-1.79 (m, 2H), 1.59-1.57 (m, 2H).

Preparation of the Dihydrochloride Salt of Compound 1

(3-1)

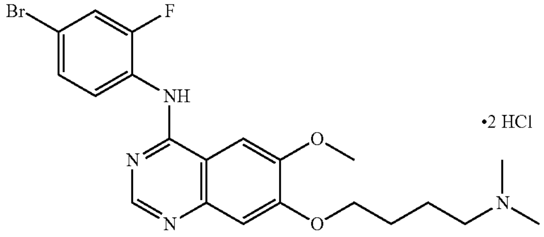

•2 HCl

Compound 1 (10 g, 21.58 mmol) obtained in Preparation Example 1 was weighed into an eggplant-shaped bottle, and methanol (110 mL) was added thereto, heated up to 55±5° C., and stirred until a clear solution was obtained. Hydrochloric acid (3.7 mL, 44.4 mmol) was added dropwise, and stirred for 20 minutes. 200 mL Ethyl acetate was added slowly, cooled to 5±5° C., stirred for 2±1 h, and filtered with suction. The filter cake was washed with ethyl acetate (20 mL) to obtain white dihydrochloride salt (11 g) in a yield of 94.8%.

$^1$H-NMR (600 MHZ, DMSO-$d_6$) δ 15.41 (s, 1H), 11.78 (s, 1H), 10.44 (s, 1H), 8.80 (s, 1H), 8.42 (s, 1H), 7.78 (dd, J=9.6 Hz, J=2.4 Hz, 1H), 7.58-7.52 (m, 2H), 7.47 (s, 1H), 4.24 (t, J=6 Hz, 2H), 4.03 (s, 3H), 3.15-3.14 (m, 2H), 2.76-2.75 (m, 6H), 1.90-1.88 (m, 4H).

The chloride ion content was determined by ion chromatography, and the stoichiometric ratio of the hydrochloride salt was calculated (see table below), and it was deduced that the base/acid ratio of the hydrochloride salt was 1:2.

| Name | Theoretical stoichiometric ratio (Base/acid) | Theoretical chloride ion content (%) | Observed chloride ion content (%) |
|---|---|---|---|
| Example 1 | 1:2 | 13.24% | 13.10% |

The resulting hydrochloride salt sample was subjected to X-ray powder diffraction, which exhibited good crystallinity, and was designated as crystalline form I of the dihydrochloride salt with an XRPD characterization spectrum as shown in FIG. 1 and the main diffraction peak data as shown in Table 1. The sample was subjected to a DSC-TGA test, and had two endothermic peaks. Endothermic peak 1: there was an endothermic peak onset at 219.1° C. and the peak was reached near 231.0° C.; Endothermic peak 2: there was an endothermic peak onset at 235.1° C., and the peak was reached near 284.2° C.; and decomposition occurred at about 205° C. (see FIG. 8). The PLM image showed that the crystalline particles had a regular morphology.

TABLE 1

XRPD diffraction peak data table of Crystalline Form I of the dihydrochloride salt obtained in Example 1

| Peak Position 2θ angle (°) | Relative Intensity (%) of Peak | Relative Intensity (%) of Peak | Relative Intensity (%) of Peak | Peak Position 2θ angle (°) | Relative Intensity (%) of Peak |
|---|---|---|---|---|---|
| 8.117 | 4.2 | 20.302 | 15.4 | 28.628 | 9.0 |
| 9.436 | 2.6 | 21.722 | 3.7 | 29.887 | 8.4 |
| 9.893 | 10.6 | 22.250 | 4.7 | 30.861 | 6.3 |
| 10.240 | 4.3 | 22.960 | 5.7 | 31.617 | 1.8 |
| 12.414 | 16.5 | 24.569 | 29.7 | 32.310 | 7.5 |
| 15.579 | 3.8 | 24.977 | 14.8 | 33.988 | 3.1 |
| 16.111 | 5.4 | 25.404 | 2.8 | 34.988 | 0.9 |
| 16.775 | 4.3 | 26.022 | 10.7 | 36.121 | 0.9 |
| 17.553 | 2.4 | 26.121 | 5.2 | 36.464 | 4.7 |
| 18.304 | 1.8 | 26.929 | 1.5 | 37.732 | 3.9 |
| 18.823 | 100 | 27.697 | 4.2 | | |
| 19.250 | 8.7 | 28.325 | 5.4 | | |

Example 2

Preparation of the Dihydrochloride Salt Tetrahydrate of Compound 1

(3-2)

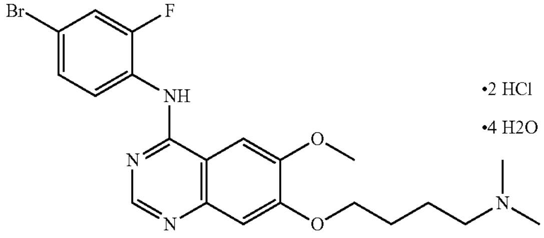

•2 HCl

•4 H2O

Compound 1 (5 g, 10.8 mmol) obtained in Preparation Example 1 was weighed into an eggplant-shaped bottle, purified water (20 mL) was added thereto, and concentrated hydrochloric acid (2.0 mL, 24 mmol) was added dropwise, stirred and heated up to 80±5° C. until completely dissolved. After the dropwise addition was completed, the solution was slowly cooled to room temperature, and filtered with suction, and the filter cake was washed with a small amount of purified water to obtain dihydrochloride salt tetrahydrate (2.82 g) as a white solid in a yield of 43%. It was confirmed by nuclear magnetic hydrogen spectrum that the salt was formed.

The content of the free base was calculated by HPLC (see table below), and it can be deduced that the base/acid ratio of the hydrochloride salt hydrate is 1:2.

| Name | Theoretical stoichiometric ratio (Base/acid/water) | Theoretical content of base (%) | Observed content of base (%) |
|---|---|---|---|
| Example 2 | 1:2:4 | 76.17% | 76.02% |

In addition, the crystalline water content of the hydrochloride salt hydrate in Example 2 was determined by TGA and the weight loss was 12.24%. It can be deduced that the base/crystalline water ratio of the hydrochloride salt hydrate is 1:4, and the TGA test thermogram was shown in FIG. 9.

The resulting dihydrochloride salt tetrahydrate sample was subjected to X-ray powder diffraction, and the resulting solid exhibited good crystallinity, and was designated as crystalline form II with an XRPD characterization spectrum as shown in FIG. 2 and the main diffraction peak data as shown in Table 2.

TABLE 2

XRPD diffraction peak data table of the dihydrochloride salt tetrahydrate crystals obtained in Example 2

| Peak Position 2θ angle (°) | Relative Intensity (%) of Peak | Peak Position 2θ angle (°) | Relative Intensity (%) of Peak | Peak Position 2θ angle (°) | Relative Intensity (%) of Peak |
|---|---|---|---|---|---|
| 4.465 | 0.5 | 19.158 | 2.5 | 28.757 | 3.9 |
| 5.995 | 36.7 | 19.885 | 2.2 | 29.316 | 2.7 |
| 6.842 | 100.0 | 20.484 | 6.2 | 29.989 | 2.9 |
| 8.901 | 3.1 | 21.193 | 2.0 | 30.546 | 1.4 |
| 11.553 | 2.3 | 21.570 | 3.2 | 31.151 | 3.1 |
| 12.405 | 22.1 | 22.694 | 9.1 | 32.157 | 1.5 |
| 13.822 | 2.9 | 24.446 | 14.8 | 33.141 | 1.0 |
| 14.709 | 1.1 | 25.380 | 21.4 | 34.675 | 2.7 |
| 15.510 | 17.3 | 26.006 | 47.8 | 37.298 | 2.8 |
| 16.076 | 4.9 | 26.732 | 7.0 | 38.611 | 1.5 |
| 17.512 | 4.2 | 27.480 | 8.6 | 39.499 | 1.1 |
| 17.958 | 11.9 | 28.320 | 3.4 | | |

Example 3

Preparation of the sulfate salt of Compound 1

(4-1)

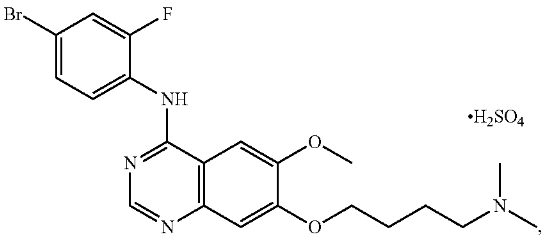

•$H_2SO_4$

Compound 1 (4 g, 8.6 mmol) obtained in Preparation Example 1 was weighed into an eggplant-shaped bottle, and methanol (10 mL) was added thereto, heated up to 60±5° C., and stirred until a clear solution was obtained. 50% Sulfuric acid (1.0 mL, 8.6 mmol) was added dropwise, and stirred for 10 minutes, and 30 mL of ethyl acetate was added slowly. The reaction system was cooled to room temperature and stirred for an additional 1 h, and filtered with suction. The filter cake was washed with ethyl acetate (20 mL) to obtain a white sulfate salt (4.13 g) in a yield of 85.2%. Melting point: 164-168° C. It was confirmed by nuclear magnetic hydrogen spectrum that the salt was formed.

The content of the free base was calculated by HPLC (see table below), and it was deduced that the base/acid ratio of the sulfate salt was 1:1.

| Name | Theoretical stoichiometric ratio (Base/acid) | Theoretical content of base (%) | Observed content of base (%) |
|---|---|---|---|
| Example 3 | 1:1 | 82.53% | 82.82% |

The resulting sulfate salt sample was subjected to X-ray powder diffraction, and the resulting sulfate salt exhibited good crystallinity, and was designated as crystalline form I of the sulfate salt, of which XRPD characterization spectrum was shown in FIG. 3, and the main diffraction peak data were shown in Table 3.

TABLE 3

XRPD diffraction peak data table of crystalline Form I of the sulfate salt obtained in Example 3

| Peak Position 2θ angle (°) | Relative Intensity (%) of Peak |
|---|---|
| 5.213 | 4.2 |
| 5.875 | 5.8 |
| 6.757 | 37.8 |
| 8.544 | 19.6 |
| 10.207 | 7.5 |
| 11.706 | 7.7 |
| 12.359 | 57.3 |
| 12.943 | 8.5 |
| 13.585 | 19.9 |
| 15.478 | 32.4 |
| 16.400 | 8.6 |
| 17.911 | 32.1 |
| 19.559 | 21.9 |
| 20.315 | 9.6 |
| 20.699 | 13.6 |
| 22.063 | 25.9 |
| 22.149 | 27.9 |
| 23.099 | 33.2 |
| 23.640 | 22.8 |
| 24.786 | 99.3 |
| 25.872 | 100.0 |
| 27.829 | 44.0 |
| 28.894 | 13.9 |
| 30.118 | 8.0 |
| 31.761 | 8.3 |
| 32.127 | 22.1 |

Example 4

Preparation of the maleate salt of Compound 1

(5-1)

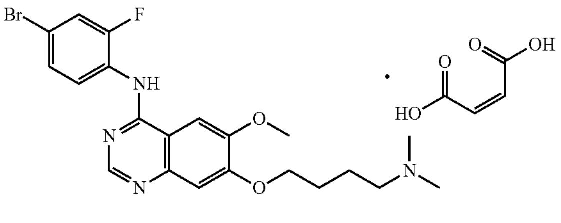

Compound 1 (5 g, 10.8 mmol) obtained in Preparation Example 1, maleic acid (1.5 g, 13.0 mmol) and methanol (10 mL) were weighed and added into a reaction flask, heated to 55±5° C., and stirred until a clear solution was obtained. Ethyl acetate (30 mL) was added thereto, cooled to room temperature, stirred for an additional 2 h, and filtered with suction, and the filter cake was washed with ethyl acetate (30 mL) to obtain white maleate salt (2.22 g) in a yield of 35.5%. Melting point: 138-142° C. It was confirmed by nuclear magnetic hydrogen spectrum that the salt was formed.

The content of the free base was calculated by HPLC (see table below), and it was deduced that the base/acid ratio of the maleate salt was 1:1.

| Name | Theoretical stoichiometric ratio (base/acid) | Theoretical content of base (%) | Observed content of base (%) |
|---|---|---|---|
| Example 4 | 1:1 | 79.97% | 79.12% |

The resulting maleate salt sample was subjected to X-ray powder diffraction, and the resulting maleate salt exhibited good crystallinity, and was designated as crystalline form I of the maleate salt, of which XRPD characterization spectrum was shown in FIG. 4, and the main diffraction peak data were shown in Table 4.

TABLE 4

XRPD diffraction peak data table of crystalline Form I of the maleate salt obtained in Example 4

| Peak Position 2θ angle (°) | Relative Intensity (%) of Peak |
|---|---|
| 4.387 | 64.6 |
| 4.885 | 100.0 |
| 7.583 | 97.1 |
| 8.706 | 8.3 |
| 9.176 | 5.9 |
| 10.555 | 14.3 |
| 11.355 | 20.1 |
| 12.219 | 6.4 |
| 13.326 | 36.8 |
| 14.209 | 20.1 |
| 15.400 | 12.1 |
| 16.702 | 76.8 |
| 17.425 | 13.8 |
| 18.864 | 29.1 |
| 19.589 | 38.9 |
| 20.607 | 51.0 |
| 21.503 | 16.9 |
| 23.210 | 45.3 |
| 24.914 | 82.5 |
| 26.271 | 32.6 |
| 26.858 | 16.6 |
| 28.391 | 3.7 |
| 28.800 | 7.7 |
| 30.363 | 5.4 |
| 32.432 | 2.6 |
| 33.917 | 3.2 |

Example 5

Preparation of the Crystalline Form III of the Dihydrochloride Salt of Compound 1

The sample of Example 1 (about 7 mg) was weighed, dissolved in methanol (0.2 mL), and filtered, and the filtrate was collected. Acetonitrile (1 mL) was then added to the filtrate, stirred overnight, and filtered with suction to obtain a white solid. The resulting solid was subjected to X-ray powder diffraction, which was in crystalline form, and designated as crystalline form III of the dihydrochloride salt, of which an XRPD characterization spectrum was shown in FIG. 11, and the main diffraction peak data were shown in Table 5. The sample was subjected to a DSC-TGA test, and had two endothermic peaks. Endothermic peak 1: there was an endothermic peak onset at 72.28° C. and the peak was reached near 101.52° C.; Endothermic peak 2: there was an endothermic peak onset at 172.06° C., and the peak was reached near 183.70° C. The weight loss was 6.2684% between room temperature and 120° C., and the decomposition occurred at about 225° C. (see FIG. 12).

TABLE 5

XRPD diffraction peak data table of crystalline Form III of the dihydrochloride salt obtained in Example 5

| Peak Position 2θ angle (°) | Relative Intensity (%) of Peak |
|---|---|
| 6.377 | 8.13 |
| 6.648 | 7.62 |
| 7.751 | 10.16 |
| 8.396 | 8.29 |
| 11.500 | 34.78 |
| 11.906 | 37.96 |
| 12.215 | 31.29 |
| 12.696 | 97.33 |
| 13.254 | 59.66 |
| 14.843 | 7.46 |
| 15.444 | 10.84 |
| 16.742 | 8.41 |
| 17.177 | 32.7 |
| 17.576 | 18.47 |
| 18.346 | 12.21 |
| 19.067 | 6.99 |
| 19.515 | 1.68 |
| 20.239 | 3.24 |
| 21.460 | 1.13 |
| 23.025 | 37.92 |
| 23.313 | 100 |
| 24.245 | 4.63 |
| 24.560 | 14.89 |
| 24.987 | 3.84 |
| 25.461 | 8.47 |
| 28.141 | 3.97 |
| 28.806 | 14.74 |
| 29.342 | 79.32 |
| 30.236 | 8.38 |
| 32.050 | 2.86 |
| 33.293 | 1.54 |
| 34.538 | 1.13 |
| 35.258 | 4.7 |
| 35.609 | 5.85 |
| 36.118 | 2.78 |
| 36.750 | 2.9 |
| 37.495 | 1.4 |

Example 6

Preparation of Crystalline Form IV of the Dihydrochloride Salt of Compound 1

The sample of Example 1 (about 7 mg) was weighed, dissolved in water (0.2 mL), and filtered and the filtrate was collected. Acetonitrile (7 mL) was then added to the filtrate, stirred for 24 h, and filtered with suction to obtain a white solid. The resulting solid was subjected to X-ray powder diffraction, which was in crystalline form, and designated as crystalline form IV of the dihydrochloride salt, of which an XRPD characterization spectrum was shown in FIG. 13, and the main diffraction peak data were shown in Table 6. The resulting solid was subjected to DSC-TGA test, and had two endothermic peaks. Endothermic peak 1: there was an endothermic peak onset at 49.50° C. and the peak was reached near 68.81° C.; Endothermic peak 2: there was an endothermic peak onset at 164.55° C., and the peak was reached near 177.55° C. The weight loss was 3.9478% between room temperature and 150° C., and the decomposition occurred at about 215° C. (see FIG. 14).

TABLE 6

XRPD diffraction peak data table of crystalline Form IV of the dihydrochloride salt obtained in Example 6

| Peak Position 2θ angle (°) | Relative Intensity (%) of Peak |
|---|---|
| 5.355 | 39.49 |
| 6.442 | 17.49 |
| 7.373 | 14.63 |
| 8.163 | 51.98 |
| 9.378 | 2.31 |
| 10.833 | 17.07 |
| 11.286 | 24.03 |
| 12.036 | 31.3 |
| 13.022 | 100 |
| 14.177 | 13.39 |
| 14.585 | 17.43 |
| 14.918 | 10.31 |
| 16.484 | 38.23 |
| 16.945 | 26.55 |
| 17.358 | 9.96 |
| 17.834 | 30.95 |
| 18.141 | 13.45 |
| 19.385 | 11.84 |
| 20.870 | 1.91 |
| 21.178 | 3.05 |
| 21.878 | 2.51 |
| 22.799 | 25.09 |
| 23.562 | 5.75 |
| 24.925 | 11.18 |
| 25.459 | 4.6 |
| 25.915 | 10.7 |
| 26.973 | 3.94 |
| 27.873 | 7.9 |
| 28.636 | 9.89 |
| 29.014 | 21.49 |
| 29.672 | 2.51 |
| 30.176 | 2.56 |
| 30.944 | 2.9 |
| 31.531 | 9.55 |
| 33.088 | 7.55 |
| 34.188 | 4.11 |
| 36.335 | 4.58 |
| 39.065 | 2.03 |

Example 7

Preparation of the Dihydrochloride Salt Ethanol Solvate (Crystalline Form V) of Compound 1

The sample of Example 1 (about 30 mg) was weighed, dissolved in ethanol (1 mL), stirred at 50° C. for 30 min and then filtered while hot. The filtrate was cooled to room temperature, stirred for an additional 3 days, and filtered with suction to obtain a white solid. The resulting solid was subjected to X-ray powder diffraction, which was in crystalline form, and designated as crystalline Form V (ethanol solvate, 1:1), of which an XRPD characterization spectrum was shown in FIG. 15, and the main diffraction peak data were shown in Table 7. The resulting solid was subjected to DSC-TGA test, and had three endothermic peaks. Endothermic peak 1: there was an endothermic peak onset at 28.37° C. and the peak was reached near 48.29° C.; Endothermic peak 2: there was an endothermic peak onset at 114.96° C., and the peak was reached near 153.99° C.; and Endothermic peak 3: there was an endothermic peak onset at 179.32° C., and the peak was reached near 190.59° C. The weight loss was 7.2663% between room temperature and 200° C. (see FIG. 16).

TABLE 7

XRPD diffraction peak data table of crystalline Form V obtained in Example 7

| Peak Position 2θ angle (°) | Relative Intensity (%) of Peak |
|---|---|
| 4.157 | 25.07 |
| 6.352 | 22.03 |
| 8.405 | 30.91 |
| 9.600 | 100 |
| 10.493 | 25.93 |
| 14.599 | 1.45 |
| 15.078 | 9.74 |
| 15.707 | 4.97 |
| 15.955 | 2.13 |
| 16.785 | 5.66 |
| 16.944 | 9.2 |
| 19.099 | 6.32 |
| 19.349 | 32.64 |
| 19.822 | 88.21 |
| 20.041 | 17.26 |
| 20.815 | 3.4 |
| 21.162 | 11.38 |
| 21.790 | 1.33 |
| 23.391 | 5.35 |
| 23.853 | 2.37 |
| 24.649 | 7.04 |
| 25.569 | 8.13 |
| 25.843 | 7.35 |
| 26.041 | 5.5 |
| 27.567 | 3.42 |
| 28.276 | 2.16 |
| 28.621 | 3.05 |
| 28.920 | 10.76 |
| 29.244 | 23.68 |
| 29.542 | 9.29 |
| 30.343 | 5.45 |
| 30.510 | 6.12 |
| 31.551 | 2.31 |
| 31.884 | 7.92 |
| 32.007 | 9.92 |
| 32.524 | 1.65 |
| 34.036 | 2.71 |
| 34.834 | 0.97 |
| 35.931 | 4.06 |
| 36.728 | 0.79 |
| 37.152 | 1.08 |
| 37.469 | 3.04 |
| 38.162 | 0.96 |
| 38.950 | 3.26 |
| 39.269 | 5.01 |
| 39.385 | 5.22 |

Example 8

Preparation of Crystalline Form VII of the Dihydrochloride Salt of Compound 1

The sample of crystalline form III obtained in Example 5 was heated to 130° C. and collected to obtain a white solid. The resulting solid was subjected to X-ray powder diffraction, which was in crystalline form, and designated as crystalline Form VII of the dihydrochloride salt, of which an XRPD characterization spectrum was shown in FIG. 17, and the main diffraction peak data were shown in Table 8. The resulting solid was subjected to DSC-TGA test, and had two endothermic peaks. Endothermic peak 1: there was an endothermic peak onset at 66.54° C. and the peak was reached near 87.64° C.; Endothermic peak 2: there was an endothermic peak onset at 169.59° C., and the peak was reached near 182.15° C. The weight loss was 1.3751% between room temperature and 120° C. (see FIG. 18).

TABLE 8

XRPD diffraction peak data table of crystalline Form VII of the dihydrochloride salt obtained in Example 8

| Peak Position 2θ angle (°) | Relative Intensity (%) of Peak |
|---|---|
| 5.907 | 6.66 |
| 6.473 | 40.3 |
| 8.285 | 48.29 |
| 11.480 | 19.14 |
| 11.889 | 51.86 |
| 12.146 | 8.6 |
| 12.929 | 82.84 |
| 13.217 | 17.44 |
| 14.551 | 100 |
| 16.524 | 24.89 |
| 17.558 | 24.8 |
| 18.219 | 11.69 |
| 18.836 | 18.71 |
| 19.467 | 9.69 |
| 20.415 | 16.56 |
| 21.812 | 18.18 |
| 22.182 | 21.54 |
| 22.824 | 20.83 |
| 23.620 | 22.01 |
| 24.373 | 38.93 |
| 24.759 | 35.19 |
| 26.132 | 10.81 |
| 26.626 | 17.91 |
| 27.490 | 21.6 |
| 27.946 | 9.23 |
| 28.574 | 8.33 |
| 29.080 | 17.38 |
| 29.555 | 34.02 |
| 30.283 | 17.74 |
| 30.702 | 10.11 |
| 31.328 | 16.38 |
| 32.052 | 8.74 |
| 33.319 | 5.6 |
| 34.182 | 9.21 |
| 35.133 | 6.53 |
| 35.639 | 4.39 |
| 36.877 | 5.46 |
| 37.991 | 3.56 |

Comparative Examples 1 and 2

Preparation of the Monohydrochloride salt and Malate Salt of Compound 1

Example 9

Preparation of the Oxalate Salt of Compound 1

Three samples (5 g, 10.8 mmol) of Preparation Example 1 were placed in reaction flasks, and the preparation of the monohydrochloride salt represented by Formula 3-3, the malate salt represented by Formula 7-1, and the oxalate salt represented by Formula 6-1 was carried out in the same operation procedure as that in Example 3 according to the reaction conditions as shown in the table below. The results were shown in Table 9. It was confirmed by nuclear magnetic hydrogen spectrum that the salt was formed.

(3-3)

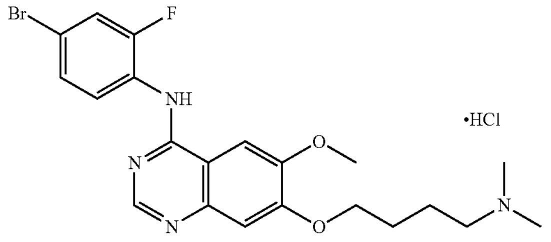

(7-1)

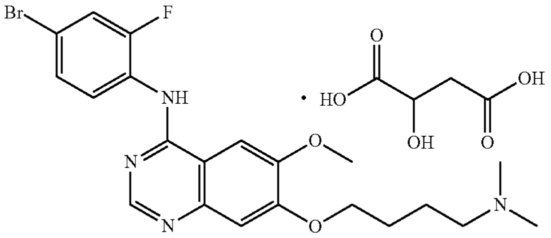

(6-1)

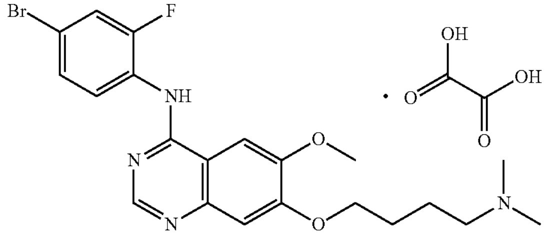

TABLE 9

Salt-forming reaction conditions and results

Figure 5:
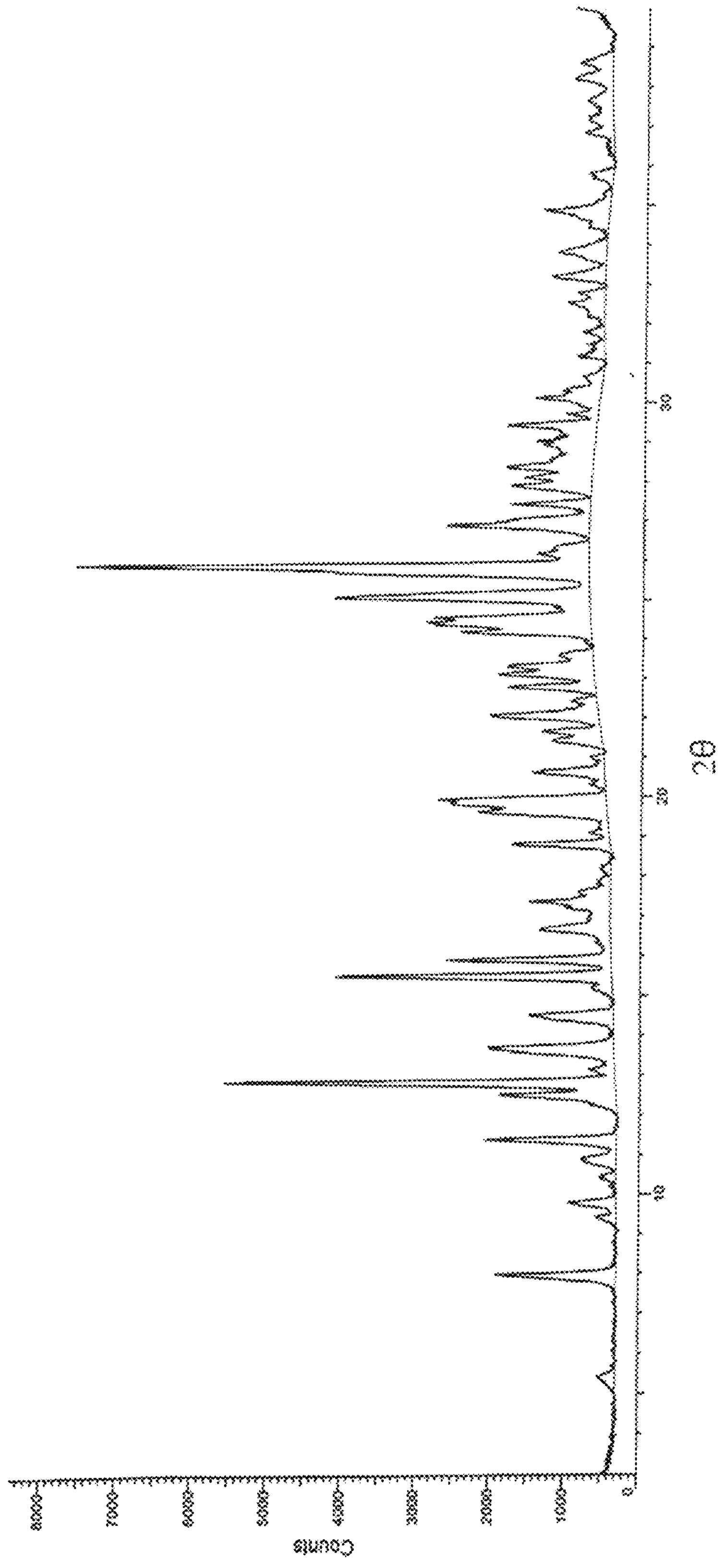
FIG. 5 is an XRPD spectrum of a monohydrochloride salt of Compound 1 obtained in Comparative Example 1.
Figure 6:
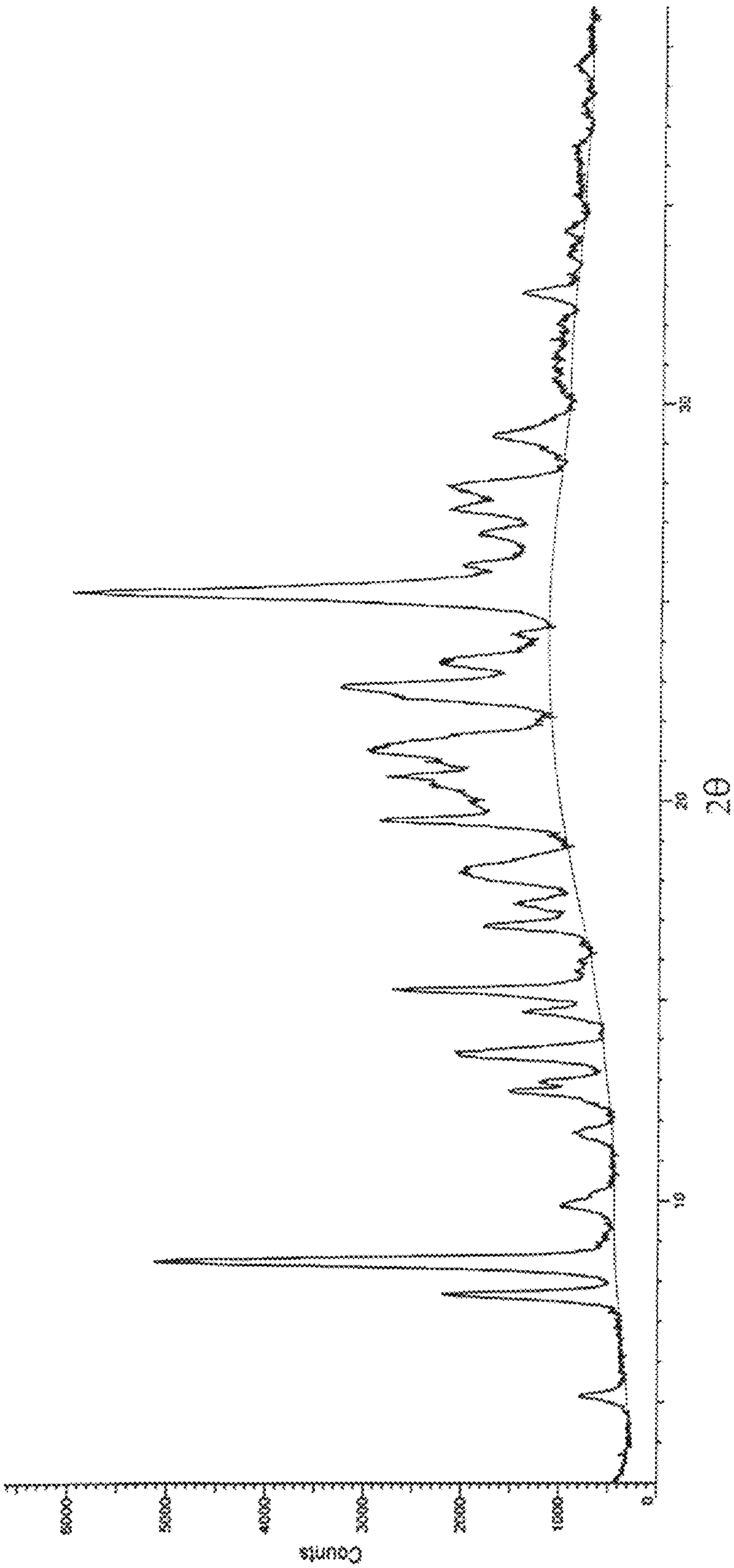
FIG. 6 is an XRPD spectrum of a malate salt of Compound 1 obtained in Comparative Example 2.

| Salt form | Acid amount | Reaction solvent | Heating temperature/° C. | Dilution solvent | Product | XRPD pattern |
|---|---|---|---|---|---|---|
| Comparative Example 1 Monohydrochloride salt | 10.8 mmol (0.9 mL) | Methanol (10 mL) | 60 ± 5 | Ethyl acetate (30 mL) | White powder (4.93 g) | FIG. 5 |
| Comparative Example 2 Malate salt (1:1) | 12.3 mmol (1.75 g) | Methanol (10 mL) | 60 ± 5 | Ethyl acetate (30 mL) | White powder (4.18 g) | FIG. 6 |

TABLE 9-continued

| Salt-forming reaction conditions and results | | | | | | |
|---|---|---|---|---|---|---|
| Salt form | Acid amount | Reaction solvent | Heating temperature/° C. | Dilution solvent | Product | XRPD pattern |
| Example 9 Oxalate salt (1:1) | 13.0 mmol (1.2 g) | Methanol (10 mL) | 60 ± 5 | Ethyl acetate (30 mL) | White powder (4.930 g) | FIG. 7 |

Note:
1. Confirmation method of base/acid ratio of Comparative Example 1: determination of chloride ion content;
2. Confirmation method of base/acid ratio of Comparative Example 2 and Example 9: Nuclear magnetic hydrogen spectrum, and determination of the content of the free base

Example 10

Preparation of the Dihydrochloride Salt Tetrahydrate

The sample of Example 1 (about 369 mg) was weighed, and water/acetone (1:1, v/v, total amount: 5 mL) were added thereto and stirred overnight at room temperature. The white solid was collected by filtration and dried overnight under vacuum at 50° C. The solid was determined as dihydrochloride salt tetrahydrate through detection. The resulting solid was subjected to X-ray powder diffraction, which was in crystalline form, and had an XRPD characterization spectrum as shown in FIG. 19.

Test Example 1

Solubility Test

The salts obtained in Preparation Example 1, Examples 1 to 4 and 9 and Comparative Examples 1 to 2 were tested for solubility in water and pH 2.0 buffer. The test results were shown in the following table:

TABLE 10

| Solubility results of different samples | | | |
|---|---|---|---|
| Example | Salt | Solubility (25° C., mg/mL) Medium: Water | Solubility (25° C., mg/mL) Medium: pH 2.0 buffer |
| Example 1 | Dihydrochloride | 40.07 | 14.29 |
| Example 2 | Dihydrochloride tetrahydrate | 34.32 | 7.69 |
| Example 3 | Sulfate | 10.91 | 5.00 |
| Example 4 | Maleate | 13.66 | 12.50 |
| Comparative Example 1 | Mono-hydrochloride | Jelly-like, solubility is not detected | / |
| Comparative Example 2 | Malate | Jelly-like, solubility is not detected | / |
| Example 9 | Oxalate | 2.89 | / |
| Preparation Example 1 | | 0.036 | 10.00 |

Note:
/: Not detected.

Results: Compared with Preparation Example 1, the samples of Examples 1 to 4 and Example 9 all achieved an increase in the solubility in water, and the solubility of the samples of Examples 1 to 4 all achieved an increase of at least 100 times in water, the solubility of the dihydrochloride salt was the best of all samples. The monohydrochloride salt and malate salt samples were dissolved in water, the resulting systems were jelly-like, and it was possible that the samples underwent crystal transformation in water and the dissolution effect is poor, so that the systems exhibited a non-solution state.

The samples obtained in Examples 1 to 4 with better solubility (>10 mg/mL) were further selected to determine the solubility of the samples in the pH 2.0 buffer, taken Preparation Example 1 as a control. It can be seen from the above results that the solubility of Preparation Example 1 was significantly improved, the solubility of the samples obtained in Examples 1 and 4 was still slightly better than that of Preparation Example 1, and the solubility of the samples obtained in Examples 2 and 3 was slightly lower than that of Preparation Example 1 under acidic conditions. In a simulated gastric fluid environment, although the solubility of Examples 1 and 4 was reduced, it was still superior to the free base compound of Preparation Example 1.

In addition, according to the general requirements for the solubility of APIs in pharmaceutical dosage forms, the solubility of the drug substance is greater than 0.1 g/L of solid oral dosage and 10 g/L of the solution formations such as injections or oral liquids. More importantly, the solubility of the APIs should meet the clinically required dosage concentration. Based on the solubility results in Table 10, Examples 1 to 4 and Example 9 can be considered for preparing solid oral dosage forms, and Examples 1 to 4 can also be considered for preparing solution formulations such as injections or oral liquids.

Test Example 2

Solubility Test in Biological Vehicles

The samples of Example 1 and Example 10 (20 mg each) were weighed, and different biological vehicles (2 mL) were added threreto to perform the solubility test, and the results were shown in Table 11.

TABLE 11

| Solubility of different samples in biological vehicles | | | | | |
|---|---|---|---|---|---|
| Example | Salt | Time | FaSSIF (pH 6.5) | FeSSIF (pH 5.0) | SGF (pH 1.2) |
| Example 1 | Dihydrochloride salt | 0.5 h | clear solution, >10 | 5.07 | clear solution, >10 |
| Example 10 | Dihydrochloride salt tetrahydrate | 0.5 h | clear solution, >10 | 7.30 | clear solution, >10 |

Results: The samples obtained in Example 1 and Example 10 were able to maintain good solubility in biological vehicles with different pH, and the dissolution rate was high.

Test Example 3

Long-Term Stability Test

An appropriate amount of the salt samples obtained in Examples 1 to 4 and 9 were sealed with a polyethylene film and placed for 5 months under the conditions of 40±2° C. and 75%±5% RH, and a long-term test was carried out. The results were as follows:

TABLE 12

Stability results and crystalline form detection results for different samples

| Example | Salt | 40 ± 2° C., 75% ± 5% RH, 5 months | | | |
|---|---|---|---|---|---|
| | | Appearance | Crystalline form | Purity (0 month) | Purity (5 months ) |
| Example 1 | Dihydrochloride | White powder | Unchanged | 99.62% | 99.60% |
| Example 2 | Dihydrochloride tetrahydrate | White powder | Unchanged | 98.55% | 98.56% |
| Example 3 | Sulfate | White powder | Unchanged | 98.83% | 98.84% |
| Example 4 | Maleate | White powder | Unchanged | 96.72% | 96.41% |
| Example 9 | Oxalate | White powder | Unchanged | 99.38% | 99.34% |

TABLE 13

XRPD data table of the crystal sample in Example 1 after the long-term stability test

| Peak Position 2θ angle (°) | Relative Intensity (%) of Peak |
|---|---|
| 8.026 | 3.6 |
| 9.374 | 3.2 |
| 9.795 | 9.8 |
| 10.199 | 4.6 |
| 12.355 | 15.4 |
| 15.021 | 3.1 |
| 15.468 | 4.8 |
| 16.000 | 5.3 |
| 16.731 | 3.5 |
| 17.437 | 2.9 |
| 18.274 | 2.7 |
| 18.757 | 100.0 |
| 19.140 | 8.2 |
| 20.263 | 13.9 |
| 21.621 | 3.3 |
| 22.264 | 6.8 |
| 22.923 | 5.4 |
| 24.483 | 19.2 |
| 24.871 | 13.6 |
| 25.296 | 6.2 |
| 25.923 | 9.6 |
| 26.091 | 4.5 |
| 26.849 | 2.3 |
| 27.655 | 4.5 |
| 28.564 | 8.1 |
| 29.866 | 8.4 |
| 30.810 | 7.1 |
| 31.563 | 1.7 |
| 32.272 | 7.6 |
| 33.860 | 2.9 |
| 35.043 | 1.5 |
| 36.412 | 4.7 |
| 37.668 | 3.4 |

Figure 10:
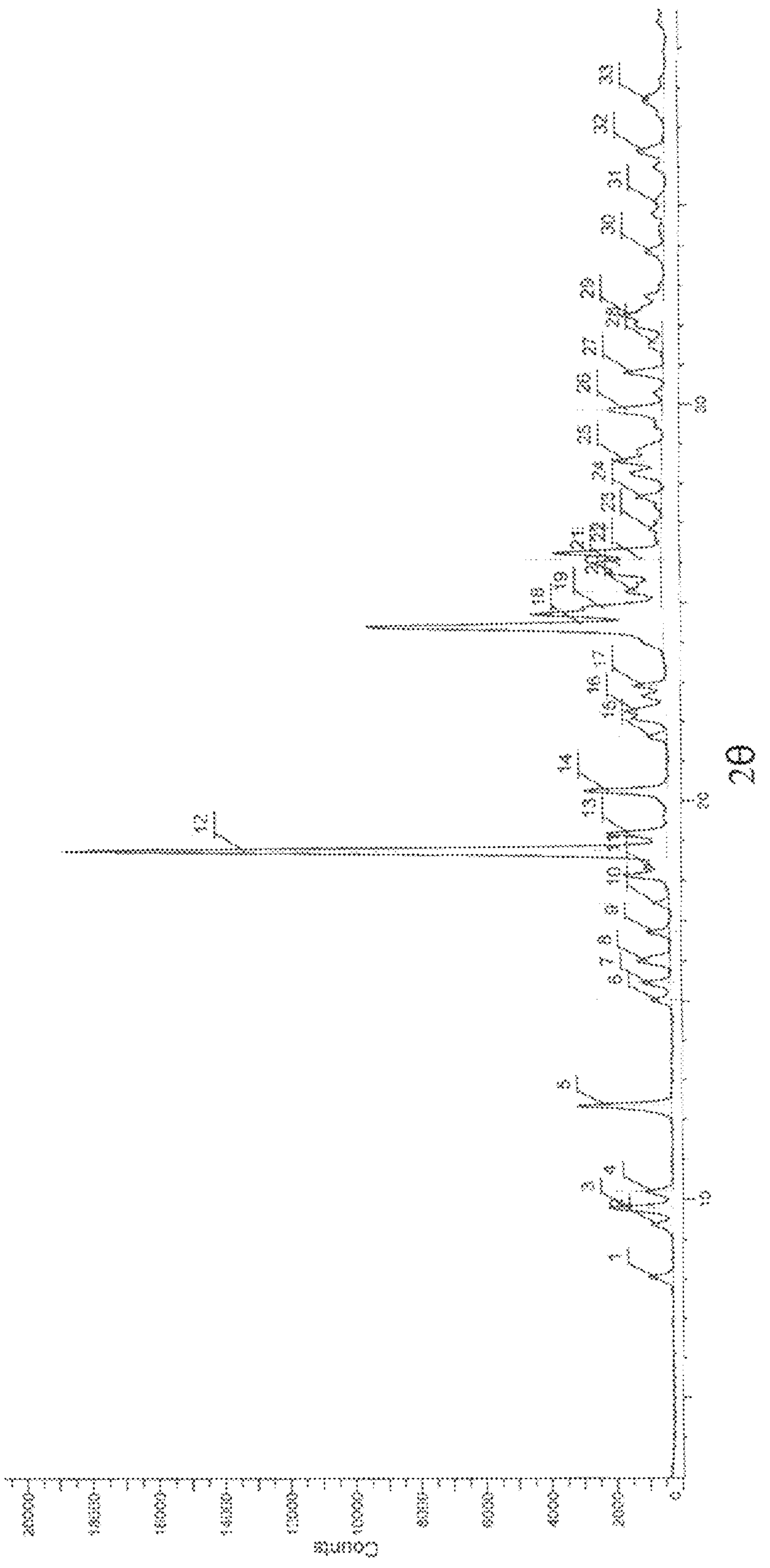
FIG. 10 is an XRPD spectrum of crystalline form I of a dihydrochloride salt, a solvate or hydrate thereof obtained in Example 1 after long-term stability test.

The XRPD spectrum of the crystalline form I of the dihydrochloride salt of Compound 1 obtained in Example 1 after the long-term stability test was shown in FIG. 10.

Results: After being placed for 5 months, the crystal samples of the salts of Examples 1 to 4 and 9 were all stable; the purity of the products was not significantly reduced, and the crystal form of each sample remained unchanged Test Example 4

Solid Stability Test

The dihydrochloride salt of Example 1 and the dihydrochloride salt tetrahydrate of Example 2 and Example 10 were all placed under the condition of 40° C./75% RH (open) for 7 days to perform the stability test. The results were shown in Table 14.

TABLE 14

Stability results and crystalline form detection results for different samples

| Example | Salt | 40° C./75% RH | |
|---|---|---|---|
| | | Crystalline form | Purity |
| Example 1 | Dihydrochloride salt | Unchanged | 99.64% |
| Example 2 | Dihydrochloride salt tetrahydrate | Unchanged | 98.54% |
| Example 10 | Dihydrochloride salt tetrahydrate | Unchanged | 99.74% |

Results: The dihydrochloride salt and the dihydrochloride salt tetrahydrate of Compound 1 obtained in Examples 1-2 and Example 10 maintained chemical stability and crystalline stability under the condition of 40° C./75% RH (open) for 7 days. Therefore, the samples obtained in Examples 1-2 and Example 10 had good thermal stability, and met the requirements for storage as APIs.

Test Example 5

Mechanical Stability Test

An appropriate amount of the dihydrochloride salt of Example 1 was subjected to mechanical grinding for 5 minutes, and X-ray powder diffraction was performed. The result showed that the crystalline form was not changed.

Test Example 6

Solubility Test in Conventional Organic Solvents

The solubility test of the sample of Preparation Example 1 in different organic solvents was carried out by using the method in the Pharmacopoeia (Volume II, the general examples), and the solubility of the sample of Example 1 in different organic solvents was estimated using the gravimetric method, and the results were shown in Table 15.

TABLE 15

The Comparison of Solubility in several conventional organic solvents between the sample of Preparation Example 1 and the dihydrochloride salt of Example 1

| Solvent | Solubility (mg/mL) | |
|---|---|---|
| | Preparation Example 1 | Example 1 |
| Methanol | >60 | 21~25 |
| Ethanol | 205.2 | ~0.55 |

TABLE 15-continued

| The Comparison of Solubility in several conventional organic solvents between the sample of Preparation Example 1 and the dihydrochloride salt of Example 1 | | |
|---|---|---|
| | Solubility (mg/mL) | |
| Solvent | Preparation Example 1 | Example 1 |
| Isopropanol | 51.05 | <0.40 |
| Acetone | 44.04 | <0.46 |
| Acetonitrile | 10.66 | <0.38 |
| Ethyl acetate | 30.38 | <0.38 |
| Tetrahydrofuran | 201.4 | <0.37 |
| Dichloromethane | 30.49 | <0.44 |

Note: The sample of Example 1 (~15 mg) was added to 0.5 mL of the different solvents listed in Table 15, and slurried at room temperature and 50° C., and the filtered sample was subjected to X-ray powder diffraction. The crystalline form was consistent with that of the dihydrochloride salt obtained in Example 1.

Results: Compound 1 of Preparation Example 1 had good solubility in various conventional organic solvents (all >10 mg/mL), and the dihydrochloride salt of Example 1 showed good solubility only in methanol, and had very poor solubility in the other seven commonly used organic solvents.

Therefore, it was achieved that the preparation of the dihydrochloride salt and the complete separation of the (unreacted) free base and the dihydrochloride salt were used by a suitable convention al organic solvent. The dihydrochloride salt was obtained with a higher yield (the mass loss was 1 ow due to low dissolution of the dihydrochloride salt in organic solvents) and purity.

In addition, the crystalline form corresponding to the dihydrochloride salt of Example 1 was obtained in the above conventional organic solvents, indicating that the crystalline form was stable in the conventional organic solvents.

Test Example 7

Pharmacodynamic Experiment of Human Melanoma A375 Nude Mice Xenograft Tumor Model A well-growing human melanoma A375 cell suspension was inoculated into the subcutaneous tissue of the forelimb axilla of nu/nu female nude mice in an inoculation volume of 0.1 mL containing approximately $1\times10^7$ tumor cells. When the tumor volume grew to 100 $mm^3$ or more, the mice with good tumor growth were selected, and the animals were evenly divided into 5 groups according to the tumor volume: a Vehicle group, a Vandetanib 12.5 mg/kg group, a Vandetanib 25 mg/kg group, an Example 1 sample 12.5 mg/kg group, and an Example 1 sample 25 mg/kg group, and there were 6 animals in each group. The Vehicle group was orally administered with distilled water, and the remaining groups were orally administered with the corresponding tested drugs in a dosing volume of 20 mL/kg, once a day, and continuously administered for 20 days. The animals were housed normally after administration, and the anti-tumor effect of the tested drugs was dynamically observed by using the method of measuring the diameter of the tumors. At the end of the experiment (Day 21), the animals were sacrificed, and the tumors, were stripped and weighed, and the tumor inhibition rate was calculated.

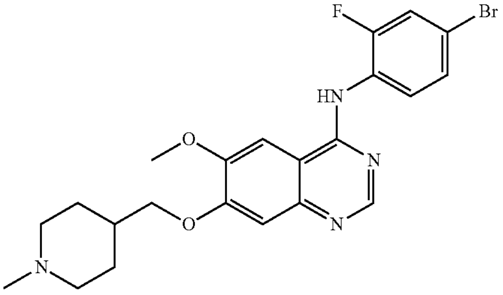

Vandetanib

TABLE 16

| Effects of Sample of Example 1 and Vandetanib on Tumor Weight of Human Melanoma A375 Xenograft Tumor Model | | | | |
|---|---|---|---|---|
| Group | Dosage mg/kg | Animal number (Survival/ total) | Tumor weight (g) | Inhibition rate % |
| Vehicle | — | 6/6 | 3.41 ± 1.39 | — |
| Example 1 | 12.5 | 6/6 | 1.77 ± 0.85**# | 47.99 |
| Example 1 | 25 | 6/6 | 1.34 ± 1.15** | 60.52 |
| Vandetanib | 12.5 | 6/6 | 2.89 ± 0.67 | 15.18 |
| Vandetanib | 25 | 6/6 | 1.90 ± 0.93** | 44.15 |

Note:
**Compared with the Vehicle group, $p < 0.01$;
compared with the same dosage of vandetanib group, $p < 0.05$.

Results: The sample of Example 1 was able to significantly inhibit the growth of tumors in dose-dependent manner, compared with the Vehicle group, and had a better tumor-inhibiting effect, compared to the control drug Vandetanib.

The effective dose in the mouse model was converted to the equivalent dose of an adult according to the conversion coefficient of the human and animal body surface areas (see "Pharmacological Experimental Methodology", editor-in-chief: Shuyun Xu). The effective doses of 12.5 mg/kg and 25 mg/kg in the mouse model correspond to the equivalent doses of 1.37 mg/kg and 2.74 mg/kg for an adult (70 kg), respectively. The oral single doses of 95.9 mg and 191.8 mg for an adult (70 kg). If a small-scale injection or solution (5 mL) is formlated, then the solubility of the drug needs to reach 11.51 mg/mL and 23.02 mg/mL or more, respectively (the absolute bioavailability of dogs and monkeys in animal pharmacokinetic experiments is about 60%, and therefore the oral availability of human is calculated as 60%). By analogy, the preparation of a small-scale liquid formulation (less than 5 mL) requires the higher solubility of the drug. Based on the solubility test results in Table 10, in order to prepare a 5 mL liquid formulation, if the administered dosage is 1.37 mg/kg, then Examples 1, 2 and 4 can meet the solubility requirements; if the administered dosage is 2.74 mg/kg, then the samples obtained in Examples 1 and 2 can meet the solubility requirements.

In summary, the inventors, after screening and exploring the salt forms of Compound 1, found that the solubility of the dihydrochloride salt, sulfate salt and maleate salt was significantly improved compared with Compound 1. They met the general requirements for the solubility of APIs of solid preparations and liquid preparations, and that the crystalline forms of the resulting salts had good stability. Among the three salts, the dihydrochloride salt had the best performances, can meet the solubility requirements of small-scale liquid preparations, had a good anti-tumor effect in vivo, and had the potential to be developed into medicines of various dosage forms and different specifications.

The invention claimed is:

1. A crystalline form of a salt of an arylaminoquinazoline-containing compound represented by Formula 2 or a hydrate thereof:

(2)

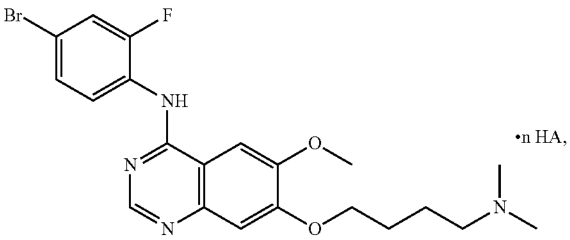

•n HA, wherein,

HA is hydrochloric acid;

n is 2; and the crystalline form of the salt of the arylaminoquinazoline-containing compound is a crystalline form I of a dihydrochloride salt represented by Formula 3-1 and having characteristic peaks at the following 2θ angles (°): 9.8±0.2°, 12.4±0.2°, 18.8±0.2°, 20.3±0.2°, and 24.6±0.2° in an X-ray powder diffraction spectrum with Cu-Kα radiation, (3-1)

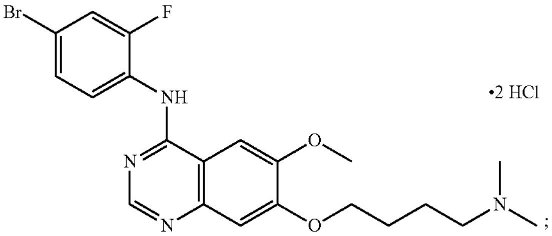

•2 HCl

;

or the crystalline form of the salt of the arylaminoquinazoline-containing compound is a crystal of a dihydrochloride salt tetrahydrate represented by Formula 3-2 and having characteristic peaks at the following 2θ angles (°): 6.0±0.2°, 6.8±0.2°, 12.4±0.2°, 15.5±0.2°, 25.4±0.2°, and 26.0±0.2° in an X-ray powder diffraction spectrum with Cu-Kα radiation, (3-2)

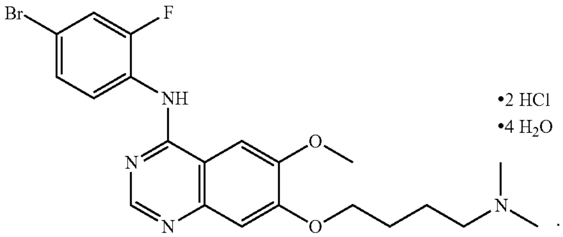

•2 HCl

•4 $H_2O$

.

2. A pharmaceutical composition comprising the salt of the arylaminoquinazoline-containing compound or the hydrate thereof according to claim 1, and one or more pharmaceutically acceptable carriers.

3. A method for treating a receptor tyrosine kinase-related disease in a patient, comprising administering to the patient a therapeutically effective amount of the salt of the arylaminoquinazoline-containing compound or the hydrate thereof according to claim 1, wherein the receptor tyrosine kinase is one or more of VEGFR, FLT, FGFR, RET, EGFR and mutants thereof.

4. A method for preparing the salt of the arylaminoquinazoline-containing compound or the hydrate thereof according to claim 1, comprising reacting an arylaminoquinazoline-containing compound represented by Formula 1 with HA in a solvent, isolating the salt of the arylaminoquinazoline-containing compound represented by Formula 2 or the hydrate thereof:

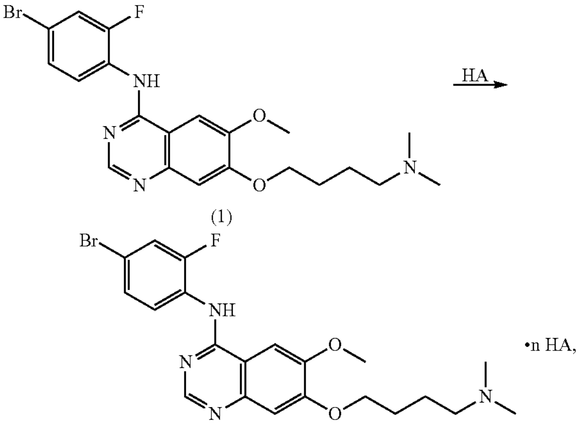

(1)

•n HA, (2)

wherein,

HA is hydrochloric acid;

n is 2; and a reaction temperature is 40-90° C.; and the solvent is selected from one or a combination of two of ethyl acetate, methanol or water.

5. The crystalline form of the salt of the arylaminoquinazoline-containing compound or the hydrate thereof according to claim 1, wherein the crystalline form I of the dihydrochloride salt represented by Formula 3-1 has characteristic peaks at the following 20 angles (°): 8.1±0.2°, 9.8±0.2°, 12.4±0.2°, 18.8±0.2°, 20.3±0.2°, 24.6±0.2°, and 29.9±0.2° in an X-ray powder diffraction spectrum with Cu-Kα radiation.

6. The crystalline form of the salt of the arylaminoquinazoline-containing compound or the hydrate thereof according to claim 1, wherein the crystalline form I of the dihydrochloride salt represented by Formula 3-1 has characteristic peaks at the following 20 angles (°): 8.1±0.2°, 9.8±0.2°, 12.4±0.2°, 18.8±0.2°, 19.3±0.2°, 20.3±0.2°, 24.6±0.2°, 28.6±0.2°, and 29.9±0.2° in an X-ray powder diffraction spectrum with Cu-Kα radiation.

7. The crystalline form of the salt of the arylaminoquinazoline-containing compound or the hydrate thereof according to claim 1, wherein the crystalline form I of the dihydrochloride salt represented by Formula 3-1 has characteristic diffraction peaks at the following 2θ angles (°): 8.1±0.2°, 9.8±0.2°, 12.4±0.2°, 16.1±0.2°, 18.8±0.2°, 19.3±0.2°, 20.3±0.2°, 24.6±0.2°, 28.6±0.2°, 29.9±0.2°, and 30.9±0.2° in an X-ray powder diffraction spectrum with Cu-Kα radiation.

8. The crystalline form of the salt of the arylaminoquinazoline-containing compound or the hydrate thereof according to claim 1, wherein the crystal of the dihydrochloride salt tetrahydrate represented by Formula 3-2 has characteristic peaks at the following 2θ angles (°): 6.0±0.2°, 6.8±0.2°, 12.4±0.2°, 15.5±0.2°, 18.0±0.2°, 24.4±0.2°, 25.4±0.2°, and 26.0±0.2° in an X-ray powder diffraction spectrum with Cu-Kα radiation.

9. The crystalline form of the salt of the arylaminoquinazoline-containing compound or the hydrate thereof according to claim 1, wherein the crystal of the dihydrochloride salt tetrahydrate represented by Formula 3-2 has characteristic peaks at the following 2θ angles (°): 6.0±0.2°, 6.8±0.2°, 12.4±0.2°, 15.5±0.2°, 18.0±0.2°, 22.7±0.2°, 24.4±0.2°, 25.4±0.2°, and 26.0±0.2° in an X-ray powder diffraction spectrum with Cu-Kα radiation.

10. The method according to claim 3, wherein the receptor tyrosine kinase-related disease is a tumor.

11. The method according to claim 10, wherein the tumor is thyroid cancer, biliary tract cancer, epidermoid cancer, melanoma, colorectal cancer, gastric cancer, esophageal cancer, pancreatic cancer, kidney cancer, liver cancer, lung cancer or ovarian cancer.

12. The method according to claim 11, wherein the thyroid cancer is medullary thyroid cancer, and the lung cancer is non-small cell lung cancer.

* * * * *